United States Patent
Skands et al.

(10) Patent No.: US 12,377,133 B2
(45) Date of Patent: Aug. 5, 2025

(54) DRY PHARMACEUTICAL FORMULATIONS OF CNP CONJUGATES

(71) Applicant: Ascendis Pharma Growth Disorders A/S, Hellerup (DK)

(72) Inventors: Anja R. H. Skands, Hellerup (DK); Ulrich Hersel, Heidelberg (DE); Charlotte Pinholt, Hellerup (DK); Stefan Heinig, Heidelberg (DE)

(73) Assignee: ASCENDIS PHARMA GROWTH DISORDERS A/S, Hellerup (DK)

( * ) Notice: Subject to any disclaimer, the term of this patent is extended or adjusted under 35 U.S.C. 154(b) by 1006 days.

(21) Appl. No.: 17/428,604

(22) PCT Filed: Feb. 10, 2020

(86) PCT No.: PCT/EP2020/053304
§ 371 (c)(1),
(2) Date: Aug. 4, 2021

(87) PCT Pub. No.: WO2020/165081
PCT Pub. Date: Aug. 20, 2020

(65) Prior Publication Data
US 2022/0118053 A1    Apr. 21, 2022

(30) Foreign Application Priority Data
Feb. 11, 2019   (EP) .................................. 19156488

(51) Int. Cl.
| | |
|---|---|
| A61K 38/22 | (2006.01) |
| A61K 9/00 | (2006.01) |
| A61K 9/19 | (2006.01) |
| A61K 47/12 | (2006.01) |
| A61K 47/18 | (2017.01) |
| A61K 47/26 | (2006.01) |
| A61K 47/54 | (2017.01) |
| A61K 47/60 | (2017.01) |

(52) U.S. Cl.
CPC ............ *A61K 38/22* (2013.01); *A61K 9/0019* (2013.01); *A61K 9/19* (2013.01); *A61K 38/2242* (2013.01); *A61K 47/12* (2013.01); *A61K 47/18* (2013.01); *A61K 47/26* (2013.01); *A61K 47/54* (2017.08); *A61K 47/60* (2017.08)

(58) Field of Classification Search
None
See application file for complete search history.

(56) References Cited

U.S. PATENT DOCUMENTS

| | | |
|---|---|---|
| 6,833,358 B1 | 12/2004 | Nakata et al. |
| 7,585,837 B2 | 9/2009 | Shechter et al. |
| 8,198,242 B2 | 6/2012 | Wendt et al. |
| 8,377,884 B2 | 2/2013 | Wendt et al. |
| 8,551,937 B2 | 10/2013 | Wakabayshi |
| 8,618,124 B2 | 12/2013 | Greenwald et al. |
| 8,703,893 B2 | 4/2014 | Hernandez et al. |
| 8,754,190 B2 | 6/2014 | Ashley et al. |
| 8,946,405 B2 | 2/2015 | Ashley et al. |
| 10,052,366 B2 | 8/2018 | Crine et al. |
| 10,835,578 B2 | 11/2020 | Rau et al. |
| 11,154,593 B2 | 10/2021 | Rau et al. |
| 11,224,661 B2 | 1/2022 | Sprogøe et al. |
| 11,311,604 B2 | 4/2022 | Rau et al. |
| 11,389,510 B2 | 7/2022 | Sprogøe et al. |
| 11,389,511 B2 | 7/2022 | Sprogøe et al. |
| 11,413,351 B2 | 8/2022 | Rau et al. |
| 11,564,974 B2 | 1/2023 | Holton-Anderson et al. |
| 12,083,182 B2 | 9/2024 | Sprogøe et al. |
| 2003/0068313 A1 | 4/2003 | Nakao |
| 2004/0137557 A1 | 7/2004 | DeFrees et al. |
| 2008/0113027 A1 | 5/2008 | Asgharian et al. |
| 2009/0258017 A1 | 10/2009 | Callahan et al. |
| 2010/0316625 A1 | 12/2010 | Mankarious et al. |
| 2012/0035101 A1 | 2/2012 | Fares et al. |
| 2012/0276190 A1 | 11/2012 | Fitzgerald et al. |
| 2012/0316114 A1 | 12/2012 | Wendt et al. |
| 2012/0322721 A1 | 12/2012 | Rasmussen et al. |
| 2013/0315966 A1 | 11/2013 | Randolph et al. |
| 2017/0080049 A1 | 3/2017 | Morozumi |
| 2017/0189487 A1 | 7/2017 | Ohori et al. |
| 2017/0368189 A1 | 12/2017 | Sprogoe et al. |
| 2019/0000926 A1 | 1/2019 | Rau et al. |
| 2019/0008977 A1 | 1/2019 | Rau et al. |
| 2019/0015481 A1 | 1/2019 | Rau et al. |
| 2019/0022237 A1 | 1/2019 | Sprogøe et al. |

(Continued)

FOREIGN PATENT DOCUMENTS

| | | |
|---|---|---|
| CA | 2763817 A1 | 10/2004 |
| EP | 2275119 A1 | 1/2011 |
| EP | 1534334 B1 | 6/2014 |
| EP | 2853273 A1 | 4/2015 |
| EP | 3078387 A1 | 10/2016 |
| EP | 3135296 A1 | 3/2017 |
| RU | 2573911 C2 | 1/2016 |
| WO | WO 2000/0072870 A1 | 12/2000 |
| WO | WO 02/089789 A1 | 11/2002 |
| WO | WO 2004/047871 A2 | 6/2004 |
| WO | WO 2005/099768 A2 | 10/2005 |

(Continued)

OTHER PUBLICATIONS

"BioMarin Announces Decision to Start Phase 3 Program for PEG-PAL in 2Q 2013," BioMarin, Press Release, 3 pages, (2012). [Author Unknown].

(Continued)

*Primary Examiner* — Christina Bradley
(74) *Attorney, Agent, or Firm* — Alston & Bird LLP

(57) ABSTRACT

A dry pharmaceutical formulation, wherein the pharmaceutical formulation comprises a CNP conjugate, a buffering agent and a bulking agent and wherein the CNP conjugate comprises a CNP moiety that is covalently and reversibly conjugated to a polymeric moiety.

26 Claims, No Drawings
Specification includes a Sequence Listing.

(56) References Cited

U.S. PATENT DOCUMENTS

| | | |
|---|---|---|
| 2019/0255183 A1 | 8/2019 | Sprogøe et al. |
| 2019/0328840 A1 | 10/2019 | Sprogøe et al. |
| 2019/0328841 A1 | 10/2019 | Sprogøe et al. |
| 2020/0276270 A1 | 9/2020 | Holton-Anderson et al. |
| 2021/0069339 A1 | 3/2021 | Sprogøe et al. |
| 2021/0077584 A1 | 3/2021 | Rau et al. |
| 2021/0177942 A1 | 6/2021 | Rau et al. |
| 2022/0088206 A1 | 3/2022 | Sprogøe et al. |
| 2022/0211817 A1 | 7/2022 | Rau et al. |
| 2022/0296682 A1 | 9/2022 | Rau et al. |
| 2022/0331438 A1 | 10/2022 | Rau et al. |
| 2022/0409700 A1 | 12/2022 | Sprogøe et al. |
| 2023/0103820 A1 | 4/2023 | Sprogøe et al. |
| 2023/0116746 A1 | 4/2023 | Sprogøe et al. |
| 2023/0302091 A1 | 9/2023 | Holton-Anderson et al. |

FOREIGN PATENT DOCUMENTS

| | | | | |
|---|---|---|---|---|
| WO | WO 2006/136586 A2 | 12/2006 | | |
| WO | WO 2008/031045 A2 | 3/2008 | | |
| WO | WO 2008/034122 A2 | 3/2008 | | |
| WO | WO 2008/136611 A1 | 11/2008 | | |
| WO | WO 2008/155134 A1 | 12/2008 | | |
| WO | WO 2009/009712 A1 | 1/2009 | | |
| WO | WO 2009/067639 A2 | 5/2009 | | |
| WO | WO 2009/095479 A2 | 8/2009 | | |
| WO | WO 2009/143412 A2 | 11/2009 | | |
| WO | WO 2009/156481 A1 | 12/2009 | | |
| WO | WO 2010/033217 A1 | 3/2010 | | |
| WO | WO 2010/091122 A1 | 8/2010 | | |
| WO | WO 2010/135541 A2 | 11/2010 | | |
| WO | WO 2011/012722 A1 | 2/2011 | | |
| WO | WO 2011/075471 A2 | 6/2011 | | |
| WO | WO 2011/082368 A2 | 7/2011 | | |
| WO | WO 2011/089214 A1 | 7/2011 | | |
| WO | WO 2011/089215 A1 | 7/2011 | | |
| WO | WO 2011/089216 A1 | 7/2011 | | |
| WO | WO 2011/123813 A2 | 10/2011 | | |
| WO | WO 2011/144756 A1 | 11/2011 | | |
| WO | WO 2013/024047 A1 | 2/2013 | | |
| WO | WO 2013/024048 A1 | 2/2013 | | |
| WO | WO 2013/024049 A1 | 2/2013 | | |
| WO | WO 2013/024052 A1 | 2/2013 | | |
| WO | WO 2013/024053 A1 | 2/2013 | | |
| WO | WO 2013/036857 A1 | 3/2013 | | |
| WO | WO 2013/160340 A1 | 10/2013 | | |
| WO | WO 2015/083582 A1 | 6/2015 | | |
| WO | WO 2015/129812 A1 | 9/2015 | | |
| WO | WO 2016/020373 A1 | 2/2016 | | |
| WO | WO 2016/110577 A1 | 7/2016 | | |
| WO | WO 2017/020034 A1 | 2/2017 | | |
| WO | WO-2017100400 A2 | * | 6/2017 | ........... A61K 31/573 |
| WO | WO 2017/118698 A1 | 7/2017 | | |
| WO | WO 2017/118700 A1 | 7/2017 | | |
| WO | WO 2017/118703 A1 | 7/2017 | | |
| WO | WO 2017/118704 A1 | 7/2017 | | |
| WO | WO 2017/118707 A1 | 7/2017 | | |
| WO | WO-2017118693 A1 | * | 7/2017 | ......... A61K 31/4015 |
| WO | WO 2018/060314 A1 | 4/2018 | | |
| WO | WO 2020/165081 A1 | 8/2020 | | |

OTHER PUBLICATIONS

"PEG Products," JenKem Technology USA, 7 pages, (2015). [Retrieved from the Internet: <URL: http://www.jenkemusa.com/products>]. [Author Unknown].

Ansel, et al., "Drug Dosage and Terminology," Pharmaceutical Dosage Forms and Drug Delivery, Seventh Edition, pp. 48-53, (1999).

Bowie et al., "Deciphering the Message in Protein Sequences: Tolerance to Amino Acid Substitutions," Science, 247:1306-1310, (1990). [Retrieved from the Internet May 18, 2011: <URL: http://www.sciencemag.org >].

Bruno et al., "Basics and recent advances in peptide and protein drug delivery," Ther Deliv. 4(11): 1443-1467, (Nov. 2013).

Chen et al., "Fusion Protein Linkers: Property, Design and Functionality," Adv Drug Deliv Rev., 65(10): 1357-1369, (Oct. 2013).

Cohen, "Short-limb skeletal dysplasias and raniosynostosis: what do they have in common?" Pediatr Radiol, 27, 442-446, (1997).

De Plater, et al., "A C-type natriuretic peptide from the venom of the platypus (*Ornithorhynchus anatinus*): Structure and pharmacology," Comparative Biochemistry and Physiology Part C, 120, 99-110, (1998).

Delgado et al., "The Uses and Properties of PEG-Linked Proteins," Critical Re-views in Therapeutic Drug Carrier Systems, , 9(3,4):249-304, (1992).

Einav, et al., "The hepatitis C virus (HCV) NS4B RNA binding inhibitor clemizole is highly synergistic with HCV protease inhibitors," Journal of Infectious Diseases, 202(1):65-74, (2010).

EudraCT No. 2019-002754-22v1 Clinical trial results, Apr. 11, 2023.

Farnum et al., "In vivo Delivery of Fluoresceinated Dextrans to the Murine Growth Plate: Imaging of Three Vascular Routes by Multiphoton Microscopy," Anat Rec A Discov Mol Cell Evol Biol, 288(1):91-103, doi:10.1002/ar.a.20272, (2006).

Furuya et al., "Structural requirements of C-type natriuretic peptide for elevation of cyclic GMP in cultured vascular smooth muscle cells," Biochemical and Biophysical Research Communications, 183(3):964-969, (1992).

He et al., "Peptide Conjugates with Small Molecules Designed to Enhance Efficacy and Safety," Molecules, 24, 1855, (2019).

Igaki et al., "Effects of Intravenously Administered C-type Natriuretic Peptide in Humans: Comparison with Atrial Natriuretic Peptide," Hypertens Res, 21:7-13, (1998).

Jiang, et al., "Effect of Sialylated O-Glycans in Pro-Brain Natriuretic Peptide Stability," Clin Chem, 56(6): 959-966, (Jun. 2010).

Klag, et al., "Advances in treatment of achondroplasia and osteoarthritis," Human Molecular Genetics, vol. 25, No. R1, (2016).

Lorget et al., "Evaluation of the Therapeutic Potential of a CNP Analog in a Fgfr3 Mouse Model Recapitulating Achondroplasia," AJHG, 91(6):1108-1114, (2012).

Lu et al., "Linkers Having a Crucial Role in Antibody-Drug Conjugates," Int. J. Mol. Sci, 17, 561, (2016).

Martz et al., "sFGFR for achondroplasia," SciBX, 6(40), 2 pages, doi:10.1038/scibx.2013.1120, (2013).

Martz et al., "sFGFR for achondroplasia," SciBX, Nature Publishing Group, 2 pages, (2013).

Mehta, et al., "The Use of Somatropin (Recombinant Growth Hormone) in Children of Short Stature," Pediatr Drugs, 4(1): 37-47, (2002).

Merrifield, "Solid Phase Peptide Synthesis. I. The Synthesis of a Tetrapeptide," J. Am. Chem. Soc., 85(14):2149-2154, doi: 10.1021/ja00897a025, (1963).

Molina Clinical Policy, Subject: Recombinant Human Growth Hormone: Pediatric Conditions Without GHD, Policy No. MCP-004-C, 24 pages, (2010).

NOF America Corporation, Sunbright® CS, GS, AS, HS, TS and PS Series (NHS active esters/Carbonate), retreived from the internet at: www.nofamerica.com/store/index.php?dispatch=categories.view &category_id=7 on Mar. 19, 2021.

Oefner, et al., "Structure of Human Neutral Endopeptidase (Neprilysin) Complexed with Phosphoramindon," J. Mol. Biol., 296, 341-349, (2000).

Pejchalova, et al., "C-natriuretic peptide: An important regulator of cartilage," Molecular Genetics and Metabolism, 92, 210--215, (2007).

Potter et al., "Natriuretic peptide metabolism, clearance and degradation," FEBS J, 278(11):1808-1817, doi: 10.1111/j.1742-4658. 2011.08082.x, (2011).

Ramaswami, et al., "Treatment of Achondroplasia with Growth hormones: Six Year of Experience," Pediatric Research, 22 pages, (1999).

Sakaguchi, et al., "Characterisation of C-type natriuretic peptide receptors in the gill of dogfish Triakis scyllia," Journal of Endocrinology, 156, 127-124, (1998).

(56) References Cited

OTHER PUBLICATIONS

Samson et al., "C-type natriuretic peptide mediates the hypothalamic actions of the natriuretic peptides to inhibit luteinizing hormone secretion," Endocrinology, 132(2):504-509, doi: 10.1210/END0.132.2.8425472, (1993).
STNext search notes for U.S. Pat. No. 10,052,366, Accession No. 2013:644347, Dated Feb. 11, 2021.
Takano, et al., "Molecular evolution of shark C-type natriuretic peptides," Zoolog Sci, 11 (3):441-454, (1994).
Tallarida, "Quantitative Methods for Assessing Drug Synergism," Genes & Cancer, 2(11) pp. 1003-1008, (2011).
Wang et al., "Effect of liposome-encapsulated C-type natriuretic peptide on vascular response," Database Chemabs, 1 page, Accession No. 1999:790321, (1999).
Wendt et al., "Neutral Endopeptidase-Resistant C-Type Natriuretic Peptide Variant Represents a New Therapeutic Approach for Treatment of Fibroblast Growth Factor Receptor 3-Related Dwarfism," J Pharmacol Exp Ther, 353(1):132-149, (2015).
Yamashita, et al., "Statin treatment rescues FGFR3 skeletal dysplasia phenotypes," Nature, 513, 507-511, (2014).
Yampolsky, et al., "The Exchangeability of Amino Acids in Proteins," Genetics, 170: 1459-1472, (Aug. 2005).
SG 11202107446Q Search Report mailed Nov. 17, 2022.
SG 11202107446Q Written Opinion mailed Nov. 21, 2022.
U.S. Appl. No. 15/538,641, Non-Final Office Action mailed Sep. 6, 2018.
U.S. Appl. No. 15/538,641, Requirement for Restriction/Election mailed Jun. 14, 2018.
U.S. Appl. No. 16/066,058, Non-Final Office Action mailed Feb. 23, 2021.
U.S. Appl. No. 16/066,058, Non-Final Office Action mailed Dec. 31, 2019.
U.S. Appl. No. 16/066,058, Notice of Allowance and Interview Summary mailed Mar. 11, 2022.
U.S. Appl. No. 16/066,058, Requirement for Restriction/Election mailed Oct. 4, 2019.
U.S. Appl. No. 16/066,980, Non-Final Office Action mailed Apr. 19, 2021.
U.S. Appl. No. 16/066,980, Notice of Allowance mailed Dec. 13, 2021.
U.S. Appl. No. 16/066,980, Requirement for Restriction/Election mailed Dec. 28, 2020.
U.S. Appl. No. 16/067,057, Corrected Notice of Allowance mailed Sep. 18, 2020.
U.S. Appl. No. 16/067,057, Final Office Action mailed Dec. 2, 2019.
U.S. Appl. No. 16/067,057, Non-Final Office Action mailed Jun. 25, 2019.
U.S. Appl. No. 16/067,057, Notice of Allowance mailed Apr. 9, 2020.
U.S. Appl. No. 16/067,057, Notice of Allowance mailed Jul. 29, 2020.
U.S. Appl. No. 16/067,070, Final Office Action mailed Aug. 28, 2020.
U.S. Appl. No. 16/067,070, Non-Final Office Action mailed Jan. 26, 2021.
U.S. Appl. No. 16/067,070, Non-Final Office Action mailed Dec. 30, 2019.
U.S. Appl. No. 16/067,070, Notice of Allowance mailed Feb. 24, 2022.
U.S. Appl. No. 16/067,070, Notice of Allowance mailed Oct. 18, 2021.
U.S. Appl. No. 16/067,070, Requirement for Restriction/Election mailed Aug. 21, 2019.
U.S. Appl. No. 16/067,095, Final Office Action mailed Nov. 10, 2020.
U.S. Appl. No. 16/067,095, Non-Final Office Action mailed Mar. 20, 2020.
U.S. Appl. No. 16/067,095, Non-Final Office Action mailed Apr. 5, 2021.
U.S. Appl. No. 16/067,095, Non-Final Office Action mailed Nov. 19, 2021.
U.S. Appl. No. 16/067,095, Notice of Allowance and Interview Summary mailed Mar. 16, 2022.
U.S. Appl. No. 16/067,095, Notice of Allowance mailed Jul. 28, 2021.
U.S. Appl. No. 16/067,095, Requirement for Restriction/Election mailed Oct. 10, 2019.
U.S. Appl. No. 16/067,111, Final Office Action mailed Sep. 17, 2020.
U.S. Appl. No. 16/067,111, Non-Final Office Action mailed Feb. 5, 2020.
U.S. Appl. No. 16/067,111, Notice of Allowability mailed Dec. 6, 2021.
U.S. Appl. No. 16/067,111, Notice of Allowance mailed Sep. 1, 2021.
U.S. Appl. No. 16/067,111, Requirement for Restriction/Election mailed Aug. 30, 2019.
U.S. Appl. No. 16/269,097, Non-Final Office Action mailed Feb. 14, 2020.
U.S. Appl. No. 16/338,185, Final Office Action mailed Apr. 7, 2021.
U.S. Appl. No. 16/338,185, Non-Final Office Action mailed Oc. 25, 2021.
U.S. Appl. No. 16/338,185, Non-Final Office Action mailed Nov. 18, 2020.
U.S. Appl. No. 16/338,185, Notice of Allowance mailed May 25, 2022.
U.S. Appl. No. 16/338,185, Requirement for Restriction/Election mailed Jul. 6, 2020.
U.S. Appl. No. 16/933,127, Non-Final Office Action mailed Dec. 27, 2021.
U.S. Appl. No. 16/993,127, Requirement for Restriction/Election mailed Jul. 28, 2021.
U.S. Appl. No. 17/005,272, Non-Final Office Action mailed Aug. 16, 2021.
U.S. Appl. No. 17/184,561, Corrected Notice of Allowance mailed Sep. 23, 2021.
U.S. Appl. No. 17/184,561, Non-Final Office Action mailed May 3, 2021.
U.S. Appl. No. 17/184,561, Notice of Allowance mailed Aug. 18, 2021.
U.S. Appl. No. 17/526,481, Non-Final Office Action mailed Aug. 7, 2023.
U.S. Appl. No. 17/538,971, Non-Final Office Action mailed May 25, 2023.
U.S. Appl. No. 17/538,971, Notice of Allowance mailed Jan. 18, 2024.
U.S. Appl. No. 17/538,971, Notice of Allowance mailed May 9, 2024.
U.S. Appl. No. 17/538,971, Notice of Allowance mailed Oct. 10, 2023.
U.S. Appl. No. 17/696,769, Requirement for Restriction/Election mailed Mar. 16, 2022.
U.S. Appl. No. 17/752,664, Final Office Action mailed Aug. 28, 2023.
U.S. Appl. No. 17/752,664, Non-Final Office Action mailed Mar. 14, 2024.
U.S. Appl. No. 17/752,664, Non-Final Office Action mailed Mar. 23, 2023.
U.S. Appl. No. 17/752,664, Requirement for Restriction/Election mailed Oct. 14, 2022.
U.S. Appl. No. 17/839,390, Non-Final Office Action mailed Nov. 6, 2023.
U.S. Appl. No. 17/842,436, Final Office Action mailed Mar. 3, 2023.
U.S. Appl. No. 17/842,436, Non-Final Office Action mailed Aug. 17, 2023.
U.S. Appl. No. 17/842,436, Non-Final Office Action mailed Nov. 21, 2022.
U.S. Appl. No. 17/842,436, Notice of Allowance mailed Apr. 5, 2024.
U.S. Appl. No. 17/842,436, Notice of Allowance mailed Jun. 26, 2023.

(56) References Cited

OTHER PUBLICATIONS

U.S. Appl. No. 18/145,676, Requirement for Restriction/Election mailed Nov. 20, 2023.
U.S. Appl. No. 18/407,324, Non-Final Office Action mailed Jul. 19, 2024.
U.S. Appl. No. 16/066,058, Final Office Action mailed Aug. 20, 2020.
U.S. Appl. No. 16/067,070, Notice of Allowance mailed Jun. 3, 2021.
U.S. Appl. No. 16/067,111, Notice of Allowance mailed Feb. 5, 2021.
U.S. Appl. No. 16/067,111, Notice of Allowance mailed May 12, 2021.
U.S. Appl. No. 16/338,185, Notice of Allowance mailed Sep. 27, 2022.
U.S. Appl. No. 17/839,390, Requirement for Restriction/Election mailed Jul. 6, 2023.
U.S. Appl. No. 17/848,180, Non-Final Office Action mailed Feb. 26, 2024.
U.S. Appl. No. 17/848,180, Requirement for Restriction/Election mailed Sep. 13, 2023.
WIPO Application No. PCT/EP2016/050298, PCT International Preliminary Report on Patentability issued Jul. 11, 2017.
WIPO Application No. PCT/EP2016/050298, PCT International Search Report mailed Apr. 8, 2017.
WIPO Application No. PCT/EP2016/050298, PCT Written Opinion of the International Searching Authority mailed Apr. 8, 2017.
WIPO Application No. PCT/EP2017/050201, PCT International Preliminary Report on Patentability issued Jul. 10, 2018.
WIPO Application No. PCT/EP2017/050201, PCT International Search Report mailed Apr. 12, 2017.
WIPO Application No. PCT/EP2017/050201, PCT Written Opinion of the International Searching Authority mailed Apr. 12, 2017.
WIPO Application No. PCT/EP2017/0502091, PCT International Preliminary Report on Patentability issued Jul. 10, 2018.
WIPO Application No. PCT/EP2017/0502091, PCT Written Opinion of the International Searching Authority mailed Apr. 11, 2017.
WIPO Application No. PCT/EP2017/050213, PCT International Preliminary Report on Patentability issued Jul. 10, 2018.
WIPO Application No. PCT/EP2017/050213, PCT International Search Report mailed May 11, 2017.
WIPO Application No. PCT/EP2017/050213, PCT Written Opinion of the International Searching Authority mailed May 11, 2017.
WIPO Application No. PCT/EP2017/050217, PCT International Preliminary Report on Patentability issued Jul. 10, 2018.
WIPO Application No. PCT/EP2017/050217, PCT International Search Report mailed Apr. 4, 2017.
WIPO Application No. PCT/EP2017/050217, PCT Written Opinion of the International Searching Authority mailed Apr. 4, 2017.
WIPO Application No. PCT/EP2017/050220, PCT International Preliminary Report on Patentability issued Jul. 10, 2018.
WIPO Application No. PCT/EP2017/050220, PCT International Search Report mailed Apr. 10, 2017.
WIPO Application No. PCT/EP2017/050220, PCT Written Opinion of the International Searching Authority mailed Apr. 10, 2017.
WIPO Application No. PCT/EP2017/050224, PCT International Preliminary Report on Patentability issued Jul. 10, 2018.
WIPO Application No. PCT/EP2017/050224, PCT International Search Report mailed Mar. 23, 2017.
WIPO Application No. PCT/EP2017/050224, PCT Written Opinion of the International Searching Authority mailed Mar. 23, 2017.
WIPO Application No. PCT/EP2017/074596, PCT International Preliminary Report on Patentability issued Apr. 2, 2019.
WIPO Application No. PCT/EP2020/053304, PCT International Search Report and Written Opinion of the International Searching Authority mailed Aug. 4, 2020.
WIPO Application No. PCT/EP2017/0502091, PCT International Search Report mailed Apr. 11, 2017.
U.S. Appl. No. 17/696,769, Non-Final Office Action mailed Oct. 9, 2024.
U.S. Appl. No. 17/752,664, Final Office Action mailed Nov. 1, 2024.
U.S. Appl. No. 17/842,436, Corrected Notice of Allowance mailed Sep. 26, 2024.
U.S. Appl. No. 18/145,676, Non-Final Office Action mailed Oct. 17, 2024.
Wang, "Lyophilization and development of solid protein pharmaceuticals," International Journal of Pharmaceutics, 203, 1-60, (2000).
Roche Data Sheet Herceptin® Trastuzumab 150 mg and 440 mg powder for concentrate for solution for infusion, 140625, (Jun. 2014).
Genentech, Inc. Xolair® highlights of prescribing information, revised Sep. 2014.

\* cited by examiner

DRY PHARMACEUTICAL FORMULATIONS OF CNP CONJUGATES

CROSS-REFERENCE TO RELATED APPLICATIONS

This application is the US national stage entry of PCT/EP2020/053304 filed Feb. 10, 2020, which claims the benefit of EP Application Serial No. 19156488.9 filed Feb. 11, 2019.

REFERENCE TO SEQUENCE LISTING

This application includes an electronic sequence listing in a file named 562643SEQLST.TXT, created on Aug. 2, 2021and containing 47,900 bytes, which is incorporated by reference.

The present invention relates to dry pharmaceutical formulations comprising a CNP conjugate, a buffering agent and a bulking agent.

Achondroplasia (ACH) is a genetic disorder which occurs due to an autosomal dominant mutation in the fibroblast-growth-factor-receptor 3 (FGFR3) gene, that causes an abnormality of cartilage formation and results in dwarfism. C-type Natriuretic Peptide (CNP) is a hormone that binds and activates the peptide receptor B (NPR-B) resulting in the inhibition of FGFR3 downstream signaling. This in turn triggers endochondral growth and skeletal overgrowth, as observed in both mice and humans overexpressing CNP. Overproduction of CNP in the cartilage or continuous delivery of CNP through intravenous (iv) infusion normalizes the dwarfism of achondroplasic mice, suggesting that administration of CNP at supraphysiological levels is a strategy for treating ACH.

The human prepro-CNP which comprises 126 amino acids is further cleaved by furin to yield CNP-53. The CNP-53 possesses biological activity but is typically processed by an unknown mechanism to the biologically active 22 amino acids form in circulation, i.e. CNP-22. The bioactivity of CNP is tightly regulated and its clearance from the plasma is very rapid. Therefore, given the short in vivo half-life of CNP (2 min after intravenous administration), its use as a therapeutic agent is challenging in a pediatric population because it would require continuous infusion.

Various approaches for increasing the in vivo half-life of CNP were explored. For instance, Lorget et al. (Am. J. Hum. Genet. 91, 1108-1114, 2012) discloses a recombinant CNP-39 (also known as BMN111), consisting of the 37 C-terminal amino acids of human CNP-53 plus glycine and proline added at the N-terminus of the peptide, that mimics the pharmacological activity of human CNP. Although BMN111 is more resistant to NEP cleavage, it only has a half-life of 20 minutes, and thus when dosed daily is associated with a short duration of exposure to efficacious drug levels.

An expansion of the scope of increasing the in vivo half-life of CNP based on conjugation to water-soluble carrier moieties such as PEG, via reversible prodrug linkers was explored in WO2016/110577A1, WO2017/118693A1, WO2017/118698A1, WO2017/118700A1, WO2017/118703 A1, WO 2017/118704A1 and WO2017/118707A1. However, no information regarding formulations that allow for stable storage of these reversible conjugates is provided.

Pharmaceutical formulations of such CNP conjugates, wherein the polymer is attached to CNP via a reversible linkage, have to provide for sufficient stability of the CNP conjugate in order to avoid premature CNP release during storage. In case the reversible linkage between the polymer and CNP is degraded during storage, the concentration of the readily available drug is increased, and this could lead to risk of overdosage upon administration, which may result in hypotension.

In addition, any drug released during storage is subject to rapid renal clearance upon application to a patient, and consequently the time for which the long-acting composition provides therapeutically relevant amounts of drug is reduced. This poses the risk of unmet medical needs.

Furthermore, it is known that CNP or its variants, conjugates or derivatives may undergo degradation reactions during storage which may result in the formation of impurities/peptide damage within the corresponding formulation, such as:

degradation products resulting from the oxidation of methionine (Met/M) residues, to methionine sulfoxide and methionine sulfone;

degradation products resulting from the isomerization of aspartic acid or aspartate residues (Asp/D), to isoaspartic acid or isoaspartate such as via a succinimide intermediate;

degradation products resulting from the deamidation of asparagine residues (Asn/N), to aspartic acid or aspartate and/or to isoaspartic acid or isoaspartate such as via a succinimide intermediate;

degradation products resulting from the deamidation of glutamine residues (Gln/Q), to glutamic acid or isoglutamic acid such as via a glutarimide intermediate;

degradation products resulting from the isomerization of glutamic acid or glutamate residues (Glu/E), to isoglutamic acid or isoglutamate via a glutarimide intermediate; and aggregates resulted from the aggregation of the peptide.

As the aforementioned degradation products or oligomers that may form during storage may impair the bioactivity of the CNP moiety, it is thus desirable to minimize their formation. Moreover, the reversible linkage between the CNP moiety and the polymeric moiety makes the storage of the pharmaceutical formulation comprising the CNP conjugates challenging.

It is therefore important to identify suitable formulations of CNP conjugates comprising CNP covalently linked via a reversible linker to a polymeric moiety, wherein the peptide will exhibit an acceptable impurity profile and limited premature CNP release even after extended storage.

It is thus an object of the present invention to at least partially overcome the shortcomings described above.

This object is achieved with a dry pharmaceutical formulation, wherein the dry pharmaceutical formulation comprises a CNP conjugate, a buffering agent, and a bulking agent and wherein the CNP conjugate comprises a CNP moiety that is covalently and reversibly conjugated to a polymeric moiety.

It was surprisingly found that the dry pharmaceutical formulation of the present invention allows for stable long-term storage.

Within the meaning of the present invention the terms are used as follows.

As used herein, the term "about" in combination with a numerical value is used to indicate a range ranging from and including the numerical value plus and minus no more than 10% of said numerical value, in certain embodiments, no more than 8% of said numerical value, in certain embodiments, no more than 5% of said numerical value and in certain embodiments, no more than 2% of said numerical value. For example, the phrase "about 200" is used to mean a range ranging from and including 200+/−10%, i.e. ranging from and including 180 to 220; in certain embodiments, 200+/−8%, i.e. ranging from and including 184 to 216; in certain embodiments, ranging from and including 200+/−5%, i.e. ranging from and including 190 to 210; and in certain embodiments 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "antimicrobial" refers to a chemical substance, such as a chemical substance that kills or inhibits the growth of microorganisms, such as bacteria, fungi, yeasts, protozoans, molds and/or destroys viruses.

As used herein, the term "anti-adsorption agents" refers to mainly ionic or non-ionic surfactants, proteins or soluble polymers used to coat or adsorb competitively to the inner surface of the container comprising the formulation. Chosen concentration and type of excipient depends on the effect to be avoided but typically a monolayer of surfactant is formed at the interface just above the critical micelle concentration (CMC).

As used herein, the term "bulking agent" refers to a chemical compound which provides structure to the dry or lyophilized formulation. Bulking agents are added to the formulation to increase the total mass of the dry or lyophilized formulation. In addition to providing a pharmaceutically acceptable formulation, bulking agents may also modify the collapse temperature in order to alter the lyophilization process conditions, and further enhance the peptide stability over long-term storage. Therefore, during the drying of an admixture comprising a bulking agent, the bulking agent may serve as a lyoprotectant. Upon reconstitution of a dry pharmaceutical formulation into a reconstituted pharmaceutical formulation, the bulking agent may serve as an isotonicity-adjusting agent.

As used herein, the term "buffer" or "buffering agent" refers to a chemical compound that maintains the pH in a desired range. Physiologically tolerated buffers are, for example, sodium phosphate, succinate, histidine, bicarbonate, citrate, acetate, sulfate, nitrate, chloride and pyruvate. Antacids such as $Mg(OH)_2$ or $ZnCO_3$ may be also used.

As used herein, the term "CNP" refers to all CNP polypeptides, in certain embodiments from mammalian species, such as from human and mammalian species, in particular from human and murine species, as well as their variants, analogs, orthologs, homologs and derivatives and fragments thereof, that are characterized by regulating the growth, proliferation and differentiation of cartilaginous growth plate chondrocytes. The term "CNP" also includes all CNP variants, analogs, orthologs, homologs, derivatives and fragments thereof. The CNP variants, analogs, orthologs, homologs, derivatives and fragments thereof as disclosed in WO 2009/067639 A2 and WO 2010/135541 A2 are herewith incorporated by reference.

As used herein, the term "CNP polypeptide variant" refers to a polypeptide from the same species that differs from a reference CNP polypeptide. Generally, differences are limited so that the amino acid sequence of the reference and the variant are closely similar overall and, in many regions, identical. In certain embodiments, CNP polypeptide variants are at least 70%, 80%, 90%, or 95% identical to a reference CNP polypeptide. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Such CNP polypeptide variants may be naturally occurring variants, such as naturally occurring allelic variants encoded by one of several alternate forms of a CNP occupying a given locus on a chromosome or an organism, or isoforms encoded by naturally occurring splice variants originating from a single primary transcript. Alternatively, a CNP polypeptide variant may be a variant that is not known to occur naturally and that can be made by mutagenesis techniques known in the art. It is known in the art that one or more amino acids may be deleted from the N-terminus or C-terminus of a bioactive peptide or protein without substantial loss of biological function. Such N- and/or C-terminal deletions are also encompassed by the term CNP polypeptide variant.

It is also recognized by one of ordinary skill in the art that some amino acid sequences of CNP polypeptides can be varied without significant effect on the structure or function of the peptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

As used herein, the term "CNP analog" refers to CNP of different and unrelated organisms which perform the same functions in each organism, but which did not originate from an ancestral structure that the organisms' ancestors had in common. Instead, analogous CNPs arose separately and then later evolved to perform the same or similar functions. In other words, analogous CNP polypeptides are polypeptides with quite different amino acid sequences that perform the same biological activity, namely regulating the growth, proliferation and differentiation of cartilaginous growth plate chondrocytes.

As used herein, the term "CNP ortholog" refers to CNP within two different species which sequences are related to each other via a common homologous CNP in an ancestral species, but which have evolved to become different from each other.

As used herein, the term "CNP homolog" refers to CNP of different organisms which perform the same functions in each organism and which originate from an ancestral structure that the organisms' ancestors had in common. In other words, homologous CNP polypeptides are polypeptides with quite similar amino acid sequences that perform the same biological activity, namely regulating the growth, proliferation and differentiation of cartilaginous growth plate chondrocytes. In certain embodiments, CNP polypeptide homologs may be defined as polypeptides exhibiting at least 40%, 50%, 60%, 70%, 80%, 90% or 95% identity to a reference CNP polypeptide.

Thus, a CNP polypeptide may be, for example: (i) one in which at least one of the amino acid residues is substituted with a conserved or non-conserved amino acid residue, in certain embodiments, a conserved amino acid residue, and such substituted amino acid residue may or may not be one encoded by the genetic code; and/or (ii) one in which at least one of the amino acid residues includes a substituent group; and/or (iii) one in which the CNP polypeptide is fused with another compound, such as a compound to increase the half-life of the polypeptide (for example, polyethylene glycol); and/or (iv) one in which additional amino acids are fused to the CNP polypeptide, such as an IgG Fc fusion region peptide or leader or secretory sequence or a sequence which is employed for purification of the above form of the polypeptide or a pre-protein sequence.

As used herein, the term "CNP polypeptide fragment" refers to any peptide comprising a continuous span of a part of the amino acid sequence of a CNP polypeptide.

More specifically, a CNP polypeptide fragment comprises at least 6, such as at least 8, at least 10 or at least 17 consecutive amino acids of a CNP polypeptide. A CNP polypeptide fragment may additionally be described as sub-genuses of CNP polypeptides comprising at least 6 amino acids, wherein "at least 6" is defined as any integer between 6 and the integer representing the C-terminal amino acid of a CNP polypeptide. Further included are species of CNP polypeptide fragments at least 6 amino acids in length, as described above, that are further specified in terms of their N-terminal and C-terminal positions. Also encompassed by the term "CNP polypeptide fragment" as individual species are all CNP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a CNP polypeptide.

As the term CNP includes the above-described variants, analogs, orthologs, homologs, derivatives and fragments of CNP, all references to specific positions within a reference sequence also include the equivalent positions in the variants, analogs, orthologs, homologs, derivatives and fragments of a CNP moiety, even if not explicitly mentioned.

Naturally occurring CNP-22 (SEQ ID NO:1) has the following sequence:

GLSKGCFGLKLDRIGSMSGLGC, wherein the cysteines at position 6 and 22 are connected through a disulfide-bridge.

In certain embodiments, the term "CNP" also refers to the following peptide sequences:

(CNP-53):
SEQ ID NO: 2
DLRVDTKSRAAWARLLQEHPNARKYKGANKKGLSKGCFGLKLDRIGSMSGLGC;

(G-CNP-53):
SEQ ID NO: 3
GDLRVDTKSRAAWARLLQEHPNARKYKGANKKGLSKGCFGLKLDRIGSMSGLGC;

(M-CNP-53):
SEQ ID NO: 4
MDLRVDTKSRAAWARLLQEHPNARKYKGANKKGLSKGCFGLKLDRIGSMSGLGC;

(P-CNP-53):
SEQ ID NO: 5
PDLRVDTKSRAAWARLLQEHPNARKYKGANKKGLSKGCFGLKLDRIGSMSGLGC;

(CNP-53 M48N):
SEQ ID NO: 6
DLRVDTKSRAAWARLLQEHPNARKYKGANKKGLSKGCFGLKLDRIGSNSGLGC;

(CNP-53 Δ15-31):
SEQ ID NO: 7
DLRVDTKSRAAWARGLSKGCFGLKLDRIGSMSGLGC;

(CNP-52):
SEQ ID NO: 8
LRVDTKSRAAWARLLQEHPNARKYKGANKKGLSKGCFGLKLDRIGSMSGLGC;

(CNP-51):
SEQ ID NO: 9
RVDTKSRAAWARLLQEHPNARKYKGANKKGLSKGCFGLKLDRIGSMSGLGC;

(CNP-50):
SEQ ID NO: 10
VDTKSRAAWARLLQEHPNARKYKGANKKGLSKGCFGLKLDRIGSMSGLGC;

(CNP-49):
SEQ ID NO: 11
DTKSRAAWARLLQEHPNARKYKGANKKGLSKGCFGLKLDRIGSMSGLGC;

(CNP-48):
SEQ ID NO: 12
TKSRAAWARLLQEHPNARKYKGANKKGLSKGCFGLKLDRIGSMSGLGC;

(CNP-47):
SEQ ID NO: 13
KSRAAWARLLQEHPNARKYKGANKKGLSKGCFGLKLDRIGSMSGLGC;

(CNP-46):
SEQ ID NO: 14
SRAAWARLLQEHPNARKYKGANKKGLSKGCFGLKLDRIGSMSGLGC;

(CNP-45):
SEQ ID NO: 15
RAAWARLLQEHPNARKYKGANKKGLSKGCFGLKLDRIGSMSGLGC;

(CNP-44):
SEQ ID NO: 16
AAWARLLQEHPNARKYKGANKKGLSKGCFGLKLDRIGSMSGLGC;

(CNP-44 Δ14-22):
SEQ ID NO: 17
AAWARLLQEHPNAGLSKGCFGLKLDRIGSMSGLGC;

(CNP-44 Δ15-22):
SEQ ID NO: 18
AAWARLLQEHPNARGLSKGCFGLKLDRIGSMSGLGC;

(CNP-43):
SEQ ID NO: 19
AWARLLQEHPNARKYKGANKKGLSKGCFGLKLDRIGSMSGLGC;

(CNP-42):
SEQ ID NO: 20
WARLLQEHPNARKYKGANKKGLSKGCFGLKLDRIGSMSGLGC;

(CNP-41):
SEQ ID NO: 21
ARLLQEHPNARKYKGANKKGLSKGCFGLKLDRIGSMSGLGC;

(CNP-40):

SEQ ID NO: 22
RLLQEHPNARKYKGANKKGLSKGCFGLKLDRIGSMSGLGC;

(CNP-39):

SEQ ID NO: 23
LLQEHPNARKYKGANKKGLSKGCFGLKLDRIGSMSGLGC;

(CNP-38):

SEQ ID NO: 24
LQEHPNARKYKGANKKGLSKGCFGLKLDRIGSMSGLGC, wherein the cysteines at position 22 and 38 are connected through a disulfide-bridge;

SEQ ID NO: 25 (CNP-37):
QEHPNARKYKGANKKGLSKGCFGLKLDRIGSMSGLGC;

SEQ ID NO: 26 (CNP-37 Q1pQ, wherein pQ = pyroglutamate):
pQEHPNARKYKGANKKGLSKGCFGLKLDRIGSMSGLGC;

SEQ ID NO: 27 (G-CNP-37):
GQEHPNARKYKGANKKGLSKGCFGLKLDRIGSMSGLGC;

SEQ ID NO: 28 (P-CNP-37):
PQEHPNARKYKGANKKGLSKGCFGLKLDRIGSMSGLGC;

SEQ ID NO: 29 (M-CNP-37):
MQEHPNARKYKGANKKGLSKGCFGLKLDRIGSMSGLGC;

SEQ ID NO: 30 (PG-CNP-37):
PGQEHPNARKYKGANKKGLSKGCFGLKLDRIGSMSGLGC;

SEQ ID NO: 31 (MG-CNP-37):
MGQEHPNARKYKGANKKGLSKGCFGLKLDRIGSMSGLGC;

SEQ ID NO: 32 (CNP-37 M32N):
QEHPNARKYKGANKKGLSKGCFGLKLDRIGSNSGLGC;

SEQ ID NO: 33 (G-CNP-37 M32N):
GQEHPNARKYKGANKKGLSKGCFGLKLDRIGSNSGLGC;

SEQ ID NO: 34 (G-CNP-37 K14Q):
GQEHPNARKYKGANQKGLSKGCFGLKLDRIGSMSGLGC;

SEQ ID NO: 35 (G-CNP-37 K14P):
GQEHPNARKYKGANPKGLSKGCFGLKLDRIGSMSGLGC;

SEQ ID NO: 36 (G-CNP-37 K14Q, Δ15):
GQEHPNARKYKGANQGLSKGCFGLKLDRIGSMSGLGC;

SEQ ID NO: 37 (G-CNP-37 K14Q, K15Q):
GQEHPNARKYKGANQQGLSKGCFGLKLDRIGSMSGLGC;

SEQ ID NO: 38 (CNP-36):
EHPNARKYKGANKKGLSKGCFGLKLDRIGSMSGLGC;

SEQ ID NO: 39 (CNP-35):
HPNARKYKGANKKGLSKGCFGLKLDRIGSMSGLGC;

SEQ ID NO: 40 (CNP-34):
PNARKYKGANKKGLSKGCFGLKLDRIGSMSGLGC;

SEQ ID NO: 41 (CNP-33):
NARKYKGANKKGLSKGCFGLKLDRIGSMSGLGC;

SEQ ID NO: 42 (CNP-32):
ARKYKGANKKGLSKGCFGLKLDRIGSMSGLGC;

SEQ ID NO: 43 (CNP-31):
RKYKGANKKGLSKGCFGLKLDRIGSMSGLGC;

SEQ ID NO: 44 (CNP-30):
KYKGANKKGLSKGCFGLKLDRIGSMSGLGC;

SEQ ID NO: 45 (CNP-29):
YKGANKKGLSKGCFGLKLDRIGSMSGLGC;

SEQ ID NO: 46 (CNP-28):
KGANKKGLSKGCFGLKLDRIGSMSGLGC;

SEQ ID NO: 47 (GHKSEVAHRF-CNP-28):
GHKSEVAHRFKGANKKGLSKGCFGLKLDRIGSMSGLGC;

SEQ ID NO: 48 (CNP-27):
GANKKGLSKGCFGLKLDRIGSMSGLGC;

SEQ ID NO: 49 (CNP-27 K4Q, K5Q):
GANQQGLSKGCFGLKLDRIGSMSGLGC;

SEQ ID NO: 50 (CNP-27 K4R, K5R):
GANRRGLSKGCFGLKLDRIGSMSGLGC;

SEQ ID NO: 51 (CNP-27 K4P, K5R):
GANPRGLSKGCFGLKLDRIGSMSGLGC;

SEQ ID NO: 52 (CNP-27 K4S, K5S):
GANSSGLSKGCFGLKLDRIGSMSGLGC;

SEQ ID NO: 53 (CNP-27 K4P, K5R):
GANGANPRGLSRGCFGLKLDRIGSMSGLGC;

SEQ ID NO: 54 (CNP-27 K4R, K5R, K9R):
GANRRGLSRGCFGLKLDRIGSMSGLGC;

SEQ ID NO: 55 (CNP-27 K4R, K5R, K9R, M22N):
GANRRGLSRGCFGLKLDRIGSNSGLGC;

SEQ ID NO: 56 (P-CNP-27 K4R, K5R, K9R):
PGANRRGLSRGCFGLKLDRIGSMSGLGC;

SEQ ID NO: 57 (M-CNP-27 K4R, K5R, K9R):
MGANRRGLSRGCFGLKLDRIGSMSGLGC;

SEQ ID NO: 58 (HSA fragment-CNP-27):
GHKSEVAHRFKGANKKGLSKGCFGLKLDRIGSMSGLG;

SEQ ID NO: 59 (HSA fragment-CNP-27 M22N):
GHKSEVAHRFKGANKKGLSKGCFGLKLDRIGSNSGLGC;

SEQ ID NO: 60 (M-HSA fragment-CNP-27):
MGHKSEVAHRFKGANKKGLSKGCFGLKLDRIGSMSGLGC;

SEQ ID NO: 61 (P-HSA fragment-CNP-27):
PGHKSEVAHRFKGANKKGLSKGCFGLKLDRIGSMSGLGC;

SEQ ID NO: 62 (CNP-26):
ANKKGLSKGCFGLKLDRIGSMSGLGC;

SEQ ID NO: 63 (CNP-25):
NKKGLSKGCFGLKLDRIGSMSGLGC;

SEQ ID NO: 64 (CNP-24):
KKGLSKGCFGLKLDRIGSMSGLGC;

SEQ ID NO: 65 (CNP-23):
KGLSKGCFGLKLDRIGSMSGLGC;

SEQ ID NO: 66 (R-CNP-22):
RGLSKGCFGLKLDRIGSMSGLGC;

SEQ ID NO: 67 (ER-CNP-22):
ERGLSKGCFGLKLDRIGSMSGLGC;

SEQ ID NO: 68 (R-CNP-22 K4R):
RGLSRGCFGLKLDRIGSMSGLGC;

SEQ ID NO: 69 (ER-CNP-22 4KR):
ERGLSRGCFGLKLDRIGSMSGLGC;

SEQ ID NO: 70 (RR-CNP-22):
RRGLSRGCFGLKLDRIGSMSGLGC;

SEQ ID NO: 71 (HRGP fragment-CNP-22):
GHHSHEQHPHGANQQGLSKGCFGLKLDRIGSMSGLGC;

SEQ ID NO: 72 (HRGP fragment-CNP-22):
GAHHPHEHDTHGANQQGLSKGCFGLKLDRIGSMSGLGC;

SEQ ID NO: 73 (HRGP fragment-CNP-22):
GHHSHEQHPHGANPRGLSKGCFGLKLDRIGSMSGLGC;

SEQ ID NO: 74 (IgG$_1$(F$_c$) fragment-CNP-22):
GQPREPQVYTLPPSGLSKGCFGLKLDRIGSMSGLGC;

SEQ ID NO: 75 (HSA fragment-CNP-22):
GQHKDDNPNLPRGANPRGLSKGCFGLKLDRIGSMSGLGC;

SEQ ID NO: 76 (HSA fragment-CNP-22):
GERAFKAWAVARLSQGLSKGCFGLKLDRIGSMSGLGC;

SEQ ID NO: 77 (osteocrin NPR C inhibitor
fragment-CNP22):
FGIPMDRIGRNPRGLSKGCFGLKLDRIGSMSGLGC;

SEQ ID NO: 78 (FGF2 heparin-binding domain
fragment-CNP22):
GKRTGQYKLGSKTGPGPKGLSKGCFGLKLDRIGSMSGLGC;

SEQ ID NO: 79 (IgG$_1$(F$_c$) fragment-CNP-22 K4R):
GQPREPQVYTGANQQGLSRGCFGLKLDRIGSMSGLGC;

SEQ ID NO: 80 (HSA fragment-CNP-22 K4R):
GVPQVSTSTGANQQGLSRGCFGLKLDRIGSMSGLGC;

SEQ ID NO: 81 (fibronectin fragment-CNP-22 K4R):
GQPSSSSQSTGANQQGLSRGCFGLKLDRIGSMSGLGC;

SEQ ID NO: 82 (fibronectin fragment-CNP-22 K4R):
GQTHSSGTQSGANQQGLSRGCFGLKLDRIGSMSGLGC;

SEQ ID NO: 83 (fibronectin fragment-CNP-22 K4R):
GSTGQWHSESGANQQGLSRGCFGLKLDRIGSMSGLGC;

SEQ ID NO: 84 (zinc finger fragment-CNP-22 K4R):
GSSSSSSSSSGANQQGLSRGCFGLKLDRIGSMSGLGC;

SEQ ID NO: 85 (CNP-21):
LSKGCFGLKLDRIGSMSGLGC;

SEQ ID NO: 86 (CNP-20):
SKGCFGLKLDRIGSMSGLGC;

SEQ ID NO: 87 (CNP-19):
KGCFGLKLDRIGSMSGLGC;

SEQ ID NO: 88 (CNP-18):
GCFGLKLDRIGSMSGLGC;

SEQ ID NO: 89 (CNP-17):
CFGLKLDRIGSMSGLGC;

SEQ ID NO: 90 (BNP fragment-CNP-17-BNP fragment):
SPKMVQGSGCFGLKLDRIGSMSGLGCKVLRRH;

SEQ ID NO: 91 (CNP-38 L1G):
GQEHPNARKYKGANKKGLSKGCFGLKLDRIGSMSGLGC;

SEQ ID NO: 92 (Ac-CNP-37; wherein Ac = acetyl):
Ac-QEHPNARKYKGANKKGLSKGCFGLKLDRIGSMSGLGC;

SEQ ID NO: 93:
QEHPNARX$_1$YX$_2$GANX$_3$X$_4$GLSX$_5$GCFGLX$_6$LDRIGSMSGLGC, wherein $X_1$, $X_2$, $X_3$, $X_4$, $X_5$ and $X_6$ are independently of each other selected from the group consisting of K, R, P, S and Q, with the provision that at least one of $X_1$, $X_2$, $X_3$, $X_4$, $X_5$ and $X_6$ is selected from the group consisting of R, P, S and Q; in certain embodiments, $X_1$, $X_2$, $X_3$, $X_4$, $X_5$ and $X_6$ are selected from the group consisting of K and R, with the provision that at least one of $X_1$, $X_2$, $X_3$, $X_4$, $X_5$ and $X_6$ is R;

SEQ ID NO: 94:
QEHPNARKYKGANX$_1$X$_2$GLSX$_3$GCFGLX$_4$LDRIGSMSGLGC, wherein $X_1$, $X_2$, $X_3$ and $X_4$ are independently of each other selected from the group consisting of K, R, P, S and Q, with the provision that at least one of $X_1$, $X_2$, $X_3$ and $X_4$ is selected from the group consisting of R, P, S and Q; in certain embodiments, $X_1$, $X_2$, $X_3$ and $X_4$ are selected from K and R, with the provision that at least one of $X_1$, $X_2$, $X_3$ and $X_4$ is R;

SEQ ID NO:95:
QEHPNARKYKGANX$_1$X$_2$GLSKGCFGLKLDRIGS-MSGLGC, wherein $X_1X_2$ are selected from the group consisting of KR, RK, KP, PK, SS, RS, SR, QK, QR, KQ, RQ, RR and QQ.

It is understood that also the equivalents of the cysteines in positions 22 and 38 of SEQ ID NO:24 are connected through a disulfide-bridge in SEQ ID NOs: 2 to 95.

The term "CNP" also includes poly(amino acid) conjugates which have a sequence as described above, but have a backbone that comprises both amide and non-amide linkages, such as ester linkages, like for example depsipeptides. Depsipeptides are chains of amino acid residues in which the backbone comprises both amide (peptide) and ester bonds. Accordingly, the term "side chain" as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides. In certain embodiments, the term "CNP" refers to polypeptides having a backbone formed through amide (peptide) bonds.

As used herein, the term "ring moiety" refers to the stretch of consecutive amino acid residues of the CNP drug or moiety that is located between two cysteine residues that form an intramolecular disulfide bridge or between homologous amino acid residues which are connected through a chemical linker. Preferably, the ring moiety is located between two cysteine residues that form an intramolecular disulfide bridge. These two cysteines correspond to the cysteines at position 22 and position 38 in the sequence of CNP-38 (SEQ ID NO:24). Accordingly, amino acids 23 to 37 are located in said ring moiety, if the CNP drug or moiety has the sequence of CNP-38.

Independently of the length of the CNP moiety, the sequence of the ring moiety of wild-type CNP is FGLKL-DRIGSMSGLG (SEQ ID NO:96).

As the term CNP includes the above-described variants, analogs, orthologs, homologs, derivatives and fragments of CNP, the term "ring moiety" also includes the corresponding variants, analogs, orthologs, homologs, derivatives and fragments of the sequence of SEQ ID NO:96. Accordingly, all references to specific positions within a reference sequence also include the equivalent positions in variants, analogs, orthologs, homologs, derivatives and fragments of a CNP moiety, even if not explicitly mentioned.

As used herein, the term "cryoprotectant" refers to a chemical compound that is added to a formulation in order to protect the drug or drug conjugate during the freezing stages.

As used herein, the term "C$_{1-4}$ alkyl" alone or in combination means a straight-chain or branched alkyl moiety having 1 to 4 carbon atoms. If present at the end of a molecule, examples of straight-chain or branched C$_{1-4}$ alkyl are methyl, ethyl, n-propyl, isopropyl, n-butyl, isobutyl, sec-butyl and tert-butyl. When two moieties of a molecule are linked by the C$_{1-4}$ alkyl, then examples for such C$_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a C$_{1-4}$ alkyl carbon may optionally be replaced by a substituent as defined above. Optionally, a C$_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_3$-50 carbon may optionally be replaced by a substituent as defined above. Optionally, a $C_{1-10}$, $C_{1-20}$ alkyl or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH=CH_2$, —$CH=CH$—$CH_3$, —$CH_2$—$CH=CH_2$, —$CH=CHCH_2$—$CH_3$ and —$CH=CH$—$CH=CH_2$. When two moieties of a molecule are linked by the $C_{2-6}$ alkenyl group, then an example of such $C_{2-6}$ alkenyl is —$CH=CH$—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are —$C{\equiv}CH$, —$CH_2$—$C{\equiv}CH$, $CH_2$—$CH_2$—$C{\equiv}CH$ and $CH_2$—$C{\equiv}C$—$CH_3$. When two moieties of a molecule are linked by the alkynyl group, then an example is —$C{\equiv}C$—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which are in certain embodiments, selected from the group consisting of

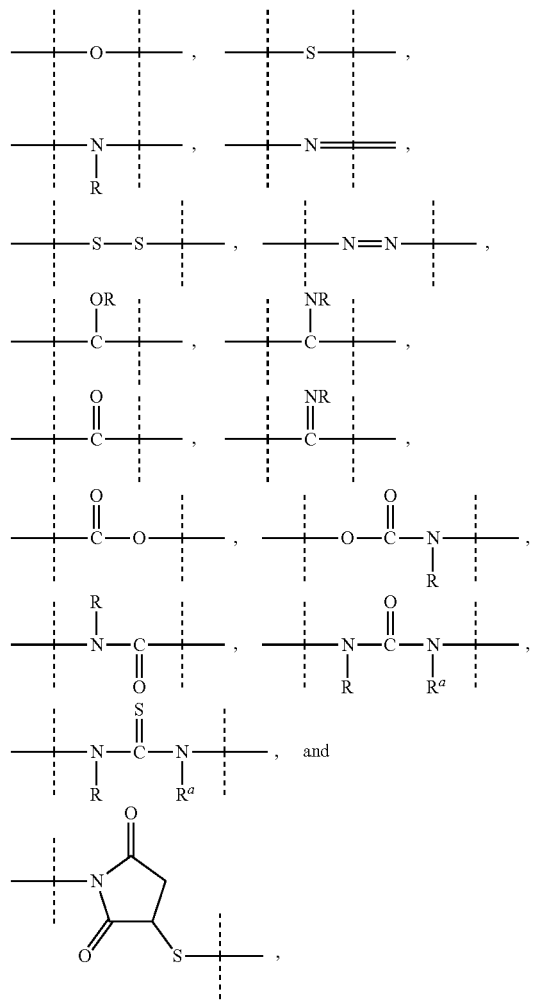

wherein
dashed lines indicate attachment to the remainder of the moiety or reagent; and
—R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

As used herein, the term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). In certain embodiments, an 8- to 30-membered carbopolycyclyl means a cyclic moiety of two, three, four or five rings, in certain embodiments of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropoly cycle" means a heterocyclic moiety of more than two rings with 8 to 30 ring atoms, in certain embodiments of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair R$^x$/R$^y$ is joined together with the atom to which they are attached to form a C$_{3-10}$ cycloalkyl or a 3- to 10-membered heterocyclyl" in relation with a moiety of the structure:

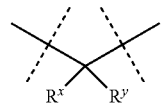

means that R$^x$ and R$^y$ form the following structure:

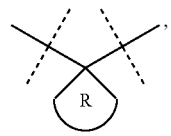

wherein R is C$_{3-10}$ cycloalkyl or 3- to 10-membered heterocyclyl.

It is also understood that the phrase "the pair R$^x$/R$^y$ is joined together with the atoms to which they are attached to form a ring A" in relation with a moiety of the structure:

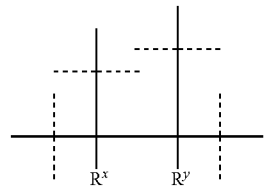

means that R$^x$ and R$^y$ form the following structure:

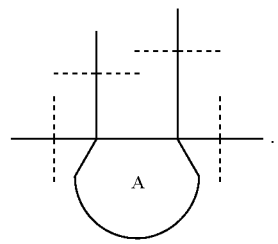

As used herein, the term "dry pharmaceutical formulation" means that a pharmaceutical formulation is provided in a dry form. Suitable methods for drying are spray-drying and lyophilization, i.e. freeze-drying. Such dry pharmaceutical formulations comprising CNP conjugates have a residual water content of a maximum of 10%, in certain embodiments less than 5% and in certain embodiments, less than 2%, as determined with Karl Fischer. In certain embodiments, the dry pharmaceutical formulation of the present invention is dried by lyophilization.

As used herein, the term "drug" refers to a substance used in the treatment, cure, prevention, or diagnosis of a disease or used to otherwise enhance physical or mental well-being. If a drug, such as CNP, is conjugated to another moiety, the moiety of the resulting product that originated from the drug is referred to as "drug moiety".

As used herein, the term "excipient" refers to compounds administered together with the drug or drug conjugate, for example, buffering agents, isotonicity modifiers, preservatives, stabilizers, anti-adsorption agents, oxidation protection agents, or other auxiliary agents. However, in some cases, one excipient may have dual or triple functions. The term "excipient" may also refer to a diluent, adjuvant, or vehicle with which the drug or drug conjugate, is administered. Such pharmaceutical excipient can be sterile liquids, such as water and oils, including those of petroleum, animal, vegetable or synthetic origin, including, but not limited to peanut oil, soybean oil, mineral oil, sesame oil and the like. Water is a preferred excipient when the pharmaceutical formulation is administered orally. Saline and aqueous dextrose are preferred excipients when the pharmaceutical formulation is administered intravenously or subcutaneously. Saline solutions and aqueous dextrose and glycerol solutions are in certain embodiments, employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical formulation can also contain minor amounts of wetting or emulsifying agents, pH buffering agents, like, for example, acetate, succinate, Tris (tris(hydroxymethyl)aminomethane), carbonate, phosphate, HEPES (4-(2-hydroxyethyl)-1-piperazineethanesulfonic acid), MES (2-(N-morpholino)ethanesulfonic acid), or can contain detergents, like Tween®, poloxamers, poloxamines, CHAPS, Igepal®, or amino acids like, for example, glycine, lysine, or histidine. These pharmaceutical formulations can take the form of solutions, suspensions, emulsions, tablets, pills, capsules, powders, sustained-release formulations and the like. The pharmaceutical formulation can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such formulations will contain a therapeutically effective amount of the drug or drug moiety, together with a suitable amount of excipient so as to provide the form for proper administration to the patient. The formulation should suit the mode of administration.

As used herein, the term "formulation" or "pharmaceutical formulation" refers to a formulation containing one or more CNP conjugates and one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. Accordingly, the pharmaceutical formulations of the present invention encompass any formulation or composition made by admixing one or more CNP conjugates and a pharmaceutically acceptable excipient such as a buffering agent and bulking agent.

As used herein, the term "free form" of a drug refers to the drug in its unmodified, pharmacologically fully active form, e.g. after being released from the conjugate.

As used herein, the term "functional group" means a group of atoms which can react with other groups of atoms. Functional groups include, but are not limited to, the following groups: carboxylic acid (—(C═O)OH), primary or secondary amine (—NH$_2$, —NH—), maleimide, thiol (—SH), sulfonic acid (—(O═S═O)OH), carbonate, carbamate (—O(C═O)N<), hydroxyl (—OH), aldehyde (—(C═O)H), ketone (—(C═O)—), hydrazine (>N—N<), isocyanate, isothiocyanate, phosphoric acid (—O(P═O)OHOH), phosphonic acid (—O(P═O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane and aziridine.

As used herein, the term "halogen" means fluoro, chloro, bromo or iodo. It is generally preferred that halogen is fluoro or chloro.

As used herein, the term "interrupted" means that a moiety is inserted in between two carbon atoms or—if the insertion is at one of the moiety's ends—between a carbon or heteroatom and a hydrogen atom, in certain embodiments between a carbon and a hydrogen atom.

As used herein, the term "isotonicity-adjusting agent" refers to a compound that minimizes pain, irritation and tissue damage that can result from cell damage due to osmotic pressure differences between the injected solution and plasma.

As used therein, the term "lyophilized formulation" means that the formulation comprising the CNP conjugate was first frozen and subsequently subjected to water removal by means of reduced pressure. This terminology does not exclude additional drying steps which occur in the manufacturing process prior to filling the formulation into the final container.

As used herein, the terms "lyophilization" or "freeze-drying" are interchangeable, and refer to a dehydration process, characterized by freezing a formulation and then reducing the surrounding pressure and, optionally, adding heat to allow the frozen water in the formulation to sublime directly from the solid phase to gas. Typically, the sublimed water is collected by desublimation.

As used herein, the term "lyoprotectant" is a molecule which, when combined with the active ingredient of interest, significantly prevents or reduces chemical and/or physical instability of the active ingredient upon drying in general and especially during lyophilization and subsequent storage. Exemplary lyoprotectants include sugars, such as sucrose or trehalose; amino acids such as monosodium glutamate or histidine or arginine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof. The lyoprotectant may also serve as a bulking agent in a dry pharmaceutical formulation and as an isotonicity-adjusting agent in a reconstituted pharmaceutical formulation.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each indicates attachment to another moiety. Accordingly, a drug moiety, such as a CNP moiety, is released from a conjugate as a drug, such as CNP.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—". Similarly, a moiety:

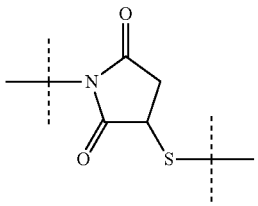

can be attached to two moieties or can interrupt a moiety either as:

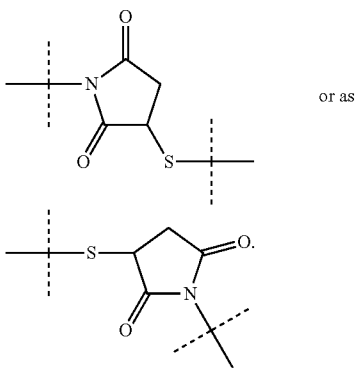

or as

In case the CNP moiety comprises one or more acidic or basic groups, the pharmaceutical formulation comprises also their corresponding pharmaceutically or toxicologically acceptable salts, in particular their pharmaceutically utilizable salts. Thus, the CNP moieties comprising one or more acidic groups can be present and used, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids, and other salts or amines known to the person skilled in the art. CNP moieties comprising one or more basic groups, i.e. groups which can be protonated, can be present and can be used in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively charged ammonium group and an appropriate counterion of the salt. If the CNP moieties simultaneously comprise acidic and basic groups, the pharmaceutical formulations according to the present invention also include, in addition to the salt forms mentioned, inner salts or betaines (zwitterions). The respective salts can be obtained by customary methods which are known to the person skilled in the art like, for example by contacting these conjugates with an organic or inorganic acid or base in a solvent or dispersant, or by anion exchange or cation exchange with other salts. The formulations according to the present invention also include all salts of the CNP conjugates which, owing to low physiological compatibility, are not directly suitable for use in pharmaceuticals but which can be used, for example, as intermediates for chemical reactions or for the preparation of pharmaceutically acceptable salts.

As used herein, the term "antioxidant" or "oxidation protection agent" refers to a compound which suppresses the oxidation of other compounds such as peptides.

As used herein, the term "pH-adjusting agent" refers to a chemical compound that is used to adjust the pH of the compounded solution prior to filling and lyophilization.

As used herein, the term "pharmaceutically acceptable" means a substance that does not cause harm when administered to a patient and preferably means approved by a regulatory agency, such as the EMA (Europe) and/or the FDA (US) and/or any other national regulatory agency for use in animals, preferably for use in humans.

As used herein, the term "physiological conditions" refers to an aqueous buffer at pH 7.4 and 37° C.

The term "polypeptide" as used herein refers to a chain of at least 2 and up to and including 50 amino acid monomer moieties linked by peptide (amide) linkages. Only for CNP drugs and CNP moieties also the sequences having more than 50 amino acids will be referred to as "polypeptide" for simplification.

As used herein, the term "preservative" refers to a chemical substance that has antimicrobial effects and prevents chemical degradation.

As used herein, the term "protein" refers to a chain of more than 50 amino acid monomer moieties linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. In certain embodiments, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, in certain embodiments it has a molecular weight of at most 1000 kDa, such as at most 750 kDa, such as at most 500 kDa, such as at most 300 kDa, such as at most 200 kDa, such as at most 100 kDa. It is understood that also a protein or a polypeptide is a polymer in which the amino acids are the repeating structural units, even though the side chains of each amino acid may be different.

As used herein, the term "polymeric" or "polymeric moiety" means a reagent or a moiety comprising one or more polymers or polymer moieties. A polymeric reagent or moiety may optionally also comprise one or more other moiety/moieties, which are in certain embodiments selected from the group consisting of:

C$_{1-50}$ alkyl, C$_{2-50}$ alkenyl, C$_{2-50}$ alkynyl, C$_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

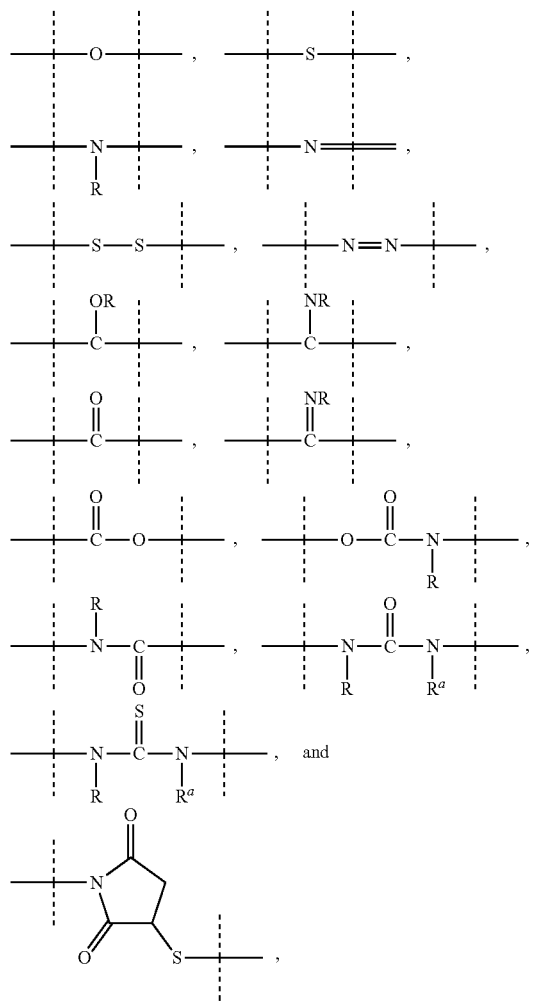

wherein
dashed lines indicate attachment to the remainder of the moiety or reagent, and
—R and —R$^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, in certain embodiments lies in a range of integers x+/−8%, in certain embodiments lies in a range of integers x+/−5% and in certain embodiments lies in a range of integers x+/−2%.

As used herein, the term "PEG-based" in relation to a moiety or reagent means that said moiety or reagent comprises PEG. In certain embodiments, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60% (w/w) PEG, such as at least 70% (w/w) PEG, such as at least 80% (w/w) PEG, such as at least 90% (w/w) PEG, such as at least 95% (w/w) PEG. The remaining weight percentage of the PEG-based moiety or reagent are other moieties selected from the following moieties and linkages:

C$_{1-50}$ alkyl, C$_{2-50}$ alkenyl, C$_{2-50}$ alkynyl, C$_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

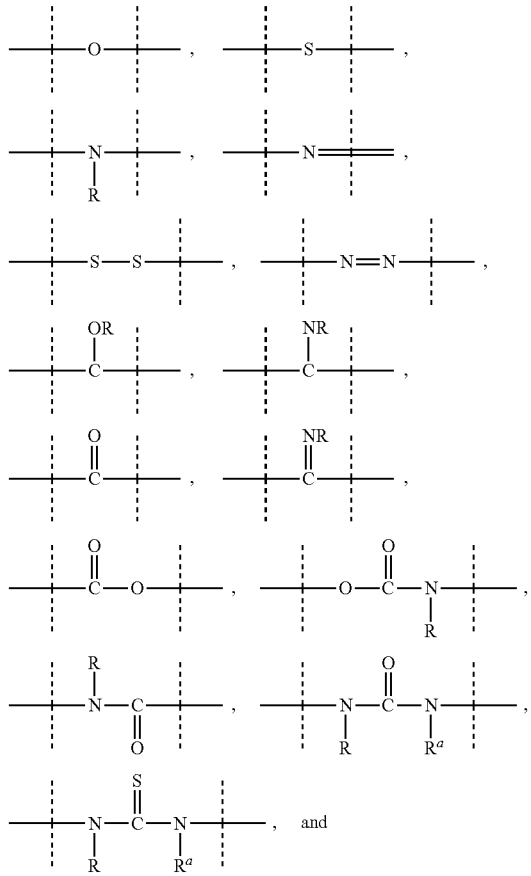

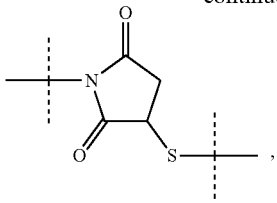

wherein
dashed lines indicate attachment to the remainder of the moiety or reagent, and
—R and —$R^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and in certain embodiments, all ethylene glycol units of said moiety or reagent are present in one block; the remaining weight percentage of the PEG-based moiety or reagent are other moieties in certain embodiments selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

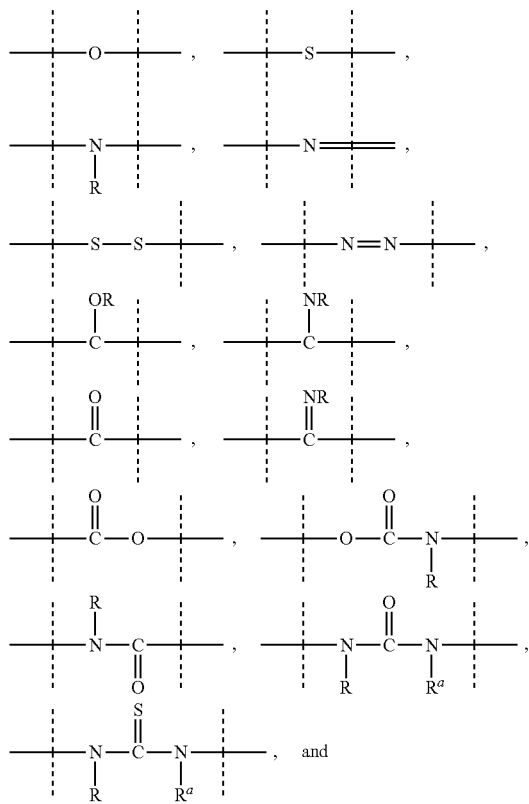

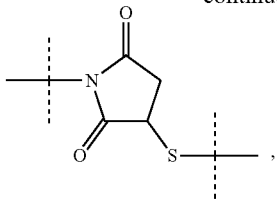

wherein
dashed lines indicate attachment to the remainder of the moiety or reagent, and
—R and —$R^a$ are independently of each other selected from the group consisting of —H, methyl, ethyl, propyl, butyl, pentyl and hexyl.

As used herein, the term "hyaluronic acid-based comprising at least X % hyaluronic acid" is used accordingly.

It is also recognized by one of ordinary skill in the art that the conjugates of the present invention are prodrugs. As used herein, the term "prodrug" refers to a drug moiety, such as a CNP moiety, reversibly and covalently conjugated to a polymeric moiety, such as —Z, through a reversible linker moiety. A prodrug releases the reversibly and covalently bound drug moiety in the form of its corresponding drug. In other words, a prodrug is a conjugate comprising a drug moiety, such as a CNP moiety, which is covalently and reversibly conjugated to a polymeric moiety via a reversible linker moiety, which covalent and reversible conjugation of the polymeric moiety to the reversible linker moiety is either direct or through a spacer. Such prodrugs or conjugates release the formerly conjugated drug moiety in the form of a free drug.

As used herein, the term "random coil" refers to a peptide or protein adopting/having/forming, in certain embodiments having, a conformation which substantially lacks a defined secondary and tertiary structure as determined by circular dichroism spectroscopy performed in aqueous buffer at ambient temperature, and pH 7.4. In certain embodiments, the ambient temperature is about 20° C., i.e. between 18° C. and 22° C., while in certain embodiments the ambient temperature is 20° C.

As used herein, the term "reversible linkage" is a linkage that is cleavable, in the absence of enzymes under physiological conditions (aqueous buffer at pH 7.4, 37° C.) with a half-life ranging from one hour to six months, such as from one hour to four months, such as from one hour to three months, from one hour to two months or from one hour to one month. Accordingly, a stable linkage is a linkage having a half-life under physiological conditions (aqueous buffer at pH 7.4, 37° C.) of more than six months.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "reversible linker moiety" is a moiety which is covalently conjugated to a drug moiety, such as a CNP moiety, through a reversible linkage and is also covalently conjugated to a polymeric moiety, such as —Z, wherein the covalent conjugation to said polymeric moiety is either direct or through a spacer moiety, such as -$L^2$-. In certain embodiments, the linkage between —Z and -$L^2$- is a stable linkage.

As used herein, the term "reconstitution" means the addition of a liquid to a dry pharmaceutical formulation in order to bring back the original form of a formulation, such as a solution.

As used herein, the term "reconstituted formulation" refers to the formulation obtained upon reconstitution of a dry pharmaceutical formulation by addition of a reconstitution solution.

As used herein, the term "reconstitution solution" refers to the liquid used to reconstitute the dry pharmaceutical formulation prior to administration to a patient in need thereof.

As used herein, the term "spacer" or "spacer moiety" refers to a moiety suitable for connecting two moieties. Suitable spacers may be selected from the group consisting of $C_{1-50}$ alkyl, $C_{2-50}$ alkenyl or $C_{2-50}$ alkynyl, which $C_{1-50}$ alkyl, $C_{2-50}$ alkenyl or $C_{2-50}$ alkynyl is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl and naphthyl.

As used herein, the term "substituted" means that one or more —H atom(s) of a molecule or moiety are replaced by a different atom or a group of atoms, which are referred to as "substituent".

In certain embodiments, such one or more substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and $C_{1-6}$ alkyl; wherein $C_{1-6}$ alkyl is optionally substituted with one or more halogen, which are the same or different.

In certain embodiments, the one or more substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-10}$ alkyl, $C_{2-10}$ alkenyl, and $C_{2-10}$ alkynyl; wherein -T$^0$, $C_{1-10}$ alkyl, $C_{2-10}$ alkenyl, and $C_{2-10}$ alkynyl are optionally substituted with one or more —R$^{x2}$, which are the same or different and wherein $C_{1-10}$ alkyl, $C_{2-10}$ alkenyl, and $C_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x3}$, —R$^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —R$^{x4}$, —R$^{x4a}$, —R$^{x4b}$ is independently selected from the group consisting of —H, halogen, $C_{1-6}$ alkyl, $C_{2-6}$ alkenyl, and $C_{2-6}$ alkynyl.

In certain embodiments, the one or more substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-6}$ alkyl, $C_{2-6}$ alkenyl, and $C_{2-6}$ alkynyl; wherein -T$^0$, $C_{1-6}$ alkyl, $C_{2-6}$ alkenyl, and $C_{2-6}$ alkynyl are optionally substituted with one or more —R$^{x2}$, which are the same or different and wherein $C_{1-6}$ alkyl, $C_{2-6}$ alkenyl, and $C_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x2}$, —R$^{x3}$, —R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different.

In certain embodiments, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "stable" and "stability" with regards to a pharmaceutical formulation means that after a storage time, such as after one month, two months, four months, six months, eight months, twelve months, eighteen months, twenty-four months, thirty-six months, forty-eight months, sixty months, in particular after the indicated storage time, the pharmaceutical formulation comprises less than 5% of the drug in its free form and less than 20%, such as less than 10% or such as less than 5% of impurities, such as impurities resulted from isomerization of aspartic acid or aspartate, oxidation of methionine and aggregation of the peptide. Impurities may be quantified by RP-HPLC or SEC based on their respective peak area relative to the total peak area of all CNP conjugate-related peaks in the chromatograms and impurities in the CNP moiety of the CNP conjugate may be determined by proteolytic digest and quantified as based on their respective peak area relative to the peak area of the corresponding unmodified proteolytic peptide.

As used herein, the term "stabilizer" refers to compounds used to stabilize the drug conjugate. Stabilization may be achieved by strengthening of the peptide-stabilizing forces or by direct binding of excipients to the drug conjugate.

As used herein, the term "surfactant" refers to wetting agents that lower the surface tension of a liquid.

As used herein, the term "sealing a container" means that the container is closed in such way that it is airtight, allowing no gas exchange between the outside and the inside and keeping the content sterile.

As used herein, the term "therapeutically effective amount" means an amount sufficient to cure, alleviate or partially arrest the clinical manifestations of a given disease and its complications. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician. Within the scope of this invention, therapeutically effective amount relates to dosages that aim to achieve therapeutic effect for an extended period of time, i.e. for at least one day, such as for two days, such as for three days, such as for four days, such as for five days, such as for six days, such as for one week or such as for two weeks.

As used herein, the term "traceless linker" means a reversible linker which upon cleavage releases the drug in its free form.

As used herein, the term "unit dose" means the amount of the drug administered to a patient in a single dose.

As used herein, the term "water-soluble" with reference to a polymeric moiety means that when such polymeric moiety is part of the CNP conjugate, at least 1 g of the CNP conjugate comprising such water-soluble polymeric moiety can be dissolved in one liter of water at 20° C. to form a homogeneous solution.

In general, the term "comprise" or "comprising" also encompasses "consist of" or "consisting of".

In certain embodiments, the CNP moiety of the CNP conjugate has the sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:30. In certain embodiments, the CNP moiety has the sequence of SEQ ID NO:20, SEQ ID NO:21, SEQ ID NO:22, SEQ ID NO:23, SEQ ID NO:24 or SEQ ID NO:25. In certain embodiments, the CNP moiety has the sequence of SEQ ID NO:20. In certain embodiments, the CNP moiety has the sequence of SEQ ID NO:21. In certain embodiments, the CNP moiety has the sequence of SEQ ID NO:22. In certain embodiments, the CNP moiety has the sequence of SEQ ID NO:23. In certain embodiments, the CNP moiety has the sequence of SEQ ID NO:24. In certain embodiments, the CNP moiety has the sequence of SEQ ID NO:25.

In certain embodiments the polymeric moiety is defined as variable —Z, which is described in more detail elsewhere herein.

The dry pharmaceutical formulation according to the present invention comprises a buffering agent. Exemplary buffering agents may be selected from the group consisting of succinic acid, citric acid, lactic acid, acetic acid, glutamic acid, fumaric acid, aspartic acid, glutaric acid, phosphoric acid, histidine, gluconic acid, tartaric acid, malic acid and mixtures thereof. It is clear to the person skilled in the art that the corresponding conjugate bases or salts of the buffering agents such as succinate, citrate, lactate, acetate, glutamate, fumarate, aspartate, glutarate, phosphate, gluconate, tartrate, malate and mixtures thereof, respectively, may also be included.

In certain embodiments, the buffering agent is succinic acid. In certain embodiments, the buffering agent is citric acid. In certain embodiments, the buffering agent is lactic acid. In certain embodiments, the buffering agent is acetic acid. In certain embodiments, the buffering agent is glutamic acid. In certain embodiments, the buffering agent is fumaric acid. In certain embodiments, the buffering agent is aspartic acid. In certain embodiments, the buffering agent is glutaric acid. In certain embodiments, the buffering agent is phosphoric acid. In certain embodiments, the buffering agent is histidine. In certain embodiments, the buffering agent is gluconic acid. In certain embodiments, the buffering agent is tartaric acid. In certain embodiments, the buffering agent is malic acid.

In certain embodiments, the buffering agent has a concentration from about 0.2% to about 3.2% (w/w). In certain embodiments, the buffering agent has a concentration from about 0.6% (w/w) to about 1.6% (w/w). In certain embodiments, the buffering agent has a concentration from about 0.9% to about 1.0% (w/w). In certain embodiments, the buffering agent has a concentration of about 1.0% (w/w).

The dry pharmaceutical formulation according to the present invention comprises a bulking agent.

The bulking agent may be selected from the group consisting of trehalose, mannitol, sucrose, raffinose, gelatin, lactose, dibasic calcium phosphate, sorbitol, xylitol, glycine, histidine, hydroxy ethyl starch, dextrose, dextran, Ficoll®, propylene glycol and mixtures thereof.

In certain embodiments, the bulking agent may be selected from the group consisting of trehalose, mannitol, sucrose, raffinose, gelatin, lactose, dibasic calcium phosphate, sorbitol, xylitol, glycine, histidine, hydroxy ethyl starch, dextrose, dextran, propylene glycol and mixtures thereof.

In certain embodiments, the bulking agent is selected from the group consisting of trehalose, sucrose and glycine.

In certain embodiments, the bulking agent is a non-reducing sugar such as trehalose or sucrose.

In certain embodiments, the bulking agent is trehalose. In certain embodiments, the bulking agent is mannitol. In certain embodiments, the bulking agent is sucrose. In certain embodiments, the bulking agent is raffinose. In certain embodiments, the bulking agent is gelatin. In certain embodiments, the bulking agent is lactose. In certain embodiments, the bulking agent is dibasic calcium phosphate. In certain embodiments, the bulking agent is sorbitol. In certain embodiments, the bulking agent is xylitol. In certain embodiments, the bulking agent is glycine. In certain embodiments, the bulking agent is histidine. In certain embodiments, the bulking agent is hydroxyethylstarch. In certain embodiments, the bulking agent is dextrose. In certain embodiments, the bulking agent is dextran. In certain embodiments, the bulking agent is Ficoll®. In certain embodiments, the bulking agent is propylene glycol.

As defined herein, the term "trehalose" in intended to encompass all salts and hydration states of trehalose, such as trehalose anhydrous or trehalose dihydrate. In certain embodiments, the term "trehalose" refers to trehalose anhydrous. In certain embodiments, the term "trehalose" refers to trehalose dihydrate.

In certain embodiments, the formulation may comprise multiple bulking agents.

In certain embodiments, reducing sugars should be avoided, as they may react with the CNP moiety. Accordingly, in certain embodiments the pharmaceutical formulation does not comprise a reducing sugar.

In certain embodiments, the bulking agent has a concentration ranging from about 52.6% to about 98.4% (w/w). In certain embodiments, the bulking agent has a concentration ranging from about 62.4% to about 70.4% (w/w). In certain embodiments, the bulking agent has a concentration ranging from about 85.7% to about 91.6% (w/w). In certain embodiments, the bulking agent has a concentration of about 65.2% (w/w).

The dry pharmaceutical formulation according to the present invention comprises a pH-adjusting agent. In certain embodiments, the pH-adjusting agent is an acid or acidic salt thereof. The acid may be selected from the group consisting of hydrochloric acid, phosphoric acid, carbonic acid, nitric acid and mixtures thereof.

In certain embodiments, the pH-adjusting agent is hydrochloric acid. In certain embodiments, the pH-adjusting agent is phosphoric acid. In certain embodiments, the pH-adjusting agent is carbonic acid. In certain embodiments, the pH-adjusting agent is nitric acid.

In certain embodiments, the pH-adjusting agent is a base or basic salt thereof. The base may be selected from the group consisting of Tris (tris(hydroxymethyl)aminomethane), sodium hydroxide, potassium hydroxide, lysine and mixtures thereof.

In certain embodiments, the pH-adjusting agent is Tris. In certain embodiments, the pH-adjusting agent is sodium hydroxide. In certain embodiments, the pH-adjusting agent is potassium hydroxide. In certain embodiments, the pH-adjusting agent is lysine.

In certain embodiments, the dry pharmaceutical formulation according to the present invention comprises a mixture of one or more acid and base pH-adjusting agents.

In certain embodiments, the pH-adjusting agent or mixture of pH-adjusting agents has a concentration from about 0.1% to about 5.6% (w/w). In certain embodiments, the pH-adjusting agent or mixture of pH-adjusting agents has a concentration from about 0.2% (w/w) to about 2.8% (w/w). In certain embodiments, the pH-adjusting agent or mixture of pH-adjusting agents has a concentration from about 0.5% to about 1.4% (w/w). In certain embodiments, the pH-adjusting agent or mixture of pH-adjusting agents has a concentration of about 1.2% (w/w). It is understood that in case of a mixture of pH-adjusting agents the provided concentrations refer to the total concentration of all pH-adjusting agents.

The dry pharmaceutical formulation of the present invention comprises a CNP conjugate.

In certain embodiments, the CNP conjugate has a concentration from about 23.8% to about 38.7% (w/w). In certain embodiments, the CNP conjugate has a concentration from about 5.8% (w/w) to about 12.4% (w/w). In certain embodiments, the CNP conjugate has a concentration from about 1.4% to about 3.7% (w/w).

In certain embodiments, the CNP conjugate is of formula (Ia) or (Ib)

wherein
-D is a CNP moiety;
-$L^1$- is a reversible linker moiety;
-$L^2$- is a single chemical bond or a spacer moiety;
—Z is a polymeric moiety;
x is an integer selected from the group consisting of 1, 2, 3, 4, 5, 6, 7, 8, 9, 10, 11, 12, 13, 14, 15 and 16; and
y is an integer selected from the group consisting of 1, 2, 3, 4 and 5.

-D of formula (Ia) or (Ib) is covalently and reversibly conjugated to -$L^1$-.

In certain embodiments, x of formula (Ia) is an integer selected from the group consisting of 1, 2, 3, 4, 6 and 8. In certain embodiments, x of formula (Ia) is an integer selected from the group consisting of 1, 2, 4 and 6. In certain embodiments, x of formula (Ia) is an integer selected from the group consisting of 1, 4 and 6 and in certain embodiments, x of formula (Ia) is 1.

In certain embodiments, y of formula (Ib) is an integer selected from the group consisting of 2, 3, 4 and 5. In certain embodiments, y of formula (Ib) is an integer selected from the group consisting of 2, 3 and 4. In certain embodiments, y of formula (Ib) is an integer selected from the group consisting of 2 and 3. In certain embodiments, y of formula (Ib) is an integer selected from the group consisting of 1, 2 and 3. In certain embodiments, y of formula (Ib) is 1. In certain embodiments, y of formula (Ib) is 2.

In certain embodiments, the CNP conjugate is of formula (Ia) with x=1.

In certain embodiments, -D of formula (Ia) or (Ib) has the sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:30. In certain embodiments, -D of formula (Ia) or (Ib) has the sequence of SEQ ID NO:20, SEQ ID NO:21, SEQ ID NO:22, SEQ ID NO:23, SEQ ID NO:24 or SEQ ID NO:25.

In certain embodiments, -D of formula (Ia) or (Ib) has the sequence of SEQ ID NO:20. In certain embodiments, -D of formula (Ia) or (Ib) has the sequence of SEQ ID NO:21. In certain embodiments, -D of formula (Ia) or (Ib) has the sequence of SEQ ID NO:22. In certain embodiments, -D of formula (Ia) or (Ib) has the sequence of SEQ ID NO:23. In certain embodiments, -D of formula (Ia) or (Ib) has the sequence of SEQ ID NO:24. In certain embodiments, -D of formula (Ia) or (Ib) has the sequence of SEQ ID NO:25.

The moiety -$L^1$- of formula (Ia) or (Ib) is either conjugated to a functional group of the side chain of an amino acid residue of -D, to the N-terminal amine functional group or to the C-terminal carboxyl functional group of -D or to a nitrogen atom in the backbone polypeptide chain of -D. Attachment to either the N-terminus or C-terminus can either be direct through the corresponding amine or carboxyl functional group, respectively, or indirect wherein a spacer moiety is first conjugated to the amine or carboxyl functional group to which spacer moiety -$L^1$- is conjugated.

The moiety -$L^1$- of formula (Ia) or (Ib) is a reversible linker from which the drug, i.e. D-H is released in its free form, i.e. -$L^1$- is a traceless linker. Suitable reversible linkers are known in the art, such as for example the reversible linker moieties disclosed in WO 2005/099768 A2, WO 2006/136586 A2, WO 2011/089216 A1 and WO 2013/024053 A1, which are incorporated by reference herewith.

In certain embodiments, -$L^1$- is a reversible linker as described in WO 2011/012722 A1, WO 2011/089214 A1, WO 2011/089215 A1, WO 2013/024052 A1 and WO 2013/160340 A1 which are incorporated by reference herewith.

The moiety -$L^1$- can be connected to -D through any type of linkage, provided that it is reversible. In certain embodiments, -$L^1$- is connected to -D through a linkage selected from the group consisting of amide, ester, carbamate, acetal, aminal, imine, oxime, hydrazone, disulfide and acylguanidine. In certain embodiments, -$L^1$- is connected to -D through a linkage selected from the group consisting of amide, ester, carbamate and acylguanidine. It is understood that these linkages may not per se be reversible, but that neighboring groups comprised in -$L^1$- may render the linkage reversible.

In certain embodiments, the moiety -$L^1$- is connected to -D through an amide linkage.

A moiety -$L^1$- is disclosed in WO 2009/095479 A2. Accordingly, in certain embodiments, the moiety -$L^1$- is of formula (II):

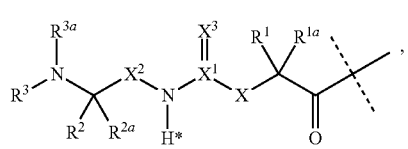
(II)

wherein the dashed line indicates the attachment to a nitrogen of -D which is a CNP moiety by forming an amide bond;

—X— is —C($R^4R^{4a}$)—; —N($R^4$)—; —O—; —C($R^4R^{4a}$)—C($R^5R^{5a}$)—; —C($R^5R^{5a}$)—C($R^4R^{4a}$)—; —C($R^4R^{4a}$)—N($R^6$)—; —N($R^6$)—C($R^4R^{4a}$)—; —C($R^4R^{4a}$)—O—; —O—C($R^4R^{4a}$)—; or —C($R^7R^{7a}$)—;

$X^1$ is C; or S(O);

—$X^2$— is —C($R^8R^{8a}$)—; or —C($R^8R^{8a}$)—C($R^9R^{9a}$)—;

=$X^3$ is =O; =S; or =N—CN;

—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H; and $C_{1-6}$ alkyl;

—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;

—$R^7$ is —N($R^{10}R^{10a}$); or —$NR^{10}$—(C=O)—$R^u$; —$R^{7a}$, —$R^{10}$, —$R^{10a}$, —$R^{11}$ are independently of each other —H; or $C_{1-6}$ alkyl;

optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/—$R^{9a}$ form a chemical bond;

optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;

optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring A;

optionally, $R^3$/$R^{3a}$ are joined together with the nitrogen atom to which they are attached to form a 3- to 10-membered heterocycle;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein -$L^1$- is substituted with -$L^2$-Z and wherein -$L^1$- is optionally further substituted, provided that the hydrogen marked with the asterisk in formula (II) is not replaced by -$L^2$-Z or a substituent;

wherein

-$L^2$- is a single chemical bond or a spacer; and

—Z is a water-soluble polymeric moiety;

In certain embodiments, -$L^1$- of formula (II) is substituted with one moiety -$L^2$-Z.

In certain embodiments, -$L^1$- of formula (II) is not further substituted.

It is understood that if —$R^3$/—$R^{3a}$ of formula (II) are joined together with the nitrogen atom to which they are attached to form a 3- to 10-membered heterocycle, only such 3- to 10-membered heterocycles, in which the atoms directly attached to the nitrogen are $sp^3$-hybridized carbon atoms may be formed. In other words, such 3- to 10-membered heterocycle formed by -$R^3$/—$R^{3a}$ together with the nitrogen atom to which they are attached has the following structure:

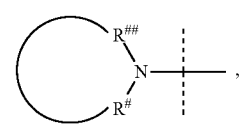

wherein
the dashed line indicates attachment to the rest of -L$^1$-;
the ring comprises 3 to 10 atoms comprising at least one nitrogen; and
R$^\#$ and R$^{\#\#\#}$ represent an sp$^3$-hydridized carbon atom.

It is also understood that the 3- to 10-membered heterocycle may be further substituted.

Exemplary embodiments of suitable 3- to 10-membered heterocycles formed by -R$^3$/—R$^{3a}$ of formula (II) together with the nitrogen atom to which they are attached are the following:

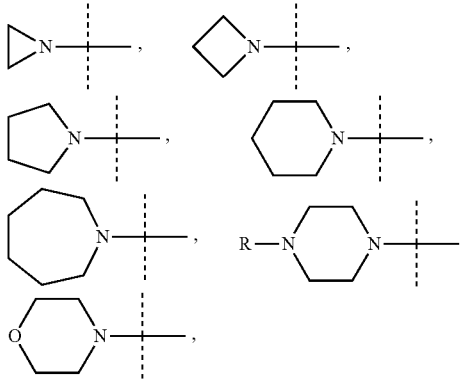

wherein
dashed lines indicate attachment to the rest of the molecule; and
—R is selected from the group consisting of —H and C$_{1-6}$ alkyl.

-L$^1$- of formula (II) may optionally be further substituted. In general, any substituent may be used as far as the cleavage principle is not affected, i.e. the hydrogen marked with the asterisk in formula (II) is not replaced and the nitrogen of the moiety

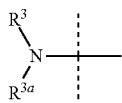

of formula (II) remains part of a primary, secondary or tertiary amine, i.e. —R$^3$ and —R$^{3a}$ are independently of each other —H or are connected to —N< through an sp$^3$-hybridized carbon atom.

In certain embodiments, —R$^1$ or —R$^{1a}$ of formula (II) is substituted with -L$^2$-Z. In certain embodiments, —R$^2$ or —R$^{2a}$ of formula (II) is substituted with -L$^2$-Z. In certain embodiments, —R$^3$ or —R$^{3a}$ of formula (II) is substituted with -L$^2$-Z. In certain embodiments, —R$^4$ of formula (II) is substituted with -L$^2$-Z. In certain embodiments, —R$^5$ or —R$^{5a}$ of formula (II) is substituted with -L$^2$-Z. In certain embodiments, —R$^6$ of formula (II) is substituted with -L$^2$-Z. In certain embodiments, —R$^7$ or —R$^{7a}$ of formula (II) is substituted with -L$^2$-Z. In certain embodiments, —R$^8$ or —R$^{8a}$ of formula (II) is substituted with -L$^2$-Z. In certain embodiments, —R$^9$ or —R$^{9a}$ of formula (II) is substituted with -L$^2$-Z.

In certain embodiments, —R$^4$ of formula (II) is substituted with -L$^2$-Z.

In certain embodiments, —X— of formula (II) is —C(R$^4$R$^{4a}$)— or —N(R$^4$)—.

In certain embodiments, —X— of formula (II) is —C(R$^4$R$^{4a}$)—.

In certain embodiments, X$^1$ of formula (II) is C.

In certain embodiments, =X$^3$ of formula (II) is =O.

In certain embodiments, —X$^2$— of formula (II) is —C(R$^8$R$^{8a}$)—.

In certain embodiments, —R$^8$ and —R$^{8a}$ of formula (II) are independently selected from the group consisting of —H, methyl and ethyl. In certain embodiments, at least one of —R$^8$ and —R$^{8a}$ of formula (II) is —H. In certain embodiments, both —R$^8$ and —R$^{8a}$ of formula (II) are —H.

In certain embodiments, —R$^1$ and —R$^{1a}$ of formula (II) are independently selected from the group consisting of —H, methyl and ethyl. In certain embodiments, at least one of —R$^1$ and —R$^{1a}$ of formula (II) is —H. In certain embodiments, both —R$^1$ and —R$^{1a}$ of formula (II) are —H.

In certain embodiments, —R$^2$ and —R$^{2a}$ of formula (II) are independently selected from the group consisting of —H, methyl and ethyl. In certain embodiments, at least one of —R$^2$ and —R$^{2a}$ of formula (II) is —H. In certain embodiments, both —R$^2$ and —R$^{2a}$ of formula (II) are H.

In certain embodiments, —R$^3$ and —R$^{3a}$ of formula (II) are independently selected from the group consisting of —H, methyl, ethyl, propyl and butyl. In certain embodiments, at least one of —R$^3$ and —R$^{3a}$ of formula (II) is methyl. In certain embodiments, —R$^3$ and —R$^{3a}$ of formula (II) are both —H. In certain embodiments, —R$^3$ and —R$^{3a}$ of formula (II) are both methyl. In certain embodiments, —R$^3$ of formula (II) is —H and —R$^{3a}$ of formula (II) is methyl.

In certain embodiments, —R$^4$ and —R$^{4a}$ of formula (II) are independently selected from the group consisting of —H, methyl and ethyl. In certain embodiments, at least one of —R$^4$ and —R$^{4a}$ of formula (II) is —H. In certain embodiments, both —R$^4$ and —R$^{4a}$ of formula (II) are —H.

In certain embodiments, the moiety -L$^1$- of formula (IIa):

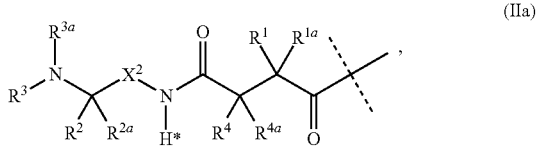

wherein the dashed line indicates the attachment to a nitrogen of -D which is a CNP moiety by forming an amide bond;
—R$^1$, —R$^{1a}$, —R$^2$, —R$^{2a}$, —R$^3$, —R$^{3a}$, —R$^4$, —R$^{4a}$ and —X$^2$— are used as defined in formula (II); and
wherein -L$^1$- is substituted with -L$^2$-Z and wherein -L$^1$- is optionally further substituted, provided that the hydrogen marked with the asterisk in formula (IIa) is not replaced by -L$^2$-Z or a substituent.

In certain embodiments, -L$^1$- of formula (IIa) is substituted with one moiety -L$^2$-Z.

In certain embodiments, the moiety -L$^1$- of formula (IIa) is not further substituted.

In certain embodiments, —R$^1$ and —R$^{1a}$ of formula (IIa) are independently selected from the group consisting of —H, methyl and ethyl. In certain embodiments, at least one of —R$^1$ and —R$^{1a}$ of formula (IIa) is —H. In certain embodiments, both —R$^1$ and —R$^{1a}$ of formula (IIa) are —H.

In certain embodiments, —R⁴ and —R⁴ᵃ of formula (IIa) are independently selected from the group consisting of —H, methyl and ethyl. In certain embodiments, at least one of —R⁴ and —R⁴ᵃ of formula (IIa) is —H. In certain embodiments, both —R⁴ and —R⁴ᵃ of formula (IIa) are —H.

In certain embodiments, —X²— of formula (IIa) is —C(R⁸R⁸ᵃ)—.

In certain embodiments, —R⁸ and —R⁸ᵃ of formula (IIa) are independently selected from the group consisting of —H, methyl and ethyl. In certain embodiments, at least one of —R⁸ and —R⁸ᵃ of formula (IIa) is —H. In certain embodiments, both —R⁸ and —R⁸ᵃ of formula (IIa) are —H.

In certain embodiments, —R² and —R²ᵃ of formula (IIa) are independently selected from the group consisting of —H, methyl and ethyl. In certain embodiments, at least one of —R² and —R²ᵃ of formula (IIa) is —H. In certain embodiments, both —R² and —R²ᵃ of formula (IIa) are H.

In certain embodiments, —R³ and —R³ᵃ of formula (IIa) are independently selected from the group consisting of —H, methyl, ethyl, propyl and butyl. In certain embodiments, at least one of —R³ and —R³ᵃ of formula (IIa) is methyl. In certain embodiments, —R³ and —R³ᵃ of formula (IIa) are both —H. In certain embodiments, —R³ and —R³ᵃ of formula (IIa) are both methyl. In certain embodiments, —R³ of formula (IIa) is —H and —R³ᵃ of formula (IIa) is methyl.

In certain embodiments, the moiety -L¹- is of formula (IIb):

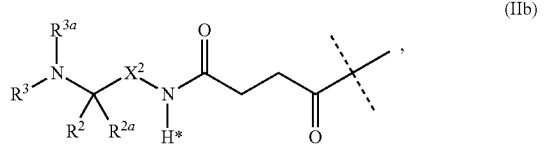

wherein the dashed line indicates the attachment to a nitrogen of -D which is a CNP moiety by forming an amide bond;
—R², —R²ᵃ, —R³, —R³ᵃ and —X²— are used as defined in formula (II); and
wherein -L¹- is substituted with -L²-Z and wherein -L¹- is optionally further substituted, provided that the hydrogen marked with the asterisk in formula (IIb) is not replaced by -L²-Z or a substituent.

In certain embodiments, -L¹- of formula (IIb) is substituted with one moiety -L²-Z.

In certain embodiments, the moiety -L¹- of formula (IIb) is not further substituted.

In certain embodiments, —X²— of formula (IIb) is —C(R⁸R⁸ᵃ)—.

In certain embodiments, —R⁸ and —R⁸ᵃ of formula (IIb) are independently selected from the group consisting of —H, methyl and ethyl. In certain embodiments, at least one of —R⁸ and —R⁸ᵃ of formula (IIb) is —H. In certain embodiments, both —R⁸ and —R⁸ᵃ of formula (IIb) are —H.

In certain embodiments, —R² and —R²ᵃ of formula (IIb) are independently selected from the group consisting of —H, methyl and ethyl. In certain embodiments, at least one of —R² and —R²ᵃ of formula (IIb) is —H. In certain embodiments, both —R² and —R²ᵃ of formula (IIb) are H.

In certain embodiments, —R³ and —R³ᵃ of formula (IIb) are independently selected from the group consisting of —H, methyl, ethyl, propyl and butyl. In certain embodiments, at least one of —R³ and —R³ᵃ of formula (IIb) is methyl. In certain embodiments, —R³ and —R³ᵃ of formula (IIb) are both —H. In certain embodiments, —R³ and —R³ᵃ of formula (IIb) are both methyl. In certain embodiments, —R³ of formula (IIb) is —H and —R³ᵃ of formula (IIb) is methyl.

In certain embodiments, the moiety -L¹- is of formula (IIb'):

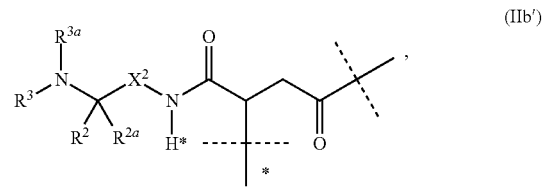

wherein
wherein the dashed line indicates the attachment to a nitrogen of -D which is a CNP moiety by forming an amide bond;
the dashed line marked with the asterisk indicates attachment to -L²-;
—R², —R²ᵃ, —R³, —R³ᵃ and —X²— are used as defined in formula (II); and
wherein -L¹- is optionally further substituted, provided that the hydrogen marked with the asterisk in formula (IIb') is not replaced by a substituent.

In certain embodiments, the moiety -L¹- of formula (IIb') is not further substituted.

In certain embodiments, —X²— of formula (IIb') is —C(R⁸R⁸ᵃ)—.

In certain embodiments, —R⁸ and —R⁸ᵃ of formula (IIb') are independently selected from the group consisting of —H, methyl and ethyl. In certain embodiments, at least one of —R⁸ and —R⁸ᵃ of formula (IIb') is —H. In certain embodiments, both —R⁸ and —R⁸ᵃ of formula (IIb') are —H.

In certain embodiments, —R² and —R²ᵃ of formula (IIb') are independently selected from the group consisting of —H, methyl and ethyl. In certain embodiments, at least one of —R² and —R²ᵃ of formula (IIb') is —H. In certain embodiments, both —R² and —R²ᵃ of formula (IIb') are H.

In certain embodiments, —R³ and —R³ᵃ of formula (IIb') are independently selected from the group consisting of —H, methyl, ethyl, propyl and butyl. In certain embodiments, at least one of —R³ and —R³ᵃ of formula (IIb') is methyl. In certain embodiments, —R³ and —R³ᵃ of formula (IIb') are both —H. In certain embodiments, —R³ and —R³ᵃ of formula (IIb') are both methyl. In certain embodiments, —R³ of formula (IIb') is —H and —R³ᵃ of formula (IIb') is methyl.

In certain embodiments, the moiety -L¹- is of formula (IIc):

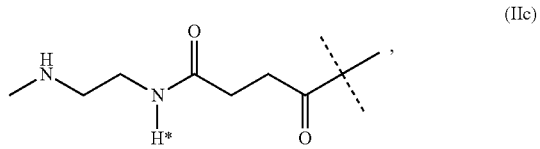

wherein the dashed line indicates the attachment to a nitrogen of -D which is a CNP moiety by forming an amide bond; and wherein -$L^1$- is substituted with -$L^2$-Z and wherein -$L^1$- is optionally further substituted, provided that the hydrogen marked with the asterisk in formula (IIc) is not replaced by -$L^2$-Z or a substituent.

In certain embodiments, -$L^1$- of formula (IIc) is substituted with one moiety -$L^2$-Z.

In certain embodiments, the moiety -$L^1$- of formula (IIc) is not further substituted.

In certain embodiments, the moiety -$L^1$- is of formula (IIc-a):

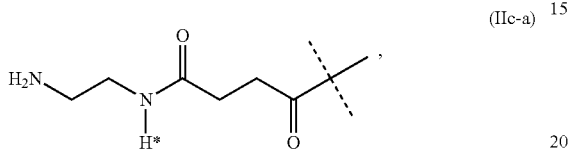

(IIc-a)

wherein the dashed line indicates the attachment to a nitrogen of -D which is a CNP moiety by forming an amide bond; and wherein -$L^1$- is substituted with -$L^2$-Z and wherein -$L^1$- is optionally further substituted, provided that the hydrogen marked with the asterisk in formula (IIc-a) is not replaced by -$L^2$-Z or a substituent.

In certain embodiments, -$L^1$- of formula (IIc-a) is substituted with one moiety -$L^2$-Z.

In certain embodiments, the moiety -$L^1$- of formula (IIc-a) is not further substituted.

In certain embodiments, the moiety -$L^1$- is of formula (IIc-b):

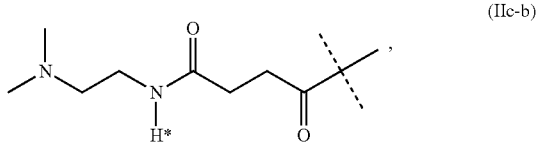

(IIc-b)

wherein the dashed line indicates the attachment to a nitrogen of -D which is a CNP moiety by forming an amide bond; and wherein -$L^1$- is substituted with -$L^2$-Z and wherein -$L^1$- is optionally further substituted, provided that the hydrogen marked with the asterisk in formula (IIc-b) is not replaced by -$L^2$-Z or a substituent.

In certain embodiments, -$L^1$- of formula (IIc-b) is substituted with one moiety -$L^2$-Z.

In certain embodiments, the moiety -$L^1$- of formula (IIc-b) is not further substituted.

In certain embodiments, the moiety -$L^1$- is selected from the group consisting of formula (IIc-i), (IIc-ii), (IIc-iii), (IIc-iv) and (IIc-v):

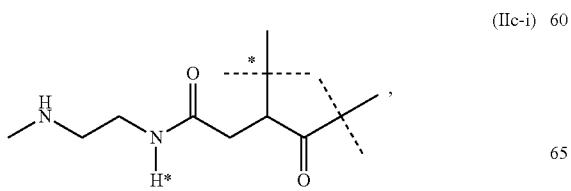

(IIc-i)

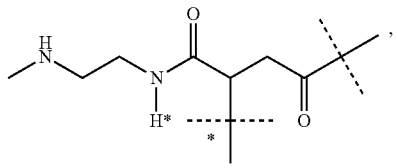

(IIc-ii)

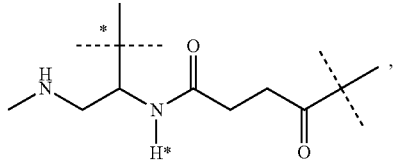

(IIc-iii)

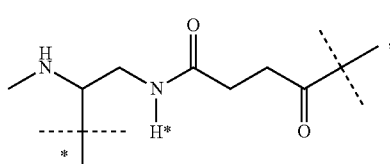

(IIc-iv)

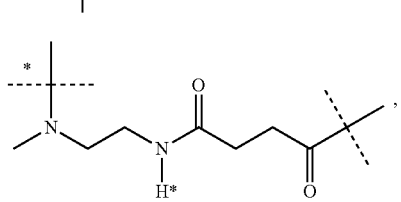

and (IIc-v)

wherein the unmarked dashed line indicates the attachment to a nitrogen of -D which is a CNP moiety by forming an amide bond; and the dashed line marked with the asterisk indicates attachment to -$L^2$-Z; and -$L^1$- is optionally further substituted, provided that the hydrogen marked with the asterisk in formula (IIc-i), (IIc-ii), (IIc-iii), (IIc-iv) and (IIc-v) is not replaced by a substituent.

In certain embodiments, the moiety -$L^1$- of formula (IIc-i), (IIc-ii), (IIc-iii), (IIc-iv) and (IIc-v) is not further substituted.

In certain embodiments, the moiety -$L^1$- is of formula (IIc-ii):

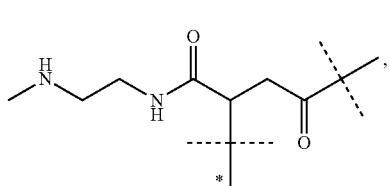

(IIc-ii)

wherein the unmarked dashed line indicates the attachment to a nitrogen of -D which is a CNP moiety by forming an amide bond; and the dashed line marked with the asterisk indicates attachment to -$L^2$-Z.

In certain embodiments, -$L^1$- of formula (IIc-ii) is substituted with one moiety -$L^2$-Z.

In certain embodiments, the moiety -$L^1$- is selected from the group consisting of formula (IIc-i'), (IIc-ii'), (IIc-iii'), (IIc-iv') and (IIc-v'):

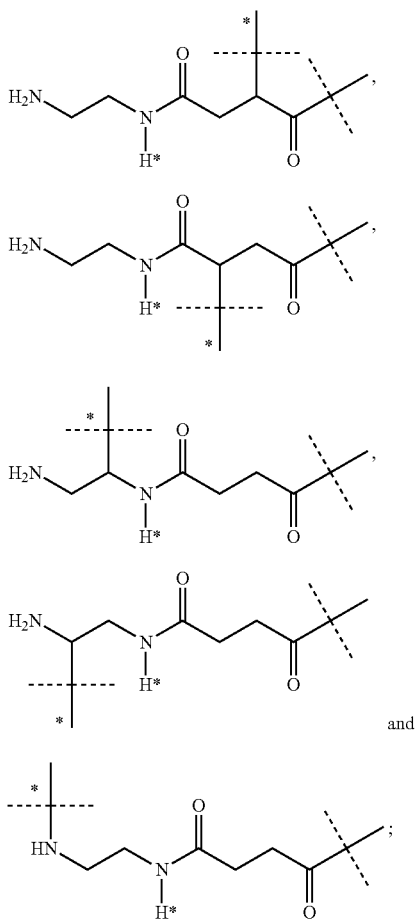

(IIc-i')

(IIc-ii')

(IIc-iii')

(IIc-iv')

and (IIc-v')

wherein
  the unmarked dashed line indicates the attachment to a nitrogen of -D which is a CNP moiety by forming an amide bond;
  the dashed line marked with the asterisk indicates attachment to -L²-Z; and
  -L¹- is optionally further substituted, provided that the hydrogen marked with the asterisk in formula (IIc-i'), (IIc-ii'), (IIc-iii'), (IIc-iv') and (IIc-v') is not replaced by a substituent.

In certain embodiments, the moiety -L¹- of formula (IIc-i'), (IIc-ii'), (IIc-iii'), (IIc-iv') and (IIc-v') is not further substituted.

In certain embodiments, the moiety -L¹- is of formula (IIc-ii'):

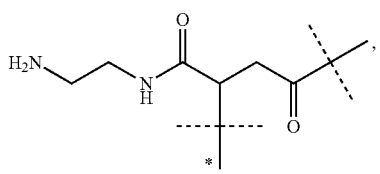

(IIc-ii')

wherein
  the unmarked dashed line indicates the attachment to a nitrogen of -D which is a CNP moiety by forming an amide bond; and
  the dashed line marked with the asterisk indicates attachment to -L²-Z.

In certain embodiments, -L¹- of formula (IIc-ii') is substituted with one moiety -L²-Z.

In certain embodiments, the moiety -L¹- is selected from the group consisting of formula (IIc-i"), (IIc-ii"), (IIc-iii") and (IIc-iv"):

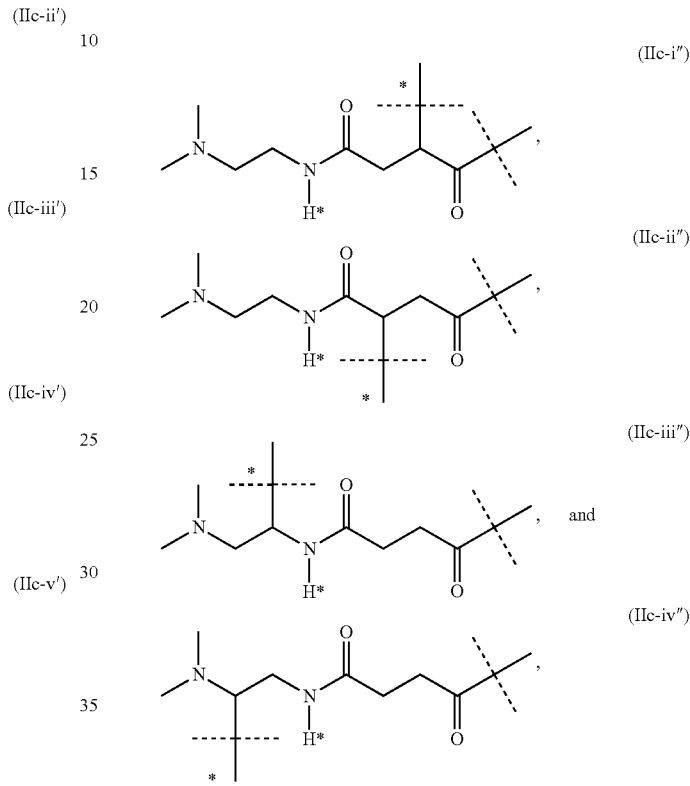

(IIc-i")

(IIc-ii")

(IIc-iii")

and (IIc-iv")

wherein
  the unmarked dashed line indicates the attachment to a nitrogen of -D which is a CNP moiety by forming an amide bond;
  the dashed line marked with the asterisk indicates attachment to -L²-Z; and
  -L¹- is optionally further substituted, provided that the hydrogen marked with the asterisk in formula (IIc-i"), (IIc-ii"), (IIc-iii") and (IIc-iv") is not replaced by a substituent.

In certain embodiments, the moiety -L¹- of formula (IIc-i"), (IIc-ii"), (IIc-iii") and (IIc-iv") is not further substituted.

In certain embodiments, the moiety -L¹- is of formula (IIc-ii"):

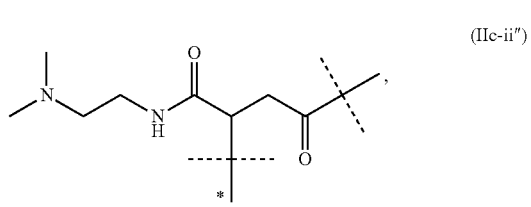

(IIc-ii")

wherein
the unmarked dashed line indicates the attachment to a nitrogen of -D which is a CNP moiety by forming an amide bond; and
the dashed line marked with the asterisk indicates attachment to -$L^2$-Z.

In certain embodiments, -$L^1$- of formula (IIc-ii″) is substituted with one moiety -$L^2$-Z.

The optional further substituents of -$L^1$- of formula (II), (IIa), (IIb), (IIb′), (IIe), (IIc-a), (IIc-b), (IIc-i), (IIc-ii), (IIc-iii), (IIc-iv), (IIc-v), (IIc-i′), (IIc-ii′), (IIc-iii′), (IIc-iv′), (IIc-v′), (IIc-i″), (IIc-ii″), (IIc-iii″) and (IIc-iv″) are in certain embodiments as described above.

Another moiety -$L^1$- is disclosed in WO2016/020373A1. Accordingly, in certain embodiments, the moiety -$L^1$- is of formula (III):

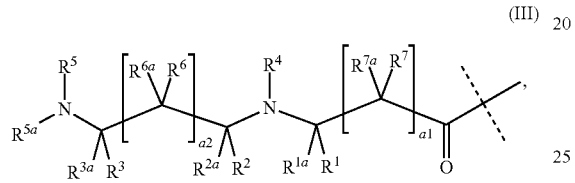

(III)

wherein
the dashed line indicates attachment to a primary or secondary amine or hydroxyl of -D which is a CNP moiety by forming an amide or ester linkage, respectively;
—$R^1$, —$R^{1a}$, —$R^2$, —$R^{2a}$, —$R^3$ and —$R^{3a}$ are independently of each other selected from the group consisting of —H, —C($R^8R^{8a}R^{8b}$), —C(=O)$R^8$, —C≡N, —C(=N$R^8$)$R^{8a}$, —C$R^8$(=C$R^{8a}R^{8b}$), —C≡C$R^8$ and -T;
$R^4$, —$R^5$ and —$R^{5a}$ are independently of each other selected from the group consisting of —H, —C($R^9R^{9a}R^{9b}$) and -T;
a1 and a2 are independently of each other 0 or 1;
each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —COO$R^{10}$, —O$R^{10}$, —C(O)$R^{10}$, —C(O)N($R^{10}R^{10a}$), —S(O)$_2$N($R^{10}R^{10a}$), —S(O)N($R^{10}R^{10a}$), —S(O)$_2R^{10}$, —S(O)$R^{10}$, —N($R^{10}$)S(O)$_2$N($R^{10a}R^{10b}$), —S$R^{10}$, —N($R^{10}R^{10a}$), —NO$_2$, —OC(O)$R^{10}$, —N($R^{10}$)C(O)$R^{10a}$, —N($R^{10}$)S(O)$_2R^{10a}$, —N($R^{10}$)S(O)$R^{10a}$, —N($R^{10}$)C(O)O$R^{10a}$, —N($R^{10}$)C(O)N($R^{10a}R^{10b}$), —OC(O)N($R^{10}R^{10a}$), -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;
each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;
each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;
each —$R^{11}$ is independently of each other selected from halogen, —CN, oxo (=O), —COO$R^{13}$, —O$R^{13}$, —C(O)$R^{13}$, —C(O)N($R^{13}R^{13a}$), —S(O)$_2$N($R^{13}R^{13a}$), —S(O)N($R^{13}R^{13a}$), —S(O)$_2R^{13}$, —S(O)$R^{13}$, —N($R^{13}$)S(O)$_2$N($R^{13a}R^{13b}$), —S$R^{13}$, —N($R^{13}R^{13a}$), —NO$_2$, —OC(O)$R^{13}$, —N($R^{13}$)C(O)$R^{13a}$, —N($R^{13}$)S(O)$_2R^{13a}$, —N($R^{13}$)S(O)$R^{13a}$, —N($R^{13}$)C(O)O$R^{13a}$, —N($R^{13}$)C(O)N($R^{13a}R^{13b}$), —OC(O)N($R^{13}R^{13a}$), and $C_{1-6}$ alkyl; wherein $C_{1-6}$ alkyl is optionally substituted with one or more halogen, which are the same or different;
each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;
optionally, one or more of the pairs —$R^1$/—$R^{1a}$, —$R^2$/—$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;
optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joined together with the atoms to which they are attached to form a ring A;
A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;
wherein -$L^1$- is substituted with -$L^2$-Z and wherein -$L^1$- is optionally further substituted;
wherein
-$L^2$- is a single chemical bond or a spacer; and
—Z is a water-soluble polymeric moiety.

The optional further substituents of -$L^1$- of formula (III) are in certain embodiments as described above.

In certain embodiments, -$L^1$- of formula (III) is substituted with one moiety -$L^2$-Z.

In certain embodiments, -$L^1$- of formula (III) is not further substituted.

Additional embodiments for -$L^1$- are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Additional embodiments for -$L^1$- are disclosed in U.S. Pat. No. 8,946,405B2 and U.S. Pat. No. 8,754,190B2, which are herewith incorporated by reference in their entirety. Accordingly, a moiety -$L^1$- is of formula (IV):

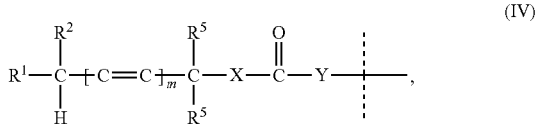

(IV)

wherein
the dashed line indicates attachment to -D which is a CNP moiety and wherein attachment is through a functional group of -D selected from the group consisting of —OH, —SH and —NH$_2$;
m is 0 or 1;
at least one or both of —R$^1$ and —R$^2$ is/are independently of each other selected from the group consisting of —CN, —NO$_2$, optionally substituted aryl, optionally substituted heteroaryl, optionally substituted alkenyl, optionally substituted alkynyl, —C(O)R$^3$, —S(O)R$^3$, —S(O)$_2$R$^3$, and —SR$^4$,
one and only one of —R$^1$ and —R$^2$ is selected from the group consisting of —H, optionally substituted alkyl, optionally substituted arylalkyl, and optionally substituted heteroarylalkyl;
—R$^3$ is selected from the group consisting of —H, optionally substituted alkyl, optionally substituted aryl, optionally substituted arylalkyl, optionally substituted heteroaryl, optionally substituted heteroarylalkyl, —OR$^9$ and —N(R$^9$)$_2$;
—R$^4$ is selected from the group consisting of optionally substituted alkyl, optionally substituted aryl, optionally substituted arylalkyl, optionally substituted heteroaryl, and optionally substituted heteroarylalkyl;
each —R$^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;
—R$^9$ is selected from the group consisting of —H and optionally substituted alkyl;
—Y— is absent and —X— is —O— or —S—; or
—Y— is —N(Q)CH$_2$— and —X— is —O—;
Q is selected from the group consisting of optionally substituted alkyl, optionally substituted aryl, optionally substituted arylalkyl, optionally substituted heteroaryl and optionally substituted heteroarylalkyl;
optionally, —R$^1$ and —R$^2$ may be joined to form a 3 to 8-membered ring; and
optionally, both —R$^9$ together with the nitrogen to which they are attached form a heterocyclic ring;
wherein -L$^1$- is substituted with -L$^2$-Z and wherein -L$^1$- is optionally further substituted;
wherein
-L$^2$- is a single chemical bond or a spacer; and
—Z is a water-soluble polymeric moiety.
The optional further substituents of -L$^1$- of formula (IV) are in certain embodiments, as described above.
In certain embodiments, -L$^1$- of formula (IV) is substituted with one moiety -L$^2$-Z.
In certain embodiments, -L$^1$- of formula (IV) is not further substituted.
Only in the context of formula (IV) the terms used have the following meaning:
The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.
The term "alkenyl" includes non-aromatic unsaturated hydrocarbons with carbon-carbon double bonds.
The term "alkynyl" includes non-aromatic unsaturated hydrocarbons with carbon-carbon triple bonds.
The term "aryl" includes aromatic hydrocarbon groups of 6 to 18 carbons, in certain embodiments, 6 to 10 carbons, including groups such as phenyl, naphthyl, and anthracenyl.
The term "heteroaryl" includes aromatic rings comprising 3 to 15 carbons containing at least one N, O or S atom, in certain embodiments, 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.
In certain embodiments, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.
The term "halogen" includes bromo, fluoro, chloro and iodo.
The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.
When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, —NR$_2$, —OCOR, —NRCOR, —COOR, —CONR$_2$, —SOR, —SO$_2$R, —SONR$_2$, —SO$_2$NR$_2$, wherein each R is independently alkyl, alkenyl, alkynyl, aryl or heteroaryl, or two R groups taken together with the atoms to which they are attached form a ring.
An additional embodiment for -L$^1$- is disclosed in WO2013/036857A1, which is herewith incorporated by reference in its entirety. Accordingly, in certain embodiments, moiety -L$^1$- is of formula (V):

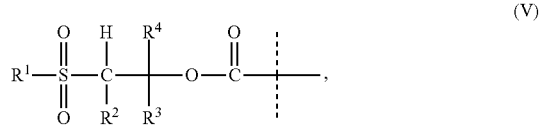

(V)

wherein
the dashed line indicates attachment to -D which is a CNP moiety and wherein attachment is through an amine functional group of -D;
—R$^1$ is selected from the group consisting of optionally substituted C$_1$-C$_6$ linear, branched, or cyclic alkyl; optionally substituted aryl; optionally substituted heteroaryl; alkoxy; and —NR$^5{}_2$;
—R$^2$ is selected from the group consisting of —H; optionally substituted C$_1$-C$_6$ alkyl; optionally substituted aryl; and optionally substituted heteroaryl;

—R³ is selected from the group consisting of —H; optionally substituted $C_1$-$C_6$ alkyl; optionally substituted aryl; and optionally substituted heteroaryl;

—R⁴ is selected from the group consisting of —H; optionally substituted $C_1$-$C_6$ alkyl; optionally substituted aryl; and optionally substituted heteroaryl;

each —R⁵ is independently of each other selected from the group consisting of —H; optionally substituted $C_1$-$C_6$ alkyl; optionally substituted aryl; and optionally substituted heteroaryl; or when taken together two —R⁵ can be cycloalkyl or cycloheteroalkyl;

wherein -L¹- is substituted with -L²-Z and wherein -L¹- is optionally further substituted;

wherein

-L²- is a single chemical bond or a spacer; and

—Z is a water-soluble polymeric.

The optional further substituents of -L¹- of formula (V) are, in certain embodiments as described above.

In certain embodiments, -L¹- of formula (V) is substituted with one moiety -L²-Z.

In certain embodiments, -L¹- of formula (V) is not further substituted.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, in certain embodiments, 6-10 carbons, including groups such as phenyl, naphthyl, and anthracene "Heteroaryl" includes aromatic rings comprising 3-15 carbons containing at least one N, O or S atom, in certain embodiments, 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketone; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

Another embodiment for -L¹- is disclosed in U.S. Pat. No. 7,585,837B2, which is herewith incorporated by reference in its entirety. Accordingly, in certain embodiments, a moiety -L¹- is of formula (VI):

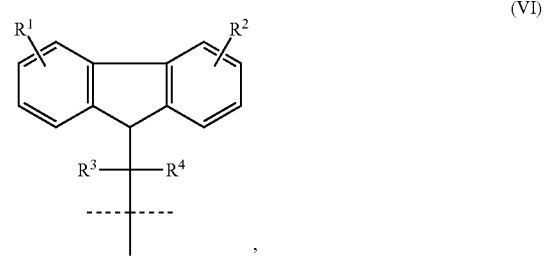

wherein the dashed line indicates attachment to -D which is a CNP moiety and wherein attachment is through an amine functional group of -D;

R¹ and R² are independently selected from the group consisting of hydrogen, alkyl, alkoxy, alkoxyalkyl, aryl, alkaryl, aralkyl, halogen, nitro, —SO₃H, —SO₂NHR⁵, amino, ammonium, carboxyl, PO₃H₂, and OPO₃H₂;

R³, R⁴, and R⁵ are independently selected from the group consisting of hydrogen, alkyl, and aryl;

wherein -L¹- is substituted with -L²-Z and wherein -L¹- is optionally further substituted;

wherein

-L²- is a single chemical bond or a spacer; and

—Z is a water-soluble polymeric moiety.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

In certain embodiments, -L¹- of formula (VI) is substituted with one moiety -L²-Z.

The optional further substituents of -L¹- of formula (VI) are in certain embodiments as described above.

In certain embodiments, -L¹- of formula (VI) is not further substituted.

Only in the context of formula (VI) the terms used have the following meaning:

The terms "alkyl", "alkoxy", "alkoxyalkyl", "aryl", "alkaryl" and "aralkyl" mean alkyl radicals of 1-8, in certain embodiments, 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

A further embodiment for -L¹- is disclosed in WO2002/089789A1, which is herewith incorporated by reference in its entirety. Accordingly, a moiety -L¹- is of formula (VII):

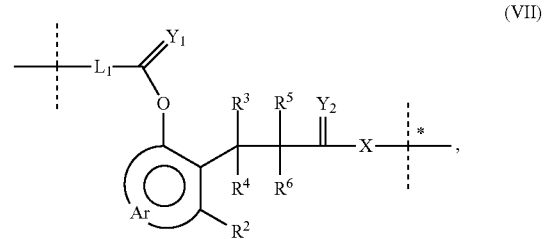

wherein the dashed line indicates attachment to -D which is a CNP moiety and wherein attachment is through an amine functional group of -D;

$L^1$ is a bifunctional linking group, $Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multi substituted aromatic hydrocarbon or a multi-substituted heterocyclic group;

X is a chemical bond or a moiety that is actively transported into a target cell, a hydrophobic moiety, or a combination thereof, y is 0 or 1;

wherein $-L^1-$ is substituted with $-L^2-Z$ and wherein $-L^1-$ is optionally further substituted;

wherein $-L^2-$ is a single chemical bond or a spacer; and

—Z is a water-soluble polymeric moiety.

In certain embodiments, $-L^1-$ of formula (VII) is substituted with one moiety $-L^2-Z$.

The optional further substituents of $-L^1-$ of formula (VII) are in certain embodiments, as described above.

In certain embodiments, $-L^1-$ of formula (VII) is not further substituted.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxy alkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieities such as methoxy; and phenoxy includes moieties such as 3-nitrophenoxy. Halo-shall be understood to include fluoro, chloro, iodo and bromo.

In certain embodiments, $-L^1-$ comprises a substructure of formula (VIII)

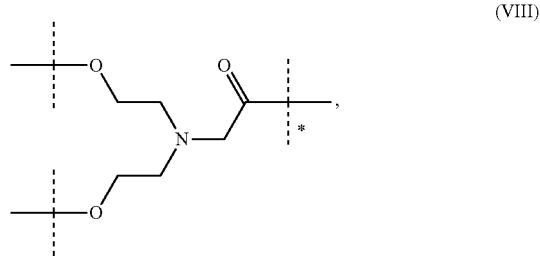

(VIII)

wherein the dashed line marked with the asterisk indicates attachment to a nitrogen of -D which is a CNP moiety by forming an amide bond;

the unmarked dashed lines indicate attachment to the remainder of $-L^1-$; and wherein $-L^1-$ is substituted with $-L^2-Z$ and wherein $-L^1-$ is optionally further substituted;

wherein $-L^2-$ is a single chemical bond or a spacer; and

—Z is a water-soluble polymeric moiety.

In certain embodiments, $-L^1-$ of formula (VIII) is substituted with one moiety $-L^2-Z$.

The optional further substituents of $-L^1-$ of formula (VIII) are as described above.

In certain embodiments, $-L^1-$ of formula (VIII) is not further substituted.

In certain embodiments, $-L^1-$ comprises a substructure of formula (IX):

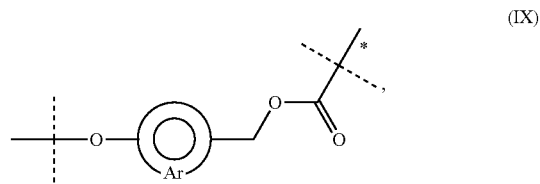

(IX)

wherein the dashed line marked with the asterisk indicates attachment to a nitrogen of -D which is a CNP moiety by forming a carbamate bond;

the unmarked dashed lines indicate attachment to the remainder of $-L^1-$; and wherein $-L^1-$ is substituted with $-L^2-Z$ and wherein $-L^1-$ is optionally further substituted;

wherein $-L^2-$ is a single chemical bond or a spacer; and

—Z is a water-soluble polymeric moiety.

The optional further substituents of $-L^1-$ of formula (IX) are as described above.

In certain embodiments, $-L^1-$ of formula (IX) is substituted with one moiety $-L^2-Z$.

In certain embodiments, $-L^1-$ of formula (IX) is not further substituted.

The moiety -D may be connected to $-L^1-$ through any functional group of D-H and is connected to $-L^1-$ through an amine functional group of D-H. This may be the N-terminal amine functional group or an amine functional group provided by a lysine side chain, i.e. by the lysines at position 9, 11, 15, 16, 20 and 26, if the CNP has the sequence of SEQ ID NO:24.

Attachment of $-L^1-$ to the ring of a CNP moiety significantly reduces the CNP conjugate's affinity to NPR-B compared to attachment at the N-terminus or to the non-ring part of CNP, which reduced affinity to NPR-B in turn reduces the risk of cardiovascular side effects, such as hypotension.

Accordingly, in certain embodiments, $-L^1-$ is conjugated to the side chain of an amino acid residue of said ring moiety of -D or to the backbone of said ring moiety of -D. In certain embodiments, $-L^1-$ is covalently and reversibly conjugated to the side chain of an amino acid residue of said ring moiety of -D. If -D is a CNP moiety with the sequence of SEQ ID NO:24, $-L^1-$ is, in certain embodiments, conjugated to the amine functional group provided by the lysine at position 26 of the corresponding drug D-H.

The moiety $-L^2-$ is a chemical bond or a spacer moiety.

In certain embodiments, $-L^2-$ is a chemical bond.

In certain embodiments, $-L^2-$ is a spacer moiety.

The moiety -L$^2$- can be attached to -L$^1$- by replacing any —H present, except where explicitly excluded.

When -L$^2$- is other than a single chemical bond, -L$^2$- is selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more —R$^{y2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

each —R$^{y2}$ is independently selected from the group consisting of halogen, —CN, oxo (═O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

When -L$^2$- is other than a single chemical bond, -L$^2$- is selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-20}$ alkyl, C$_{2-20}$ alkenyl, and C$_{2-20}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

—R$^{y2}$ is selected from the group consisting of halogen, —CN, oxo (═O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C (O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

When -L$^2$- is other than a single chemical bond, -L$^2$- is selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

In certain embodiments, -L$^2$- is a C$_{1-20}$ alkyl chain, which is optionally interrupted by one or more groups independently selected from —O—, -T- and —C(O)N(R$^{y1}$)—; and which C$_{1-20}$ alkyl chain is optionally substituted with one or more groups independently selected from —OH, -T and —C(O)N(R$^{y6}$R$^{y6a}$); wherein —R$^{y1}$, —R$^{y6}$, —R$^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

In certain embodiments, -L$^2$- has a molecular weight in the range of from 14 g/mol to 750 g/mol.

In certain embodiments, -L$^2$- has a chain length of 1 to 20 atoms.

As used herein, the term "chain length" with regard to the moiety -L$^2$- refers to the number of atoms of -L$^2$- present in the shortest connection between -L$^1$- and —Z.

In certain embodiments, -L$^2$- is of formula (i):

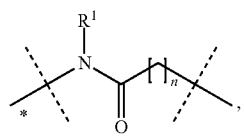

(i)

wherein
the dashed line marked with the asterisk indicates attachment to -L$^1$-;
the unmarked dashed line indicates attachment to —Z;
—R$^1$ is selected from the group consisting of —H, C$_{1-6}$ alkyl, C$_{2-6}$ alkenyl and C$_{2-6}$ alkynyl;
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

In certain embodiments, —R$^1$ of formula (i) is selected from the group consisting of —H, methyl, ethyl, propyl, and butyl. In certain embodiments, —R$^1$ of formula (i) is selected from the group consisting of —H, methyl, ethyl and propyl. In certain embodiments, —R$^1$ of formula (i) is selected from the group consisting of —H and methyl. In certain embodiments, —R$^1$ of formula (i) is methyl.

In certain embodiments, n of formula (i) is selected from the group consisting of 0, 1, 2, 3, 4, 5, 6, 7, 8, 9 and 10. In certain embodiments, n of formula (i) is selected from the group consisting of 0, 1, 2, 3, 4 and 5. In certain embodiments, n of formula (i) is selected from the group consisting of 0, 1, 2 and 3. In certain embodiments, n of formula (i) is selected from the group consisting of 0 and 1. In certain embodiments, n of formula (i) is 0.

In certain embodiments, -L$^2$- is a moiety selected from the group consisting of

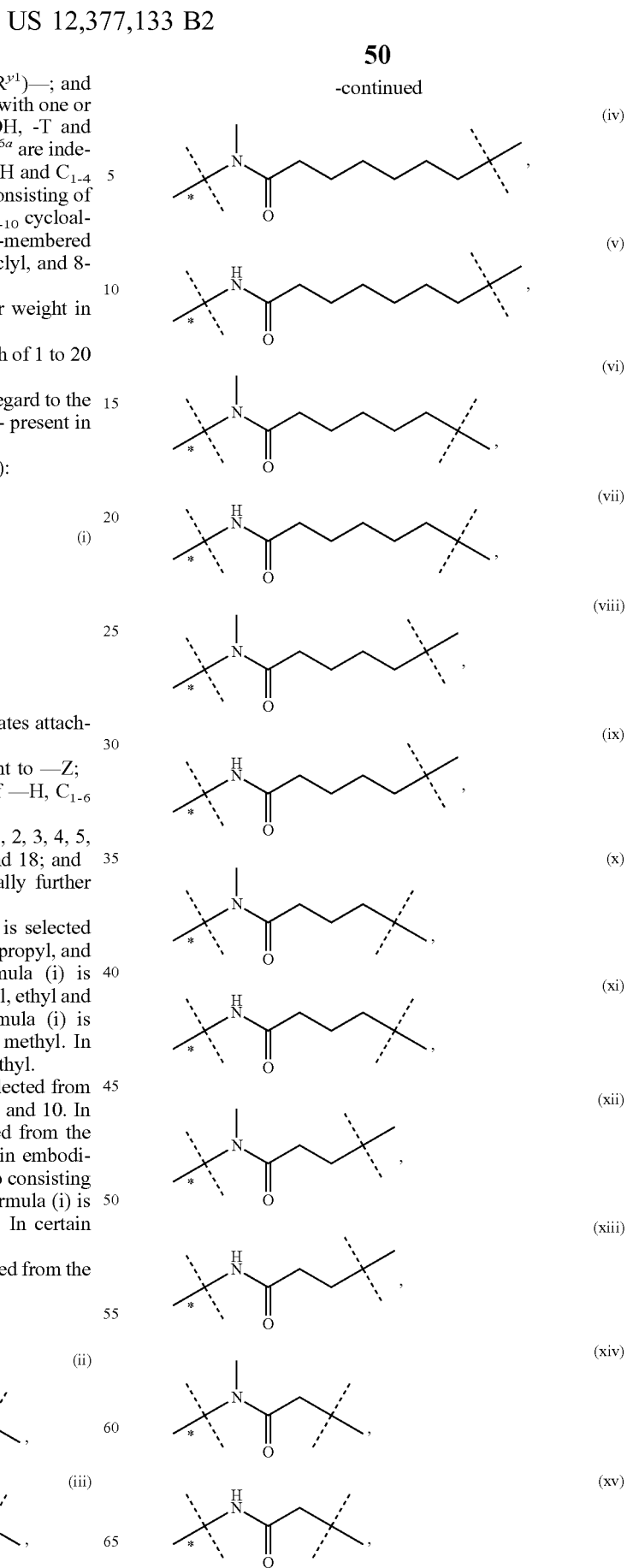

-continued

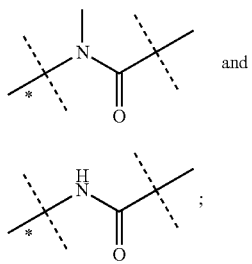
(xvi)

and

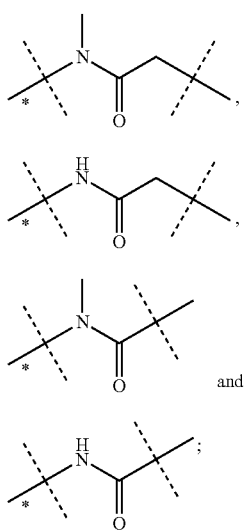
(xvii)

;

wherein
the dashed line marked with the asterisk indicates attachment to -L$^1$-;
the unmarked dashed line indicates attachment to —Z and
wherein the moieties (ii), (iii), (iv), (v), (vi), (vii), (viii), (ix), (x), (xi), (xii), (xiii), (xiv), (xv), (xvi) and (xvii) are optionally further substituted.

In certain embodiments, -L$^2$- is selected from the group consisting of

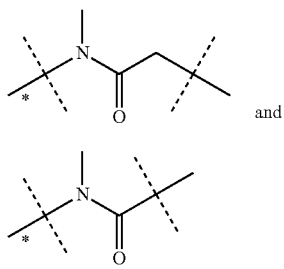
(xiv)

, (xv)

, (xvi)

and (xvii)

;

wherein
the dashed line marked with the asterisk indicates attachment to -L$^1$-; and
the unmarked dashed line indicates attachment to —Z.

In certain embodiments, -L$^2$- is selected from the group consisting of (xiv)

and (xvi)

wherein
the dashed line marked with the asterisk indicates attachment to -L$^1$-; and
the unmarked dashed line indicates attachment to —Z.

In certain embodiments, -L$^2$- is of formula (xvi):

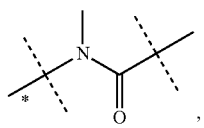
(xvi)

, wherein
the dashed line marked with the asterisk indicates attachment to -L$^1$-; and
the unmarked dashed line indicates attachment to —Z.

In certain embodiments, the moiety -L$^1$-L$^2$- is selected from the group consisting of

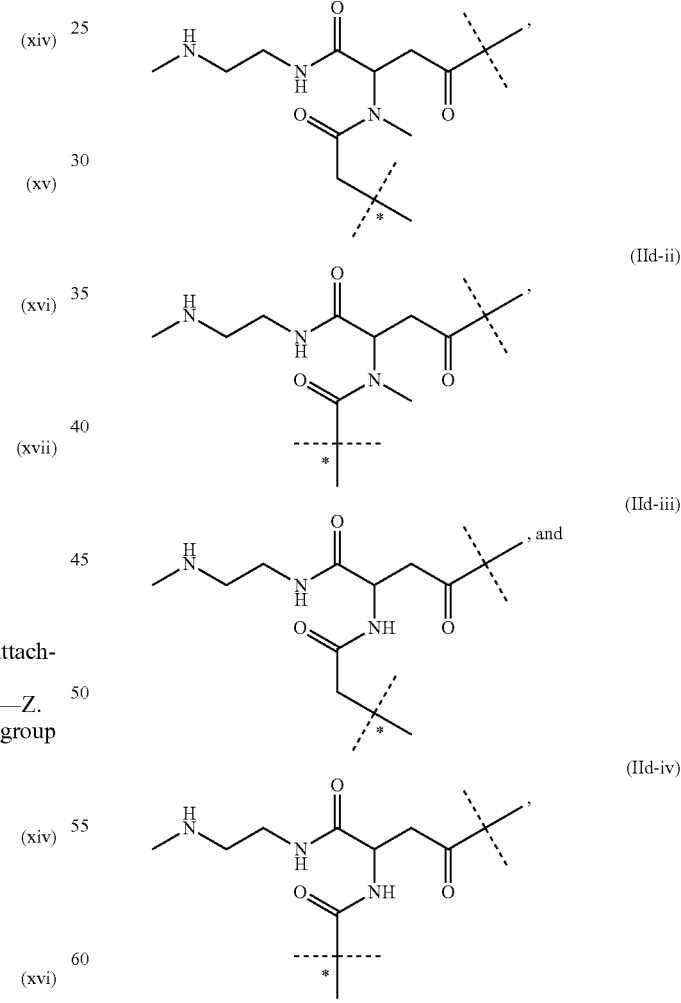

wherein
the unmarked dashed line indicates the attachment to a nitrogen of -D which is a CNP moiety by forming an amide bond; and the dashed line marked with the asterisk indicates attachment to —Z.

In certain embodiments, the moiety -L¹-L²- is of formula (IId-ii):

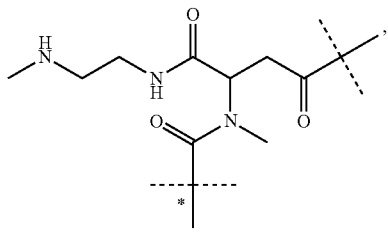
(IId-ii)

wherein
the unmarked dashed line indicates the attachment to a nitrogen of -D which is a CNP moiety by forming an amide bond; and
the dashed line marked with the asterisk indicates attachment to —Z.

In certain embodiments, the moiety -L¹-L²- is of formula (IId-ii'):

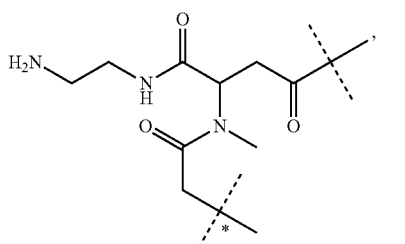
(IId-ia)

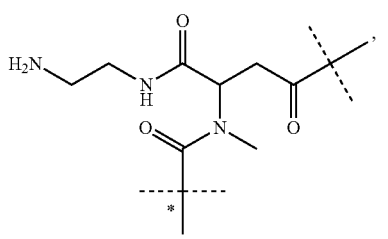
(IId-iia)

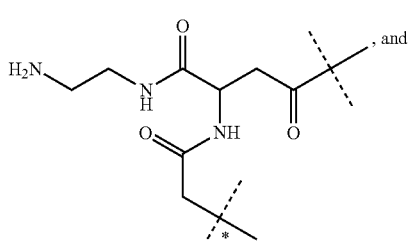
(IId-iiia)

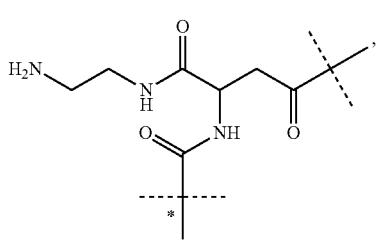
(IId-iva)

wherein
the unmarked dashed line indicates the attachment to a nitrogen of -D which is a CNP moiety by forming an amide bond; and
the dashed line marked with the asterisk indicates attachment to —Z.

In certain embodiments, the moiety -L¹-L²- is selected from the group consisting of

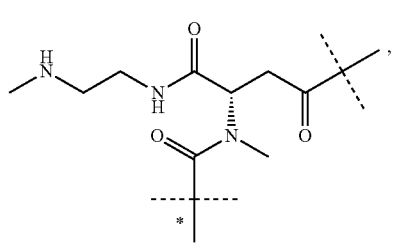
(IId-ii')

wherein
the unmarked dashed line indicates the attachment to a nitrogen of -D which is a CNP moiety by forming an amide bond; and
the dashed line marked with the asterisk indicates attachment to —Z.

In certain embodiments, the moiety -L¹-L²- is of formula (IId-iia):

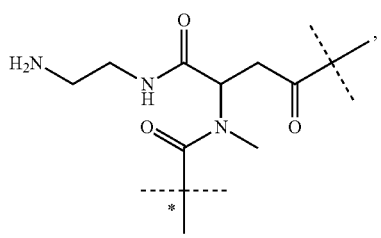
(IId-iia)

wherein
the unmarked dashed line indicates the attachment to a nitrogen of -D which is a CNP moiety by forming an amide bond; and
the dashed line marked with the asterisk indicates attachment to —Z.

In certain embodiments, the moiety -L¹-L²- is of formula (IId-iia'):

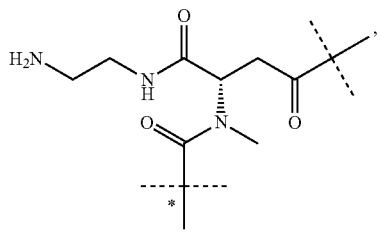
(IId-iia')

wherein
the unmarked dashed line indicates the attachment to a nitrogen of -D which is a CNP moiety by forming an amide bond; and the dashed line marked with the asterisk indicates attachment to —Z.

In certain embodiments, the moiety -L$^1$-L$^2$- is selected from the group consisting of

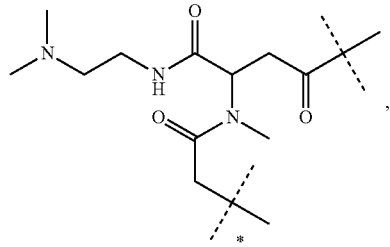

(IId-ib)

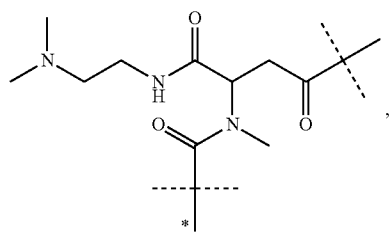

(IId-iib)

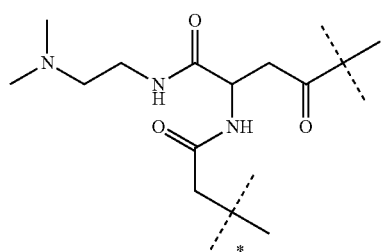

(IId-iiib)

and

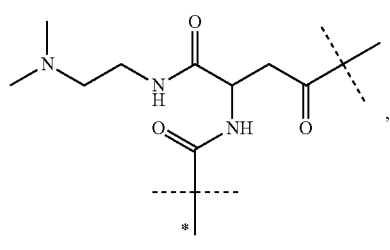

(IId-ivb)

wherein the unmarked dashed line indicates the attachment to a nitrogen of -D which is a CNP moiety by forming an amide bond; and the dashed line marked with the asterisk indicates attachment to —Z.

In certain embodiments, the moiety -L$^1$-L$^2$- is of formula (IId-iib):

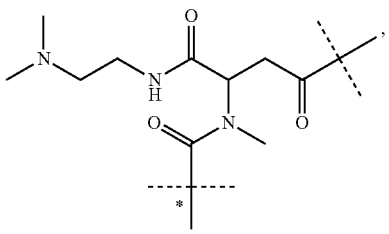

(IId-iib)

wherein the unmarked dashed line indicates the attachment to a nitrogen of -D which is a CNP moiety by forming an amide bond; and the dashed line marked with the asterisk indicates attachment to —Z.

In certain embodiments, the moiety -L$^1$-L$^2$- is of formula (IId-iib'):

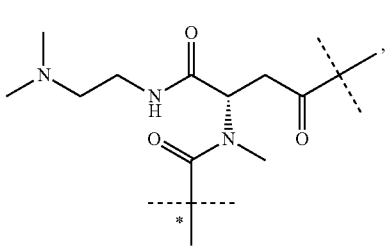

(IId-iib')

wherein the unmarked dashed line indicates the attachment to a nitrogen of -D which is a CNP moiety by forming an amide bond; and the dashed line marked with the asterisk indicates attachment to —Z.

In certain embodiments, —Z of formula (Ia) or (Ib) has a molecular weight ranging from 5 to 200 kDa. In certain embodiments, —Z of formula (Ia) or (Ib) has a molecular weight ranging from 8 to 100 kDa. In certain embodiments, —Z of formula (Ia) or (Ib) has a molecular weight ranging from 10 to 80 kDa. In certain embodiments, —Z of formula (Ia) or (Ib) has a molecular weight ranging from 12 to 60 kDa. In certain embodiments, —Z of formula (Ia) or (Ib) has a molecular weight ranging from 15 to 40 kDa. In certain embodiments, —Z of formula (Ia) or (Ib) has a molecular weight of about 20 kDa. In certain embodiments, —Z of formula (Ia) or (Ib) has a molecular weight of about 40 kDa.

The polymeric moiety —Z of formula (Ia) or (Ib) comprises a polymer. In certain embodiments, —Z of formula (Ia) or (Ib) comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), polypropylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments, —Z of formula (Ia) or (Ib) comprises a protein. Preferred proteins are selected from the group consisting of carboxyl-terminal peptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc-fusion proteins.

In certain embodiments, —Z of formula (Ia) or (Ib) is a polysarcosine. In certain embodiments, —Z of formula (Ia) or (Ib) comprises poly(N-methylglycine). In certain embodiments, —Z of formula (Ia) or (Ib) comprises a random coil protein moiety. In certain embodiments, —Z of formula (Ia) or (Ib) comprises one random coil protein moiety. In certain embodiments, —Z of formula (Ia) or (Ib) comprises two random coil protein moieties. In certain embodiments, —Z of formula (Ia) or (Ib) comprises three random coil protein moieties. In certain embodiments, —Z of formula (Ia) or (Ib) comprises four random coil protein moieties. In certain embodiments, —Z of formula (Ia) or (Ib) comprises five random coil protein moieties. In certain embodiments, —Z of formula (Ia) or (Ib) comprises six random coil protein moieties. In certain embodiments, —Z of formula (Ia) or (Ib) comprises seven random coil protein moieties. In certain embodiments, —Z of formula (Ia) or (Ib) comprises eight random coil protein moieties.

In certain embodiments, such random coil protein moiety comprises at least 25 amino acid residues and at most 2000 amino acids. In certain embodiments, such random coil protein moiety comprises at least 30 amino acid residues and at most 1500 amino acid residues. In certain embodiments, such random coil protein moiety comprises at least 50 amino acid residues and at most 500 amino acid residues.

In certain embodiments, —Z of formula (Ia) or (Ib) comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine and proline. In certain embodiments, at least 10%, but less than 75%, in certain embodiments less than 65% of the total number of amino acid residues of such random coil protein moiety are proline residues. In certain embodiments, such random coil protein moiety is as described in WO 2011/144756 A1, which is hereby incorporated by reference in its entirety. In certain embodiments, —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, —Z of formula (Ia) or (Ib) comprises a PA moiety.

In certain embodiments, —Z of formula (Ia) or (Ib) comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine, serine and proline. In certain embodiments, at least 4%, but less than 40% of the total number of amino acid residues of such random coil protein moiety are proline residues. In certain embodiments, such random coil protein moiety is as described in WO 2008/155134 A1, which is hereby incorporated by reference in its entirety. In certain embodiments, —Z of formula (Ia) or (Ib) comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z of formula (Ia) or (Ib) comprises a PAS moiety.

In certain embodiments, —Z of formula (Ia) or (Ib) comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z of formula (Ia) or (Ib) comprises a PAG moiety.

In certain embodiments, —Z of formula (Ia) or (Ib) comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from proline and glycine. A moiety comprising such random coil protein moiety comprising proline and glycine will be referred to as "PG" or "PG moiety".

In certain embodiments, such PG moiety comprises a moiety of formula (a-0)

$$[(Gly)_p\text{-Pro-}(Gly)_q]_r \qquad (a\text{-}0);$$

wherein p is selected from the group consisting of 0, 1, 2, 3, 4 and 5;

q is selected from the group consisting of 0, 1, 2, 3, 4 and 5;

r is an integer ranging from and including 10 to 1000;

provided that at least one of p and q is at least 1;

In certain embodiments, p of formula (a-0) is selected from the group consisting of 1, 2 and 3.

In certain embodiments, q of formula (a-0) is selected from 0, 1 and 2.

In certain embodiments, the PG moiety comprises the sequence of SEQ ID NO:97: GGPGGPGPGGPGGPGPGGPG In certain embodiments, the PG moiety comprises the sequence of formula (a-0-a)

(GGPGGPGPGGPGGPGPGGPG)$_v$, (a-0-a), wherein v is an integer ranging from and including 1 to 50.

It is understood that the sequence of formula (a-0-a) comprises v replicates of the sequence of SEQ ID NO:97.

Accordingly, —Z of formula (Ia) or (Ib) comprises a PG moiety.

In certain embodiments, —Z of formula (Ia) or (Ib) comprises a random coil protein moiety of which at least 80%, in certain embodiments at least 85%, in certain embodiments at least 90%, in certain embodiments at least 95%, in certain embodiments at least 98% and in certain embodiments 99% of the total number of amino acids forming said random coil protein moiety are selected from alanine, glycine, serine, threonine, glutamate and proline. In certain embodiments, such random coil protein moiety is as described in WO 2010/091122 A1 which is hereby incorporated by reference. In certain embodiments, —Z of formula (Ia) or (Ib) comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z of formula (Ia) or (Ib) comprises an XTEN moiety.

In certain embodiments, —Z of formula (Ia) or (Ib) is a hyaluronic acid-based polymer.

In certain embodiments, —Z of formula (Ia) or (Ib) is a polymeric moiety as disclosed in WO 2013/024047 A1 which is herewith incorporated by reference.

In certain embodiments, —Z of formula (Ia) or (Ib) is a polymeric moiety as disclosed in WO 2013/024048 A1 which is herewith incorporated by reference.

In certain embodiments, —Z of formula (Ia) or (Ib) is a PEG-based polymer. In certain embodiments, —Z is a branched or multi-arm PEG-based polymer.

In certain embodiments, —Z of formula (Ia) or (Ib) is a branched polymer. In certain embodiments, —Z of formula (Ia) or (Ib) is a branched polymer having one, two, three, four, five or six branching points. In certain embodiments, —Z of formula (Ia) or (Ib) is a branched polymer having one, two or three branching points. In certain embodiments, —Z of formula (Ia) or (Ib) is a branched polymer having one branching point. In certain embodiments, —Z of formula (Ia) or (Ib) is a branched polymer having two branching points. In certain embodiments, —Z of formula (Ia) or (Ib) is a branched polymer having three branching points.

In certain embodiments, a branching point is selected from the group consisting of —N<, —CH< and >C<.

In certain embodiments, such branched moiety —Z of formula (Ia) or (Ib) is PEG-based.

In certain embodiments, such branched moiety —Z of formula (Ia) or (Ib) has a molecular weight ranging from and including 5 kDa to 500 kDa. In certain embodiments, such branched moiety —Z of formula (Ia) or (Ib) has a molecular weight ranging from and including 10 kDa to 250 kDa. In certain embodiments, such branched moiety —Z of formula (Ia) or (Ib) has a molecular weight ranging from and including 10 kDa to 150 kDa. In certain embodiments, such branched moiety —Z of formula (Ia) or (Ib) has a molecular weight ranging from and including 12 kDa to 100 kDa. In certain embodiments, such branched moiety —Z of formula (Ia) or (Ib) has a molecular weight ranging from and including 15 kDa to 80 kDa. In certain embodiments, such branched moiety —Z of formula (Ia) or (Ib) has a molecular weight ranging from and including 10 kDa to 80 kDa. In certain embodiments, the molecular weight is about 10 kDa. In certain embodiments, the molecular weight of such branched moiety —Z of formula (Ia) or (Ib) is about 20 kDa. In certain embodiments, the molecular weight of such branched moiety —Z of formula (Ia) or (Ib) is about 30 kDa. In certain embodiments, the molecular weight of such a branched moiety —Z of formula (Ia) or (Ib) is about 40 kDa. In certain embodiments, the molecular weight of such a branched moiety —Z of formula (Ia) or (Ib) is about 50 kDa. In certain embodiments, the molecular weight of such a branched moiety —Z of formula (Ia) or (Ib) is about 60 kDa. In certain embodiments, the molecular weight of such a branched moiety —Z of formula (Ia) or (Ib) is about 70 kDa. In certain embodiments, the molecular weight of such a branched moiety —Z of formula (Ia) or (Ib) is about 80 kDa. In certain embodiments, such branched moiety —Z of formula (Ia) or (Ib) has a molecular weight of about 40 kDa.

In certain embodiments, —Z comprises a moiety

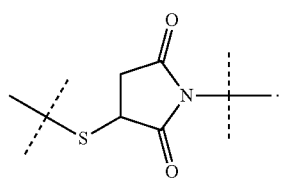

In certain embodiments, —Z comprises an amide bond.

In certain embodiments, —Z of formula (Ia) or (Ib) comprises a moiety of formula (a)

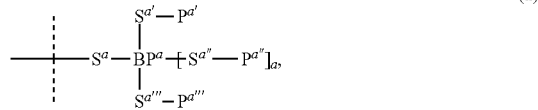

wherein the dashed line indicates attachment to -$L^2$- or to the remainder of —Z;

$BP^a$ is a branching point selected from the group consisting of —N<, —CR< and >C<;

—R is selected from the group consisting of —H and $C_{1-6}$ alkyl;

a is 0 if $BP^a$ is —N< or —CR< and n is 1 if $BP^a$ is >C<;

—$S^a$—, —$S^{a'}$—, —$S^{a''}$— and —$S^{a'''}$— are independently of each other a chemical bond or are selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O)N($R^2$)—, —S(O)$_2$—, —S(O)—, —N($R^2$)S(O)$_2$N($R^{2a}$)—, —S—, —N($R^2$)—, —OC(OR$^2$)($R^{2a}$)—, —N($R^2$)C(O)N($R^{2a}$)—, and —OC(O)N($R^2$)—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each —$R^1$ is independently selected from the group consisting of halogen, —CN, oxo (=O), —COOR$^3$, —OR$^3$, —C(O)R$^3$, —C(O)N($R^3R^{3a}$), —S(O)$_2$N($R^3R^{3a}$), —S(O)N($R^3R^{3a}$), —S(O)$_2$R$^3$, —S(O)R$^3$, —N($R^3$)S(O)$_2$N($R^{3a}R^{3b}$), —SR$^3$, —N($R^3R^{3a}$), —NO$_2$, —OC(O)R$^3$, —N($R^3$)C(O)R$^{3a}$, —N($R^3$)S(O)$_2$R$^{3a}$, —N($R^3$)S(O)R$^{3a}$, —N($R^3$)C(O)OR$^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different; and —$P^{a'}$, —$P^{a''}$ and —$P^{a'''}$ are independently a polymeric moiety.

Optionally, the moiety of formula (a) is substituted with one or more substituents.

In certain embodiments, $BP^a$ of formula (a) is —N<.

In certain embodiments, $BP^a$ of formula (a) is —CR<. In certain embodiments, —R is —H.

Accordingly, in certain embodiments, a of formula (a) is 0.

In certain embodiments, $BP^a$ of formula (a) is >C<.

In certain embodiments, —$S^a$— of formula (a) is a chemical bond.

In certain embodiments, —$S^a$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(OR$^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^a$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$S^{a'}$— of formula (a) is a chemical bond.

In certain embodiments, —$S^{a'}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(OR$^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—. In certain embodiments, —$S^{a''}$— of formula (a) is a chemical bond.

In certain embodiments, —$S^{a''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(OR$^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$S^{a'''}$— of formula (a) is a chemical bond.

In certain embodiments, —$S^{a'''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(OR$^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a'''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$P^{a'}$, —$P^{a''}$ and —$P^{a'''}$ of formula (a) independently comprise a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments, —$P^{a'}$, —$P^{a''}$ and —$P^{a'''}$ of formula (a) independently have a molecular weight ranging from and including 5 kDa to 50 kDa, in certain embodiments ranging from and including 5 kDa to 40 kDa, in certain embodiments ranging from and including 7.5 kDa to 35 kDa, in certain embodiments ranging from and 7.5 to 30 kDa, in certain embodiments ranging from and including 10 to 30 kDa.

In certain embodiments, —$P^{a'}$, —$P^{a''}$ and —$P^{a'''}$ of formula (a) have a molecular weight of about 5 kDa. In certain embodiments, —$P^{a'}$, —$P^{a''}$ and —$P^{a'''}$ of formula (a) have a molecular weight of about 7.5 kDa. In certain embodiments, —$P^{a'}$, —$P^{a''}$ and —$P^{a'''}$ of formula (a) have a molecular weight of about 10 kDa. In certain embodiments, —$P^{a'}$, —$P^{a''}$ and —$P^{a'''}$ of formula (a) have a molecular weight of about 12.5 kDa. In certain embodiments, —$P^{a'}$, —$P^{a''}$ and —$P^{a'''}$ of formula (a) have a molecular weight of about 15 kDa. In certain embodiments, —$P^{a'}$, —$P^{a''}$ and —$P^{a'''}$ of formula (a) have a molecular weight of about 20 kDa.

In certain embodiments, —$P^{a'}$, —$P^{a''}$ and —$P^{a'''}$ of formula (a) independently comprise a PEG-based moiety. In certain embodiments, —$P^{a'}$, —$P^{a''}$ and —$P^{a'''}$ of formula (a) independently comprise a PEG-based moiety comprising at least 20% PEG, in certain embodiments at least 30% PEG, in certain embodiments at least 40% PEG, in certain embodiments at least 50% PEG, in certain embodiments at least 60% PEG, in certain embodiments at least 70% PEG, in certain embodiments at least 80% PEG and in certain embodiments at least 90% PEG.

In certain embodiments, —$P^{a'}$, —$P^{a''}$ and —$P^{a'''}$ of formula (a) independently comprise a protein moiety, in certain embodiments a random coil protein moiety and in certain embodiments a random coil protein moiety selected from the group consisting of PA, PAS, PAG, PG and XTEN moieties.

In certain embodiments, —$P^{a'}$, —$P^{a''}$ and —$P^{a'''}$ of formula (a) are a PA moiety. In certain embodiments, —$P^{a'}$, —$P^{a''}$ and —$P^{a'''}$ of formula (a) are a PAS moiety. In certain embodiments, —$P^{a'}$, —$P^{a''}$ and —$P^{a'''}$ of formula (a) are a PAG moiety. In certain embodiments, —$P^{a'}$, —$P^{a''}$ and —$P^{a'''}$ of formula (a) are a PG moiety. In certain embodiments, —$P^{a'}$, —$P^{a''}$ and —$P^{a'''}$ of formula (a) are an XTEN moiety.

In certain embodiments, —Z comprises one moiety of formula (a). In certain embodiments, —Z comprises two moieties of formula (a). In another embodiment, —Z comprises three moieties of formula (a). In certain embodiments, —Z comprises four moieties of formula (a). In certain embodiments, —Z comprises five moieties of formula (a). In certain embodiments, —Z comprises six moieties of formula (a).

In certain embodiments, —Z comprises a moiety of formula (b):

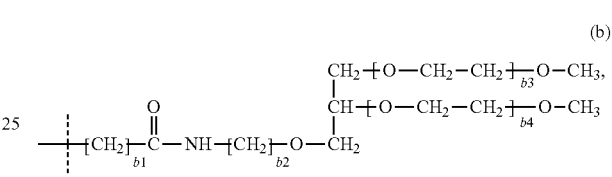

wherein
the dashed line indicates attachment to -$L^2$- or to the remainder of —Z;
b1 is selected from the group consisting of 0, 1, 2, 3, 4, 5, 6, 7 and 8;
b2 is selected from the group consisting of 1, 2, 3, 4, 5, 6, 7 and 8;
b3 is an integer ranging from and including 150 to 1000; in certain embodiments, ranging from and including 150 to 500; and in certain embodiments, ranging from and including 200 to 460; and
b4 is an integer ranging from and including 150 to 1000; in certain embodiments, ranging from and including 150 to 500; and in certain embodiments, ranging from and including 200 to 460.

Optionally, the moiety of formula (b) is substituted with one or more substituents.

In certain embodiments, b3 and b4 of formula (b) are the same integer.

In certain embodiments, b3 and b4 of formula (b) are both an integer ranging from 200 to 250 and in certain embodiments, b3 and b4 of formula (b) are about 225. In certain embodiments, b3 and b4 of formula (b) are both an integer ranging from 400 to 500 and in certain embodiments, b3 and b4 of formula (b) are about 450.

In certain embodiments, b1 of formula (b) is selected from the group consisting of 0, 1, 2, 3 and 4. In certain embodiments, b1 of formula (b) is selected from the group consisting of 1, 2 and 3. In certain embodiments, b1 of formula (b) is 2.

In certain embodiments, b2 of formula (b) is selected from the group consisting of 1, 2, 3, 4 and 5. In certain embodiments, b2 of formula (b) is selected from the group consisting of 2, 3 and 4. In certain embodiments, b2 of formula (b) is 3.

In certain embodiments, b1 of formula (b) is 2, b2 of formula (b) is 3, and b3 and b4 are both about 450. In certain embodiments, b1 of formula (b) is 2, b2 of formula (b) is 3, and b3 and b4 are both about 225.

In certain embodiments, —Z comprises one moiety of formula (b). In certain embodiments, —Z comprises two moieties of formula (b). In certain embodiments, —Z comprises three moieties of formula (b). In certain embodiments, —Z comprises four moieties of formula (b). In certain embodiments, —Z comprises five moieties of formula (b). In certain embodiments, —Z comprises six moieties of formula (b).

In certain embodiments, —Z comprises a moiety of formula (c):

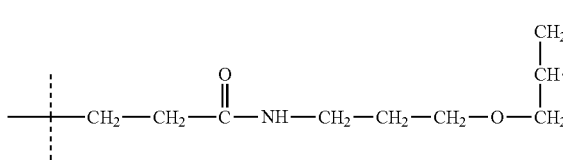

(c)

wherein
the dashed line indicates attachment to -L$^2$- or to the remainder of —Z;
c1 and c2 are independently an integer ranging from and including 150 to 500; in certain embodiments, ranging from and including 200 to 460.

Optionally, the moiety of formula (c) is substituted with one or more substituents.

In certain embodiments, both c1 and c2 of formula (c) are the same integer.

In certain embodiments, c1 and c2 of formula (c) range from and include 200 to 250 and in certain embodiments, are about 225. In certain embodiments, c1 and c2 of formula (c) range from and include 400 to 500 and in certain embodiments, c1 and c2 of formula (c) are about 450.

In certain embodiments, the moiety —Z is a branched PEG-based polymer comprising at least 10% PEG, has one branching point and two PEG-based polymer arms and has a molecular weight of about 40 kDa. Accordingly, each of the two PEG-based polymer arms has a molecular weight of about 20 kDa. In certain embodiments, the branching point is —CH<.

In certain embodiments, —Z comprises one moiety of formula (c). In certain embodiments, —Z comprises two moieties of formula (c). In certain embodiments, —Z comprises three moieties of formula (c). In certain embodiments, —Z comprises four moieties of formula (c). In certain embodiments, —Z comprises five moieties of formula (c). In certain embodiments, —Z comprises six moieties of formula (c).

In certain embodiments, the moiety —Z is of formula (d)

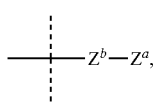

(d)

wherein
the dashed line indicates attachment to -L$^2$-;
—Z$^b$— is selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^1$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$)—, —N(R$^2$)C(O)N(R$^{2a}$)—, and —OC(O)N(R$^2$)—;

each -T- is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R$^1$, which are the same or different;

each —R$^1$ is independently selected from the group consisting of halogen, —CN, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different;

each —R$^2$, —R$^{2a}$, —R$^3$, —R$^{3a}$ and —R$^{3b}$ is independently selected from the group consisting of —H, and C$_{1-6}$ alkyl, wherein C$_{1-6}$ alkyl is optionally substituted with one or more halogen, which are the same or different;

and
—Z$^a$ is

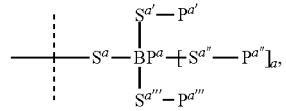

wherein
BP$^a$, —S$^a$—, —S$^{a'}$—, —S$^{a''}$—, —S$^{a'''}$—, —P$^{a'}$, —P$^{a''}$, —P$^{a'''}$ and a are used as defined for formula (a).

Optionally, the moiety of formula (d) is substituted with one or more substituents.

In certain embodiments, BP$^a$, —S$^a$—, —S$^{a'}$—, —S$^{a''}$—, —S$^{a'''}$—, —P$^{a'}$, —P$^{a''}$, —P$^{a'''}$ of formula (d) are as defined above for formula (a).

In certain embodiments, —Z$^a$ of formula (d) is of formula (b). In certain embodiments, b1, b2, b3 and b4 are as described for formula (b).

In certain embodiments, the moiety —Z of formula (Ia) or (Ib) is of formula (e):

(e)

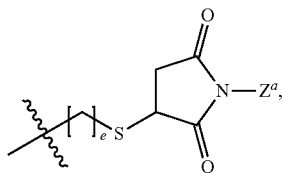

wherein
the dashed line indicates attachment to -L²-;
e is selected from the group consisting of 1, 2, 3, 4, 5, 6, 7, 8, 9, 10, 11, 12, 13, 14 and 15; and
—$Z^a$ is

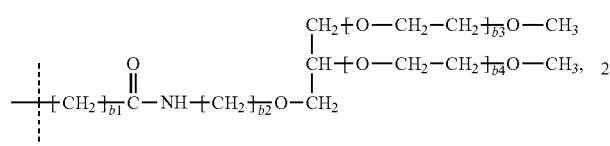

wherein
b1, b2, b3 and b4 are used as defined for formula (b).

Optionally, the moiety of formula (e) is substituted with one or more substituents.

In certain embodiments, for b1, b2, b3 and b4 of formula (e) are as defined above for formula (b).

In certain embodiments, e of formula (e) is 1. In certain embodiments, e of formula (e) is 2. In certain embodiments, e of formula (e) is 3. In certain embodiments, e of formula (e) is 4. In certain embodiments, e of formula (e) is 5. In certain embodiments, e of formula (e) is 6. In certain embodiments, e of formula (e) is 7. In certain embodiments, e of formula (e) is 8. In certain embodiments, e of formula (e) is 9. In certain embodiments, e of formula (e) is 10. In certain embodiments, e of formula (e) is 11. In certain embodiments, e of formula (e) is 12. In certain embodiments, e of formula (e) is 13. In certain embodiments, e of formula (e) is 14. In certain embodiments, e of formula (e) is 15.

In certain embodiments, e of formula (e) is selected from the group consisting of 2, 3, 4, 5, 6, 7, 8 and 9. In certain embodiments, e of formula (e) is selected from 3, 4, 5 and 6. In certain embodiments, e of formula (e) is 5.

In certain embodiments, e of formula (e) is 5, b1 of formula (e) is 2, b2 of formula (e) is 3 and b3 and b4 of formula (e) are both about 450.

In certain embodiments, the moiety —Z of formula (Ia) or (Ib) is of formula (e-i) or (e-i'):

(e-i)

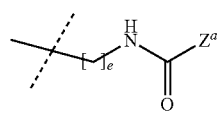

(e-i')

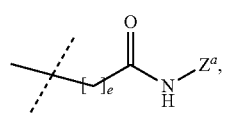

wherein
the dashed line indicates attachment to -L²-,
e is selected from the group consisting of 1, 2, 3, 4, 5, 6, 7, 8, 9, 10, 11, 12, 13, 14 and 15;
—$Z^a$ is

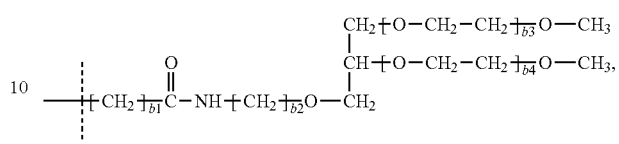

wherein
b1, b2, b3 and b4 are used as defined for formula (b).

In certain embodiments, for b1, b2, b3 and b4 of formula (e-i) and (e-i') are as defined above for formula (b).

In certain embodiments, e of formula (e-i) and (e-i') are as described for formula (e).

In certain embodiments, b1 of formula (e-i) and (e-i') is 2, b2 of formula (e-i) and (e-i') is 3 and b3 and b4 of formula (e-i) and (e-i') are both about 450.

In certain embodiments, —Z of formula (Ia) or (Ib) is of formula (e-i).

In certain embodiments, the moiety —Z is a branched PEG-based polymer comprising at least 10% PEG, has three branching points and four PEG-based polymer arms and has a molecular weight of about 40 kDa. Accordingly, each of the four PEG-based polymer arms has a molecular weight of about 10 kDa. In certain embodiments, each of the three branching points is —CH<.

In certain embodiments, the moiety —Z is of formula (f)

(f)

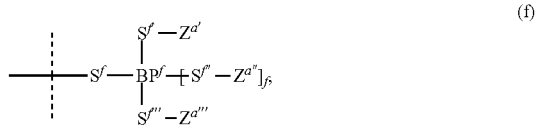

wherein
the dashed line indicates attachment to -L²-;
$BP^f$ is a branching point selected from the group consisting of —N<, —CR< and >C<;
—R is selected from the group consisting of —H and $C_{1-6}$ alkyl;
f is 0 if $BP^f$ is —N< or —CR< and f is 1 if $BP^f$ is >C<;
—$S^f$—, —$S^{f'}$—, —$S^{f''}$— and —$S^{f'''}$— are independently either a chemical bond or are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O)N($R^2$)—, —S(O)$_2$—, —S(O)—, —N($R^2$)S(O)$_2$N($R^{2a}$)—, —S—, —N($R^2$)—, —OC(O$R^2$)($R^{2a}$)—, —N($R^2$)C(O)N($R^{2a}$)—, and —OC(O)N($R^2$)—;
each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each $R^1$ is independently selected from the group consisting of halogen, —CN, oxo (═O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and $C_{1-6}$ alkyl; wherein $C_{1-6}$ alkyl is optionally substituted with one or more halogen, which are the same or different;

each —R$^2$, —R$^{2a}$, —R$^3$, —R$^{3a}$ and —R$^{3b}$ is independently selected from the group consisting of —H, and $C_{1-6}$ alkyl, wherein $C_{1-6}$ alkyl is optionally substituted with one or more halogen, which are the same or different;

and

—Z$^{a'}$, —Z$^{a''}$ and —Z$^{a'''}$ are independently

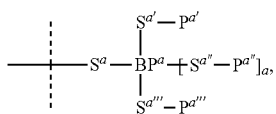

wherein

BP$^a$, —S$^a$—, —S$^{a'}$—, —S$^{a''}$—, —S$^{a'''}$—, —P$^{a'}$, —P$^{a''}$, —P$^{a'''}$ and a are used as defined for formula (a).

Optionally, the moiety of formula (f) is substituted with one or more substituents.

In certain embodiments, BP$^a$, —S$^a$—, —S$^{a'}$—, —S$^{a''}$—, —S$^{a'''}$—, —P$^{a'}$, —P$^{a''}$ and —P$^{a'''}$ of formula (f) are as defined above for formula (a).

In certain embodiments, BP of formula (f) is —CR< and r is 0. In certain embodiments, —R is —H.

In certain embodiments, —S$^f$— of formula (f) is a chemical bond.

In certain embodiments, —Z$^{a'}$, —Z$^{a''}$ and —Z$^{a'''}$ of formula (f) have the same structure. In certain embodiments, —Z$^{a'}$, —Z$^{a''}$ and —Z$^{a'''}$ of formula (f) are of formula (b).

In certain embodiments, b1, b2, b3 and b4 are as described for formula (b).

In certain embodiments, —S$^f$— of formula (f) is a chemical bond, BP$^a$ of formula (f) is —CR< with —R being —H. In certain embodiments, —S$^f$— of formula (f) is a chemical bond, BP$^a$ of formula (f) is —CR< with —R being —H and —Z$^{a'}$, —Z$^{a''}$ and —Z$^{a'''}$ of formula (f) are of formula (b).

In certain embodiments, —Z is of formula (g)

(g)

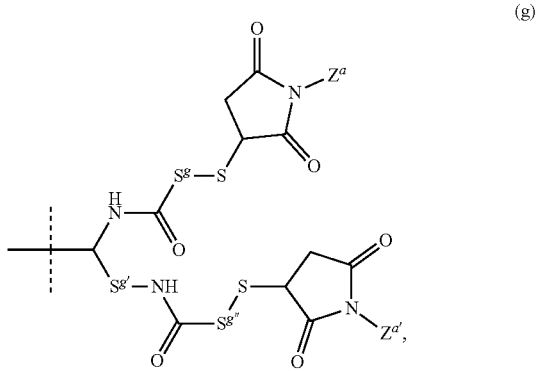

wherein the dashed line indicates attachment to -L$^2$-;

—S$^g$—, —S$^{g'}$— and —S$^{g''}$— are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —R$^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$)—, —N(R$^2$)C(O)N(R$^{2a}$)—, and —OC(O)N(R$^2$)—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —R$^1$, which are the same or different;

each $R^1$ is independently selected from the group consisting of halogen, —CN, oxo (═O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and $C_{1-6}$ alkyl; wherein $C_{1-6}$ alkyl is optionally substituted with one or more halogen, which are the same or different;

each —R$^2$, —R$^{2a}$, —R$^3$, —R$^{3a}$ and —R$^{3b}$ is independently selected from the group consisting of —H, and $C_{1-6}$ alkyl, wherein $C_{1-6}$ alkyl is optionally substituted with one or more halogen, which are the same or different;

and

—Z$^a$ and —Z$^a$ are independently

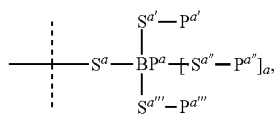

wherein

BP$^a$, —S$^a$—, —S$^{a'}$—, —S$^{a''}$—, —S$^{a'''}$—, —P$^{a'}$, —P$^{a''}$, —P$^{a'''}$ and a are used as defined for formula (a).

Optionally, the moiety of formula (g) is substituted with one or more substituents.

In certain embodiments, BP$^a$, —S$^a$—, —S$^{a'}$—, —S$^{a''}$—, —S$^{a'''}$—, —P$^{a'}$, —P$^{a''}$ and —P$^{a'''}$ of formula (g) are as defined above for formula (a).

In certain embodiments, —S$^g$— of formula (g) is selected from the group consisting of $C_{1-6}$ alkyl, $C_{2-6}$ alkenyl and $C_{2-6}$ alkynyl, which are optionally substituted with one or more —R$^1$, which is the same or different, wherein —R$^1$ is selected from the group consisting of halogen, oxo (═O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)

C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different; and —R$^3$, —R$^{3a}$ and —R$^{3b}$ are independently selected from —H, methyl, ethyl, propyl and butyl.

In certain embodiments, —S$^g$— of formula (g) is selected from C$_{1-6}$ alkyl.

In certain embodiments, —S$^{g'}$— of formula (g) is selected from the group consisting of C$_{1-6}$ alkyl, C$_{2-6}$ alkenyl and C$_{2-6}$ alkynyl, which are optionally substituted with one or more —R$^1$, which is the same or different,
wherein
—R$^1$ is selected from the group consisting of halogen, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different; and —R$^3$, —R$^{3a}$ and —R$^{3b}$ are independently selected from —H, methyl, ethyl, propyl and butyl.

In certain embodiments, —S$^{g'}$— of formula (g) is selected from C$_{1-6}$ alkyl.

In certain embodiments, —S$^{g''}$— of formula (g) is selected from the group consisting of C$_{1-6}$ alkyl, C$_{2-6}$ alkenyl and C$_{2-6}$ alkynyl, which are optionally substituted with one or more —R$^1$, which is the same or different,
wherein
—R$^1$ is selected from the group consisting of halogen, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different; and —R$^3$, —R$^{3a}$ and —R$^{3b}$ are independently selected from —H, methyl, ethyl, propyl and butyl.

In certain embodiments, —S$^{g''}$— of formula (g) is selected from C$_{1-6}$ alkyl.

In certain embodiments, —Z$^a$ and —Z$^{a'}$ of formula (g) have the same structure. In certain embodiments, —Z$^a$ and —Z$^{a'}$ of formula (g) are of formula (b).

In certain embodiments, —Z of formula (Ia) or (Ib) is of formula (g-i)

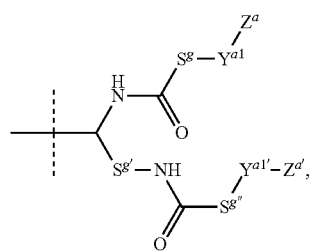

(g-i)

wherein
the dashed line indicates attachment to -L$^2$-;
S$^g$—, —S$^{g'}$— and —S$^{g''}$— are independently selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more —R$^1$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^2$)—, —S(O)$_2$N(R$^2$)—, —S(O)N(R$^2$)—, —S(O)$_2$—, —S(O)—, —N(R$^2$)S(O)$_2$N(R$^{2a}$)—, —S—, —N(R$^2$)—, —OC(OR$^2$)(R$^{2a}$)—, —N(R$^2$)C(O)N(R$^{2a}$)—, and —OC(O)N(R$^2$)—;

each -T- is independently selected from the group consisting of phenyl, naphthyl, indenyl, indanyl, tetralinyl, C$_{3-10}$ cycloalkyl, 3- to 10-membered heterocyclyl, 3- to 11-membered heterobicyclyl, 8- to 30-membered carbopolycyclyl, and 8- to 30-membered heteropolycyclyl; wherein each -T- is independently optionally substituted with one or more —R$^1$, which are the same or different;

each R$^1$ is independently selected from the group consisting of halogen, —CN, oxo (=O), —COOR$^3$, —OR$^3$, —C(O)R$^3$, —C(O)N(R$^3$R$^{3a}$), —S(O)$_2$N(R$^3$R$^{3a}$), —S(O)N(R$^3$R$^{3a}$), —S(O)$_2$R$^3$, —S(O)R$^3$, —N(R$^3$)S(O)$_2$N(R$^{3a}$R$^{3b}$), —SR$^3$, —N(R$^3$R$^{3a}$), —NO$_2$, —OC(O)R$^3$, —N(R$^3$)C(O)R$^{3a}$, —N(R$^3$)S(O)$_2$R$^{3a}$, —N(R$^3$)S(O)R$^{3a}$, —N(R$^3$)C(O)OR$^{3a}$, —N(R$^3$)C(O)N(R$^{3a}$R$^{3b}$), —OC(O)N(R$^3$R$^{3a}$), and C$_{1-6}$ alkyl; wherein C$_{1-6}$ alkyl is optionally substituted with one or more halogen, which are the same or different;

each —R$^2$, —R$^{2a}$, —R$^3$, —R$^{3a}$ and —R$^{3b}$ is independently selected from the group consisting of —H, and C$_{1-6}$ alkyl, wherein C$_{1-6}$ alkyl is optionally substituted with one or more halogen, which are the same or different;

—Y$^{a1}$— and —Y$^{a1'}$— are

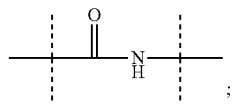

and
—Z$^a$ and —Z$^{a'}$ are independently

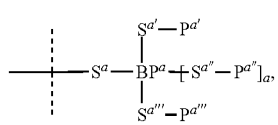

wherein
BP$^a$, —S$^a$—, —S$^{a'}$—, —S$^{a''}$—, —S$^{a'''}$—, —P$^{a'}$, —P$^{a''}$, —P$^{a'''}$ and a are used as defined for formula (a).

Optionally, the moiety of formula (g-i) is substituted with one or more substituents.

In certain embodiments, —$Y^{a1}$— and —$Y^{a1'}$— of formula (g-i) are both

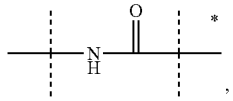

, wherein the dashed line marked with the asterisk is attached to —$Z^a$ or —$Z^{a'}$, respectively.

In certain embodiments, of $BP^a$, —$S^a$—, —$S^{a'}$—, —$S^{a''}$—, —$S^{a'''}$—, —$P^{a'}$, —$P^{a''}$ and —$P^{a'''}$ of formula (g-i) are as defined above for formula (a).

In certain embodiments, of —$S^g$—, —$S^{g'}$— and —$S^{g''}$— of formula (g-i) are as defined for formula (g). In certain embodiments, —$Z^a$ and —$Z^a$ of formula (g-i) have the same structure. In certain embodiments, —$Z^a$ and —$Z^a$ of formula (g-i) are of formula (b). In certain embodiments, for b1, b2, b3 and b4 are as described for formula (b).

In certain embodiments, —Z is of formula (h)

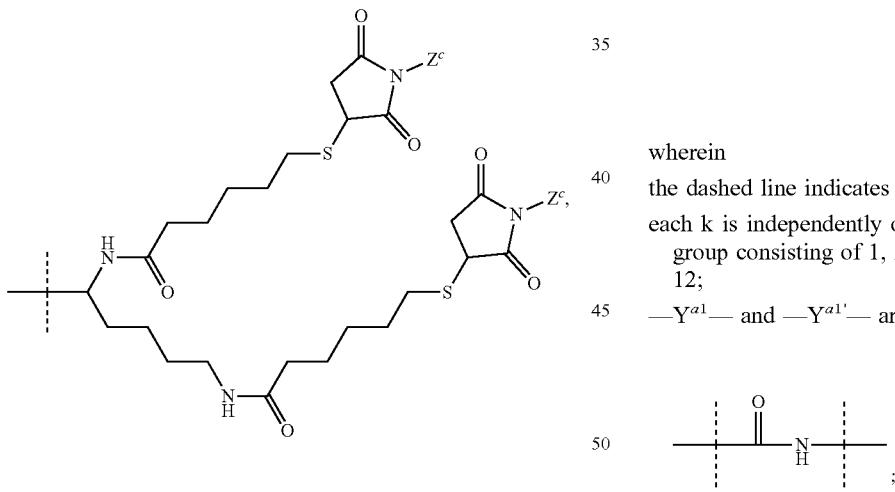

(h)

wherein
the dashed line indicates attachment to -$L^2$-; and
each —$Z^c$ is a moiety wherein
each c1 is an integer independently ranging from about 200 to 250.

Optionally, the moiety of formula (h) is substituted with one or more substituents.

In certain embodiments, both c1 of formula (h) are the same. In certain embodiments, both c1 of formula (h) are about 225.

In certain embodiments, —Z of formula (Ia) or (Ib) is of formula (h-a):

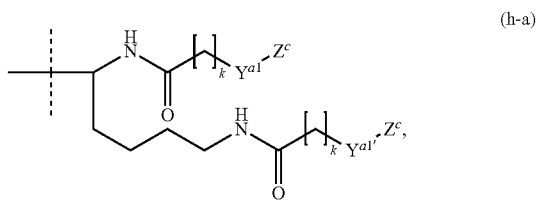

(h-a)

wherein
the dashed line indicates attachment to -$L^2$-;
each k is independently of each other selected from the group consisting of 1, 2, 3, 4, 5, 6, 7, 8, 9, 10, 11 and 12;
—$Y^{a1}$— and —$Y^{a1'}$— are

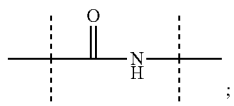

;

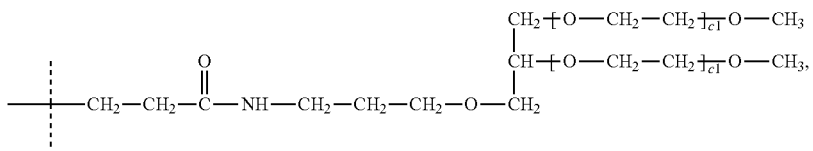

and

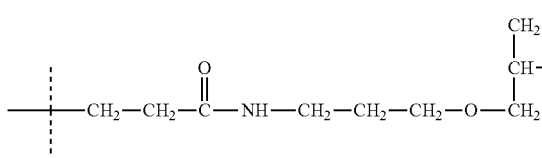

wherein
each c1 is an integer independently ranging from about 200 to 250.

Optionally, the moiety of formula (h-a) is substituted with one or more substituents.

In certain embodiments, each k of formula (h-a) is independently selected from the group consisting of 2, 3, 4, 5, 6 and 7. In certain embodiments, both k of formula (h-a) are identical.

In certain embodiments, both c1 of formula (h-a) are the same.

In certain embodiments, both c1 of formula (h-a) are about 225.

In certain embodiments, $-Y^{a1}-$ and $-Y^{a1'}-$ of formula (h-a) are both

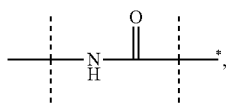

wherein the dashed line marked with the asterisk is attached to $-Z^c$.

In certain embodiments, the moiety $-Z$ is of formula (h-i):

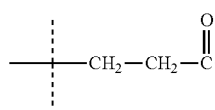

each $-Z^c$ is a moiety

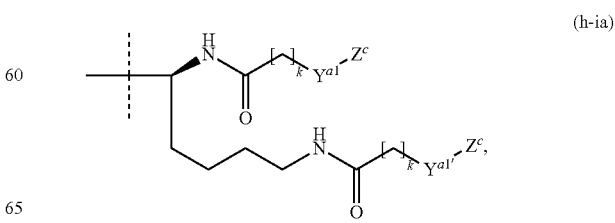

(h-i)

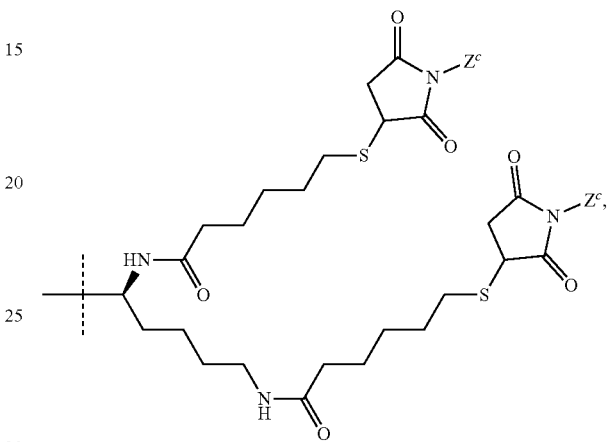

wherein
the dashed line indicates attachment to $-L^2-$; and
each $-Z^c$ is a moiety

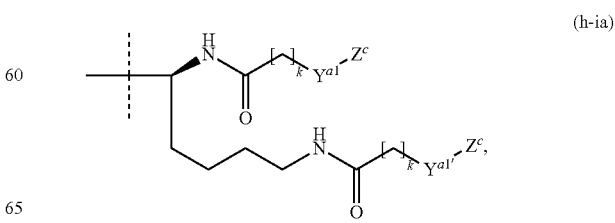

each c1 is an integer independently ranging from 200 to 250.

Optionally, the moiety of formula (h-i) is substituted with one or more substituents.

In certain embodiments, both c1 of formula (h-i) are the same. In certain embodiments, both c1 of formula (h-i) are about 225.

In certain embodiments, the moiety $-Z$ of formula (Ia) or (Ib) is of formula (h-ia):

(h-ia)

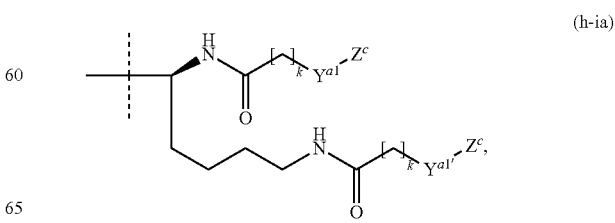

wherein
the dashed line indicates attachment to -L$^2$-;
each k is independently of each other selected from the group consisting of 1, 2, 3, 4, 5, 6, 7, 8, 9, 10, 11 and 12;
$Y^{a1}$— and —$Y^{a1'}$— are

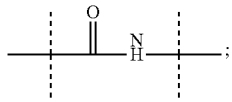

and
each —$Z^c$ is a moiety

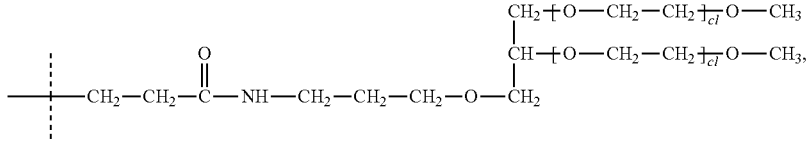

each c1 is an integer independently ranging from 200 to 250.

In certain embodiments, each k of formula (h-ia) is independently selected from the group consisting of 2, 3, 4, 5, 6 and 7. In certain embodiments, both k of formula (h-ia) are identical.

In certain embodiments, both c1 of formula (h-ia) are the same. In certain embodiments, both c1 of formula (h-ia) are about 225.

In certain embodiments, —$Y^{a1}$— and —$Y^{a1'}$— of formula (h-ia) are both

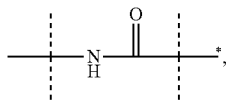

wherein the dashed line marked with the asterisk is attached to —$Z^c$.

In certain embodiments, —Z of formula (Ia) or (Ib) comprises a moiety selected from the group consisting of:

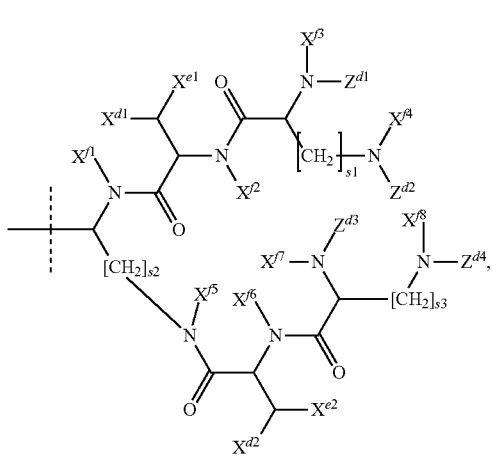 (j-i)

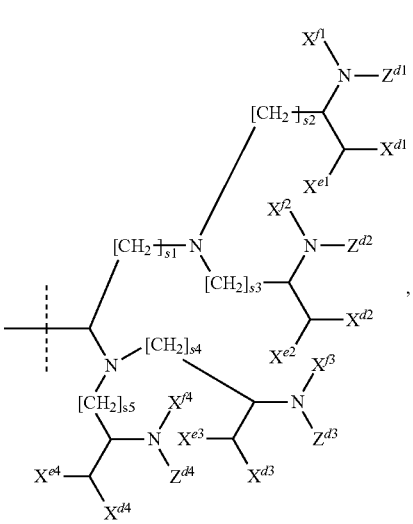 (j-ii)

-continued
(j-iii)
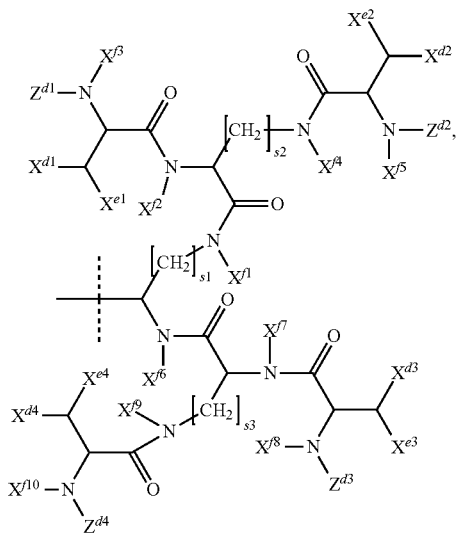
(j-iv)
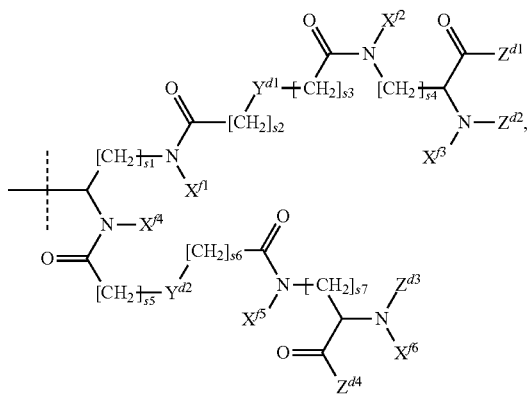
(j-v)
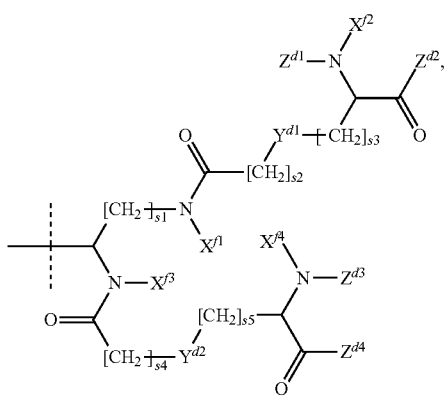
(j-vi)
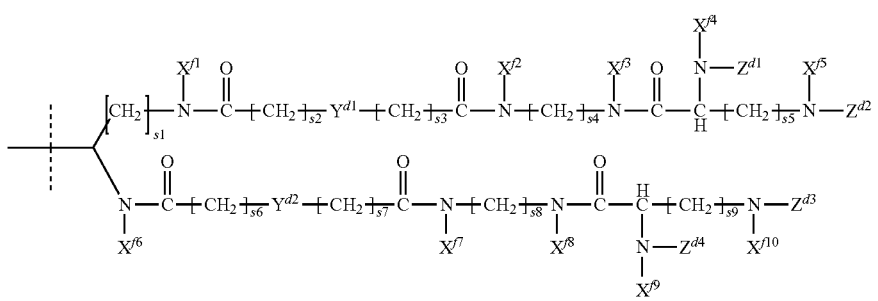
(j-vii)
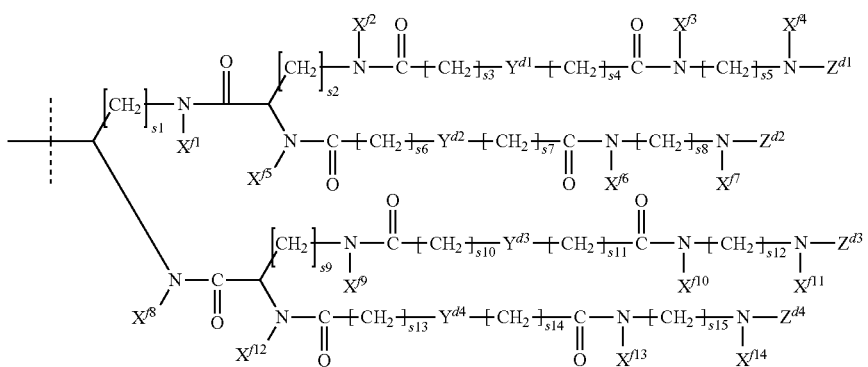

wherein
the dashed line indicates attachment to -L²-;
s1, s2, s3, s4, s5, s6, s7, s8, s9, s10, s11, s12, s13, s14 and s15 are independently of each other selected from 1, 2, 3, 4, 5, 6, 7, 8, 9, 10;

$-X^{d1}$, $-X^{d2}$, $-X^{d3}$ and $-X^{d4}$ are independently of each other selected from the group consisting of $-OH$, $-SH$ and $-NR^{g1}R^{g2}$; preferably $-OH$;

$-X^{e1}$, $-X^{e2}$, $-X^{e3}$ and $-X^{e4}$ are independently of each other selected from the group consisting of $-H$, $C_{1-6}$ alkyl, $C_{2-6}$ alkenyl and $C_{2-6}$ alkynyl;

$-R^{g1}$ and $-R^{g2}$ are independently of each other selected from the group consisting of $-H$, $C_{1-6}$ alkyl, $C_{2-6}$ alkenyl and $C_{2-6}$ alkynyl;

$-X^{f1}$, $-X^{f2}$, $-X^{f3}$, $-X^{f4}$, $-X^{f5}$, $-X^{f6}$, $-X^{f7}$, $-X^{f8}$, $-X^{f9}$, $-X^{f10}$, $-X^{f11}$, $-X^{f12}$, $-X^{f13}$ and $-X^{f14}$ are independently of each other selected from the group consisting of $-H$, $C_{1-6}$ alkyl, $C_{2-6}$ alkenyl and $C_{2-6}$ alkynyl; preferably $-H$;

$-Y^{d1}-$, $-Y^{d2}-$, $-Y^{d3}-$ and $-Y^{d4}-$ are independently of each other selected from the group consisting of

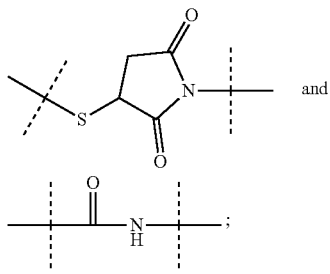

and $-Z^{d1}$, $-Z^{d2}$, $-Z^{d3}$ and $-Z^{d4}$ are independently of each other a protein, in certain embodiments a random coil protein and in certain embodiments, a random coil protein selected from the group consisting of PA, PAS, PAG, PG and XTEN.

In certain embodiments, $-Y^{d1}-$ and $-Y^{d2}-$ of formula (j-iv), (j-v) and (j-vi) and $-Y^{d1}-$, $-Y^{d2}-$, $-Y^{d3}-$ and $-Y^{d4}-$ of formula (j-vii) are

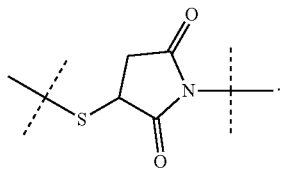

In certain embodiments, $-Y^{d1}-$ and $-Y^{d2}-$ of formula (j-iv), (j-v) and (j-vi) and $-Y^{d1}-$, $-Y^{d2}-$, $-Y^{d3}-$ and $-Y^{d4}-$ of formula (j-vii) are

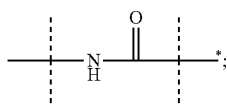

wherein the dashed line marked with the asterisk is oriented towards $-Z^{d1}$, $-Z^{d2}$, $-Z^{d3}$ and $-Z^{d4}$, respectively, and the unmarked dashed line is oriented towards -L²-.

In certain embodiments, $-X^{f1}$, $-X^{f2}$, $-X^{f3}$, $-X^{f4}$, $-X^{f5}$, $-X^{f6}$, $-X^{f7}$ and $-X^{f8}$ of formula (j-i) are $-H$; $-X^{d1}$ and $-X^{d2}$ of formula (j-i) are $-OH$; $-X^{e1}$ and $-X^{e2}$ of formula (j-i) are selected from the group consisting of $-H$ and methyl; and s1, s2, s3 and s4 of formula (j-i) are selected from the group consisting of 2, 3, 4, 5 and 6.

In certain embodiments, $-X^{f1}$, $-X^{f2}$, $-X^{f3}$, $-X^{f4}$, $-X^{f5}$, $-X^{f6}$, $-X^{f7}$ and $-X^{f8}$ of formula (j-i) are $-H$; $-X^{d1}$ and $-X^{d2}$ of formula (j-i) are $-OH$; $-X^{e1}$ and $-X^{e2}$ of formula (j-i) are $-H$; and s1, s2, s3 and s4 of formula (j-i) are 4.

In certain embodiments, $-X^{f1}$, $-X^{f2}$, $-X^{f3}$ and $-X^{f4}$ of formula (j-ii) are $-H$; $-X^{d1}$, $-X^{d2}$, $-X^{d3}$ and $-X^{d2}$ of formula (j-ii) are $-OH$; $-X^{e1}$, $-X^{e2}$, $-X^{e3}$ and $-X^{e4}$ of formula (j-ii) are selected from the group consisting of $-H$ and methyl; s1, s2, s3, s4 and s5 of formula (j-ii) are selected from the group consisting of 1, 2, 3, 4, 5 and 6. In certain embodiments, $-X^{f1}$, $-X^{f2}$, $-X^{f3}$ and $-X^{f4}$ of formula (j-ii) are $-H$; $-X^{d1}$, $-X^{d2}$, $-X^{d3}$ and $-X^{d2}$ of formula (j-ii) are $-OH$; $-X^{e1}$, $-X^{e2}$, $-X^{e3}$ and $-X^{e4}$ of formula (j-ii) are $-H$; s1 is 4 of formula (j-ii) and s2, s3, s4 and s5 of formula (j-ii) are 1.

In certain embodiments, $-X^{f1}$, $-X^{f2}$, $-X^{f3}$, $-X^{f4}$, $-X^{f5}$, $-X^{f6}$, $-X^{f7}$, $-X^{f8}$, $-X^{f9}$ and $-X^{f10}$ of formula (j-iii) are $-H$; $-X^{d1}$, $-X^{d2}$, $-X^{d3}$ and $-X^{d4}$ of formula (j-iii) are $-OH$; $-X^{e1}$, $-X^{e2}$, $-X^{e3}$ and $-X^{e4}$ of formula (j-iii) are selected from the group consisting of $-H$ and methyl; and s1, s2 and s3 of formula (j-iii) are selected from the group consisting of 2, 3, 4, 5 and 6. In certain embodiments, $-X^{f1}$, $-X^{f2}$, $-X^{f3}$, $-X^{f4}$, $-X^{f5}$, $-X^{f6}$, $-X^{f7}$, $-X^{f8}$, $-X^{f9}$ and $-X^{f10}$ of formula (j-iii) are $-H$; $-X^{d1}$, $-X^{d2}$, $-X^{d3}$ and $-X^{d4}$ of formula (j-iii) are $-OH$; $-X^{e1}$, $-X^{e2}$, $-X^{e3}$ and $-X^{e4}$ of formula (j-iii) are $-H$; and s1, s2 and s3 of formula (j-iii) are 4.

In certain embodiments, $-X^{f1}$, $-X^{f2}$, $-X^{f3}$, $-X^{f4}$, $-X^{f5}$ and $-X^{f6}$ of formula (j-iv) are $-H$; s1, s2, s3, s4, s5, s6 and s7 of formula (j-iv) are selected from the group consisting of 1, 2, 3, 4, 5, 6 and 7; $-Y^{d1}-$ and $-Y^{d2}-$ are selected from the group consisting of

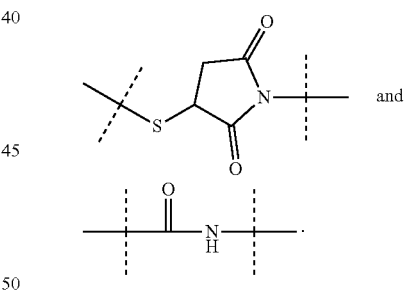

and

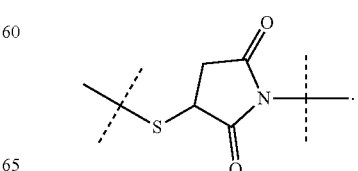

In certain embodiments, $-X^{f1}$, $-X^{f2}$, $-X^{f3}$, $-X^{f4}$, $-X^{f5}$ and $-X^{f6}$ of formula (j-iv) are $-H$; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and $-Y^{d1}-$ and $-Y^{d2}-$ of formula (j-iv) are In certain embodiments, —$X^{f1}$, —$X^{f2}$, —$X^{f3}$, —$X^{f4}$, —$X^{f5}$ and —$X^{f6}$ of formula (j-iv) are —H; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and —$Y^{d1}$— and —$Y^{d2}$— of formula (j-iv) are

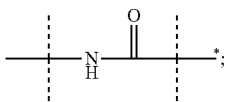

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

In certain embodiments, —$X^{f1}$, —$X^{f2}$, —$X^{f3}$ and —$X^{f4}$ of formula (j-v) are —H; s1, s2, s3, s4 and s5 of formula (j-v) are selected from the group consisting of 1, 2, 3, 4, 5, 6 and 7; —$Y^{d1}$— and —$Y^{d2}$— of formula (j-v) are selected from the group consisting of

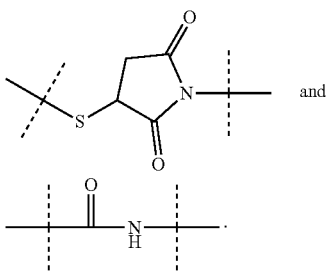

In certain embodiments, —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

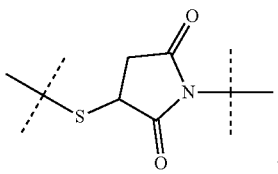

In certain embodiments, —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

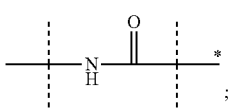

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

In certain embodiments, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1, s2, s3, s4, s5, s6, s7, s8 and s9 of formula (j-vi) are selected from the group consisting of 1, 2, 3, 4, 5, 6 and 7; —$Y^{d1}$— and —$Y^{d2}$— of formula (j-vi) are selected from the group consisting of

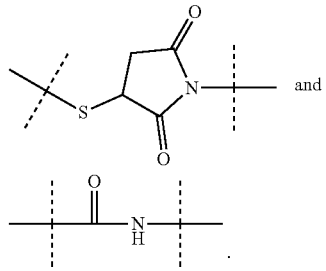

In certain embodiments, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

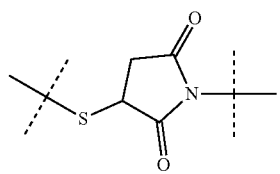

In certain embodiments, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

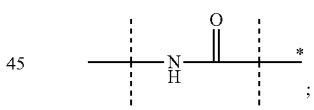

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

In certain embodiments, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; s1, s2, s3, s4, s5, s6, s7, s8, s9, s10, s11, s12, s13, s14 and s15 of formula (j-vii) are selected from the group consisting of 1, 2, 3, 4, 5, 6 and 7; —$Y^{d1}$—, —$Y^{d2}$—, —$Y^{d3}$— and —$Y^{d4}$— of formula (j-vii) are selected from the group consisting of

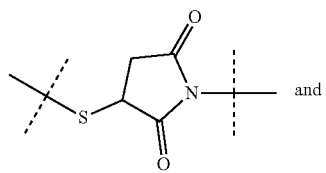

-continued

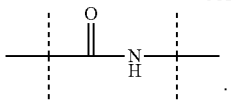

In certain embodiments, $-X^{f1}$, $-X^{f2}$, $-X^{f3}$, $-X^{f4}$, $-X^{f5}$, $-X^{f6}$, $-X^{f7}$, $-X^{f8}$, $-X^{f9}$, $-X^{f10}$, $-X^{f11}$, $-X^{f12}$, $-X^{f13}$ and $-X^{f14}$ of formula (j-vii) are $-H$; are $-H$; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii) is 2 and s5 of formula (j-vii) is 4; and $-Y^{d1}-$, $-Y^{d2}-$, $-Y^{d3}-$ and $-Y^{d4}-$ of formula (j-vii) are

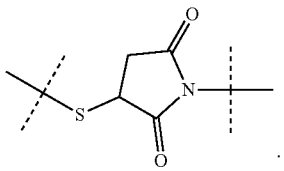

In certain embodiments, $-X^{f1}$, $-X^{f2}$, $-X^{f3}$, $-X^{f4}$, $-X^{f5}$, $-X^{f6}$, $-X^{f7}$, $-X^{f8}$, $-X^{f9}$, $-X^{f10}$, $-X^{f11}$, $-X^{f12}$, $-X^{f13}$ and $-X^{f14}$ of formula (j-vii) are $-H$; are $-H$; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii) is 2 and s15 of formula (j-vii) is 4; and $-Y^{d1}-$, $-Y^{d2}-$, $-Y^{d3}-$ and $-Y^{d4}-$ of formula (j-vii) are

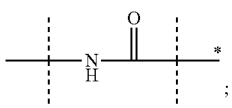

wherein the dashed line marked with the asterisk is oriented towards $-Z^{d1}$, $-Z^{d2}$, $-Z^{d3}$ and $-Z^{d4}$, respectively, and the unmarked dashed line is oriented towards $-L^2-$.

In certain embodiments, $-Z^{d1}$, $-Z^{d2}$, $-Z^{d3}$ and $-Z^{d4}$ of formula (j-i), (j-ii), (j-iii), (j-iv), (j-v), (j-vi) and (j-vii) have the same structure. In certain embodiments, $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PA moiety. In certain embodiments, $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PAS moiety. In certain embodiments, $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PAG moiety. In certain embodiments, $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PC moiety. In certain embodiments, $-Z^{d1}$, $-Z^{d2}$, $-Z^{d3}$ and $-Z^{d4}$ of formula (j-i), (j-ii), G-iii), (j-iv), (j-v), (j-vi) and (j-vii) are a XTEN moiety.

In certain embodiments, the CNP conjugate is of formula (IIf):

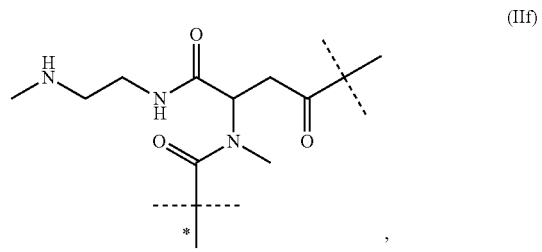
(IIf)

wherein the unmarked dashed line indicates the attachment to a nitrogen of -D which is a CNP moiety by forming an amide bond; and the dashed line marked with the asterisk indicates attachment to $-Z$ having the structure

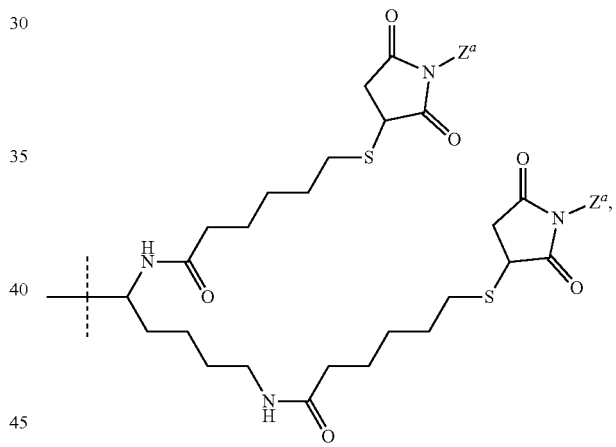

wherein each $-Z^a$ is

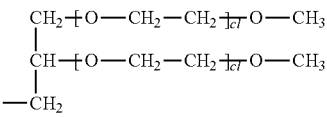

wherein each c1 is an integer independently ranging from 200 to 250.

In certain embodiments, each c1 of formula (IIf) is about 225.

In certain embodiments, the CNP conjugate is of formula (IIf-i)

87

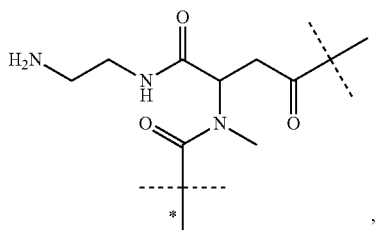
(IIf-i)

wherein
the unmarked dashed line indicates the attachment to a nitrogen of -D which is a CNP moiety by forming an amide bond; and
the dashed line marked with the asterisk indicates attachment to —Z having the structure

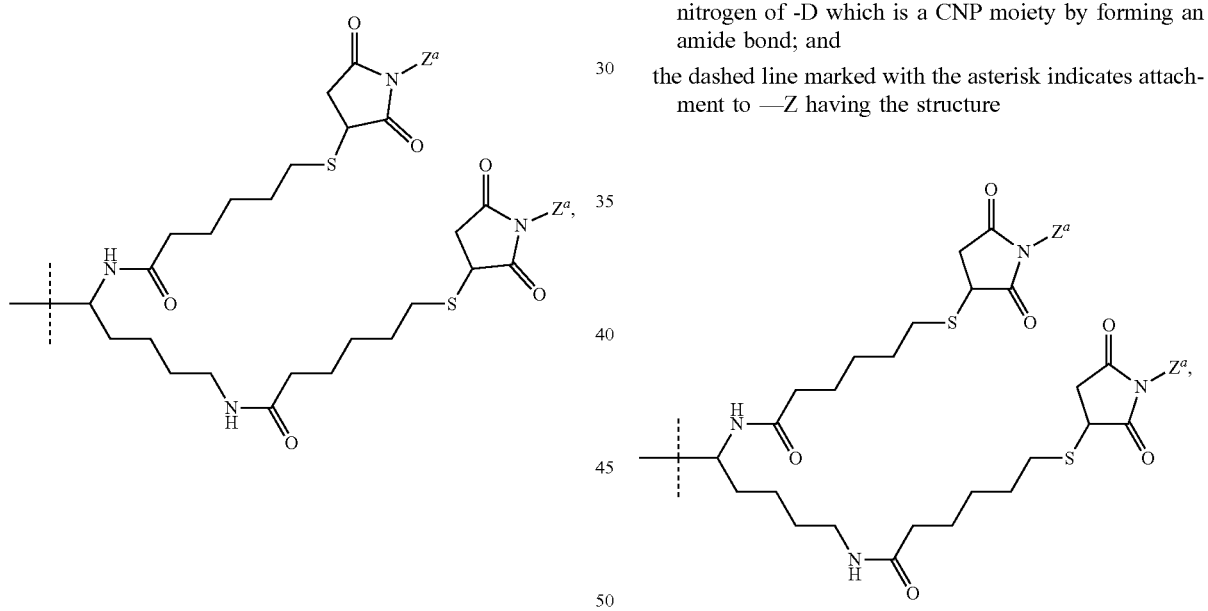

wherein
each —Z$^a$ is

88 wherein
each c1 is an integer independently ranging from 200 to 250.

In certain embodiments, each c1 of formula (IIf-i) is about 225.

In certain embodiments, the CNP conjugate is of formula (IIf-ii):

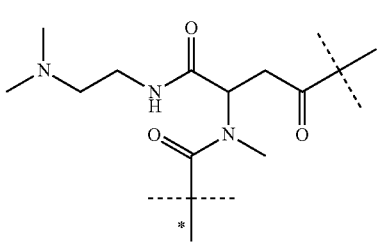
(IIf-ii)

wherein
the unmarked dashed line indicates the attachment to a nitrogen of -D which is a CNP moiety by forming an amide bond; and
the dashed line marked with the asterisk indicates attachment to —Z having the structure

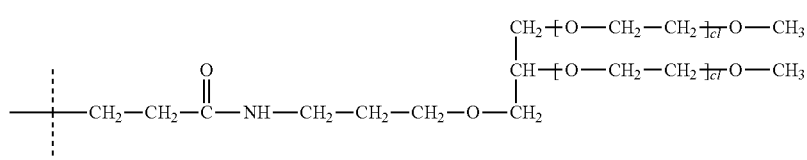

wherein
each —$Z^a$ is

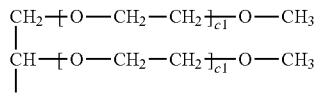
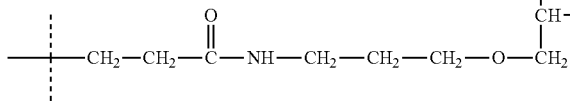

wherein
each c1 is an integer independently ranging from 200 to 250.

In certain embodiments, each c1 of formula (IIf-ii) is about 225.

In certain embodiments, -D of formula (IIf), (IIf-i) and (IIf-ii) is a CNP moiety, i.e. the conjugate of formula (IIf), (IIf-i) and (IIf-ii) is a CNP conjugate. In certain embodiments, -D of formula (IIf), (IIf-i) and (IIf-ii) is a CNP moiety having the sequence of SEQ ID NO:24, SEQ ID NO:25 or SEQ ID NO:30. In certain embodiments, -D of formula (IIf), (IIf-i) and (IIf-ii) is a CNP moiety having the sequence of SEQ ID NO:24. In certain embodiments, -D of formula (IIf), (IIf-i) and (IIf-ii) is a CNP moiety having the sequence of SEQ ID NO:20. In certain embodiments, -D of formula (IIf), (IIf-i) and (IIf-ii) is a CNP moiety having the sequence of SEQ ID NO:21. In certain embodiments, -D of formula (IIf), (IIf-i) and (IIf-ii) is a CNP moiety having the sequence of SEQ ID NO:22. -D of formula (IIf), (IIf-i) and (IIf-ii) is a CNP moiety having the sequence of SEQ ID NO:23. In certain embodiments, -D of formula (IIf), (IIf-i) and (IIf-ii) is a CNP moiety having the sequence of SEQ ID NO:30.

In certain embodiments, -D of formula (IIf), (IIf-i) and (IIf-ii) is a CNP moiety which is attached to -$L^1$- through the nitrogen of the N-terminal amine functional group of CNP.

In certain embodiments, -D of formula (IIf), (IIf-i) and (IIf-ii) is a CNP moiety which is attached to -$L^1$- through a nitrogen provided by the amine functional group of a lysine side chain of the CNP moiety.

In certain embodiments, said lysine side chain is not part of the ring formed by the disulfide bridge between the cysteine residues at positions 22 and 38, if the CNP moiety is of SEQ ID NO:24.

Accordingly, in certain embodiments, the CNP moiety is connected to -$L^1$- in the CNP conjugate of formula (IIf), (IIf-i) and (IIf-ii) through the amine functional group provided by the side chain of the lysine at position 9, if the CNP has the sequence of SEQ ID NO:24.

In certain embodiments, the CNP moiety is connected to -$L^1$- in the CNP conjugate of formula (IIf), (IIf-i) and (IIf-ii) through the amine functional group provided by the side chain of the lysine at position 11, if the CNP has the sequence of SEQ ID NO:24.

In certain embodiments, the CNP moiety is connected to -$L^1$- in the CNP conjugate of formula (IIf), (IIf-i) and (IIf-ii) through the amine functional group provided by the side chain of the lysine at position 15, if the CNP has the sequence of SEQ ID NO:24.

In certain embodiments, the CNP moiety is connected to -$L^1$- in the CNP conjugate of formula (IIf), (IIf-i) and (IIf-ii) through the amine functional group provided by the side chain of the lysine at position 16, if the CNP has the sequence of SEQ ID NO:24.

In certain embodiments, the CNP moiety is connected to -$L^1$- in the CNP conjugate of formula (IIf), (IIf-i) and (IIf-ii) through the amine functional group provided by the side chain of the lysine at position 20, if the CNP has the sequence of SEQ ID NO:24.

In certain embodiments, said lysine side chain is part of the ring formed by the disulfide bridge between the cysteine residues at positions 22 and 38, if the CNP moiety is of SEQ ID NO:24.

Accordingly, in certain embodiments, the CNP moiety is connected to -$L^1$- in the CNP conjugate of formula (IIf) through the amine functional group provided by the side chain of the lysine at position 26, if the CNP has the sequence of SEQ ID NO:24.

In certain embodiments, the CNP conjugate is of formula (IIf-i), wherein c1 is about 225, the CNP moiety has the sequence of SEQ ID NO:24 and is attached to -$L^1$- through the amine functional group provided by the side chain of the lysine at position 26.

In certain embodiments, the CNP conjugate is of formula (IIf), wherein c1 is about 225, -D is a CNP moiety having the sequence of SEQ ID NO:20 and is attached to -$L^1$- through the amine functional group provided by the side chain of the lysine at position 30.

In certain embodiments, the CNP conjugate is of formula (IIf-i), wherein c1 is about 225, -D is a CNP moiety having the sequence of SEQ ID NO:20 and is attached to -$L^1$- through the amine functional group provided by the side chain of the lysine at position 30.

In certain embodiments, the CNP conjugate is of formula (IIf-ii), wherein c1 is about 225, the CNP moiety has the sequence of SEQ ID NO:20 and is attached to -$L^1$- through the amine functional group provided by the side chain of the lysine at position 30.

In certain embodiments, the CNP conjugate is of formula (IIf), wherein c1 is about 225, -D is a CNP moiety having the sequence of SEQ ID NO:21 and is attached to -$L^1$- through the 30 amine functional group provided by the side chain of the lysine at position 29.

In certain embodiments, the CNP conjugate is of formula (IIf-i), wherein c1 is about 225, the CNP moiety has the sequence of SEQ ID NO:21 and is attached to -$L^1$- through the amine functional group provided by the side chain of the lysine at position 29.

In certain embodiments, the CNP conjugate is of formula (IIf-ii), wherein c1 is about 225, the CNP moiety has the sequence of SEQ ID NO:21 and is attached to -$L^1$- through the amine functional group provided by the side chain of the lysine at position 29.

In certain embodiments, the CNP conjugate is of formula (IIf), wherein c1 is about 225, -D is a CNP moiety having the sequence of SEQ ID NO:22 and is attached to -$L^1$- through the amine functional group provided by the side chain of the lysine at position 28.

In certain embodiments, the CNP conjugate is of formula (IIf-i), wherein c1 is about 225, the CNP moiety has the sequence of SEQ ID NO:22 and is attached to -L¹- through the amine functional group provided by the side chain of the lysine at position 28.

In certain embodiments, the CNP conjugate is of formula (IIf-ii), wherein c1 is about 225, the CNP moiety has the sequence of SEQ ID NO:22 and is attached to -L¹- through the amine functional group provided by the side chain of the lysine at position 28.

In certain embodiments, the CNP conjugate is of formula (IIf), wherein c1 is about 225, -D is a CNP moiety having the sequence of SEQ ID NO:23 and is attached to -L¹- through the amine functional group provided by the side chain of the lysine at position 27.

In certain embodiments, the CNP conjugate is of formula (IIf-i), wherein c1 is about 225, the CNP moiety has the sequence of SEQ ID NO:23 and is attached to -L¹- through the amine functional group provided by the side chain of the lysine at position 27.

In certain embodiments, the CNP conjugate is of formula (IIf-ii), wherein c1 is about 225, the 30 CNP moiety has the sequence of SEQ ID NO:23 and is attached to -L¹- through the amine functional group provided by the side chain of the lysine at position 27.

In certain embodiments, the CNP conjugate is of formula (IIf), wherein c1 is about 225, -D is a CNP moiety having the sequence of SEQ ID NO:30 and is attached to -L¹- through the amine functional group provided by the side chain of the lysine at position 27.

In certain embodiments, the CNP conjugate is of formula (IIf-i), wherein c1 is about 225, the CNP moiety has the sequence of SEQ ID NO:30 and is attached to -L¹- through the amine functional group provided by the side chain of the lysine at position 27.

In certain embodiments, the CNP conjugate is of formula (IIf-ii), wherein c1 is about 225, the CNP moiety has the sequence of SEQ ID NO:30 and is attached to -L¹- through the amine functional group provided by the side chain of the lysine at position 27.

In certain embodiments, the CNP conjugate is of formula (IIf-ii), wherein c1 is about 225, the CNP moiety has the sequence of SEQ ID NO:24 and is attached to -L¹- through the amine functional group provided by the side chain of the lysine at position 26.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In certain embodiments, the CNP conjugate is of formula (IIf), wherein c1 is about 225, -D is a CNP moiety having the sequence of SEQ ID NO:24 and is attached to -L¹- through the amine functional group provided by the side chain of the lysine at position 26.

In certain embodiments, the CNP conjugate is of formula (IIf'):

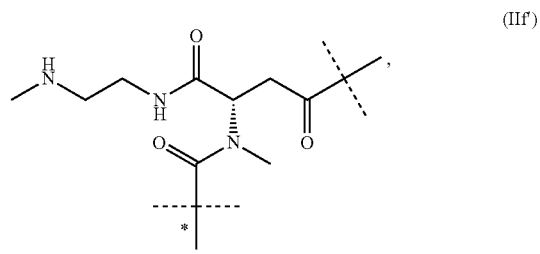

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

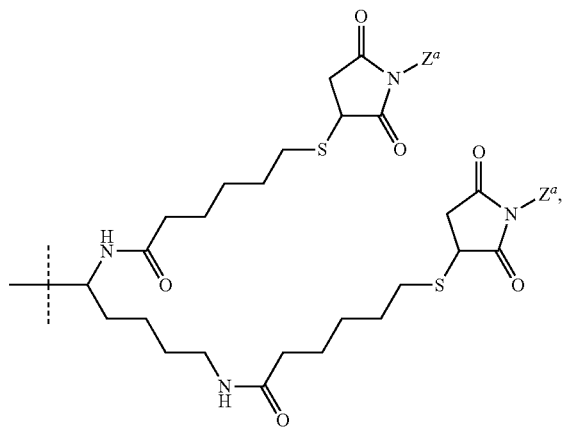

wherein
each $Z^a$ is

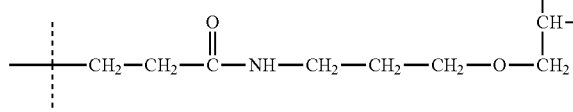
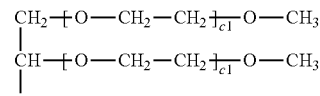

wherein
each c1 is an integer independently ranging from 200 to 250.

In certain embodiments, each c1 of formula (IIf') is about 225.

In certain embodiments, the CNP conjugate is of formula (IIf-i'):

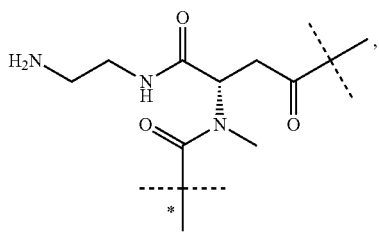
(IIf-i'),

In certain embodiments, each c1 of formula (IIf-i') is about 225.

In certain embodiments, the CNP conjugate is of formula (IIf-ii'):

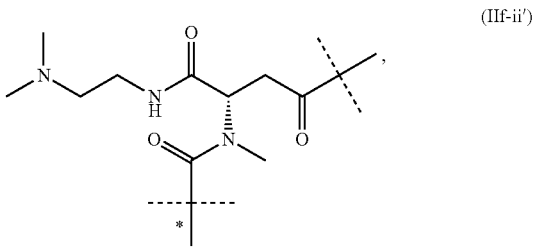
(IIf-ii'), wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

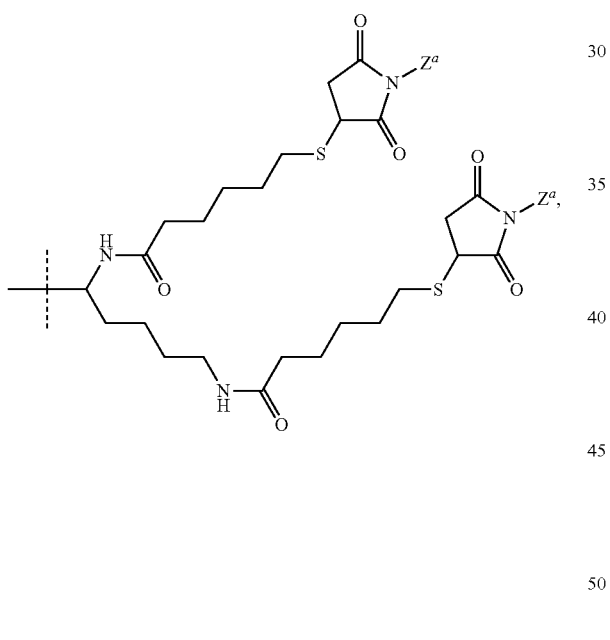

wherein
each $Z^a$ is

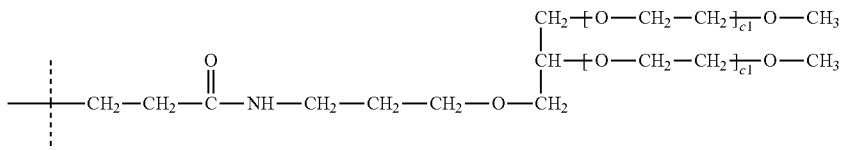

wherein each c1 is an integer independently ranging from 200 to 250.

wherein
each $Z^a$ is

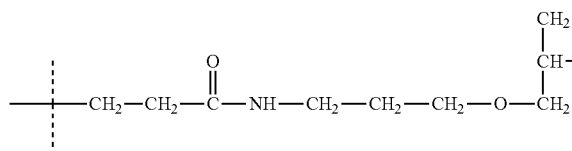

wherein
each c1 is an integer independently ranging from 200 to 250.

In certain embodiments, each c1 of formula (IIf-ii') is about 225.

In certain embodiments, the CNP conjugate is of formula (IIfa):

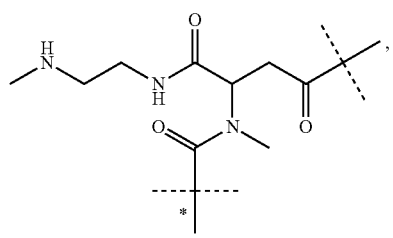

wherein
the unmarked dashed line indicates the attachment to a nitrogen of -D which is a CNP moiety by forming an amide bond; and
the dashed line marked with the asterisk indicates attachment to —Z having the structure

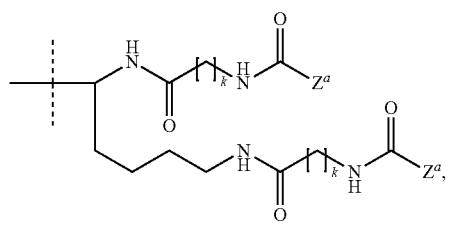

wherein
k is selected from the group consisting of 1, 2, 3, 4, 5, 6, 7, 8, 9, 10, 11 and 12; each —$Z^a$ is

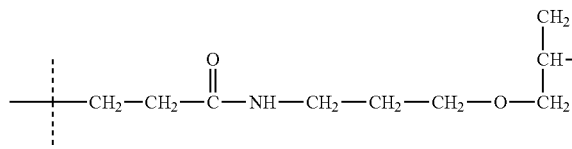

wherein
each c1 is an integer independently ranging from 200 to 250.

In certain embodiments, k of formula (IIfa) is selected from the group consisting of 2, 3, 4, 5, 6 and 7.

In certain embodiments, each c1 of formula (IIfa) is about 225.

In certain embodiments, the CNP conjugate is of formula (IIfa-i):

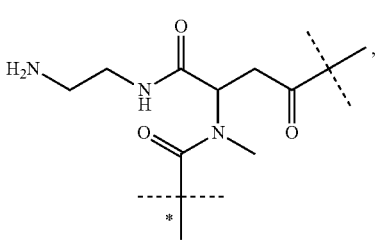

wherein
the unmarked dashed line indicates the attachment to a nitrogen of -D which is a CNP moiety by forming an amide bond; and
the dashed line marked with the asterisk indicates attachment to —Z having the structure

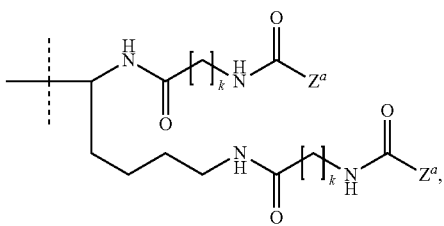

wherein
k is selected from the group consisting of 1, 2, 3, 4, 5, 6, 7, 8, 9, 10, 11 and 12; each —$Z^a$ is

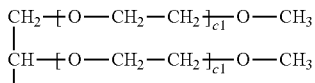

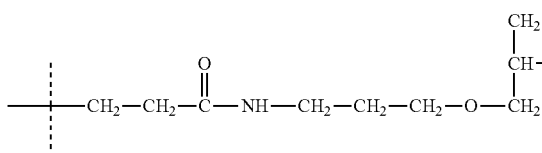

wherein
each c1 is an integer independently ranging from 200 to 250.

In certain embodiments, k of formula (IIfa-i) is selected from the group consisting of 2, 3, 4, 5, 6 and 7.

In certain embodiments, each c1 of formula (IIfa-i) is about 225.

In certain embodiments, the CNP conjugate is of formula (IIfa-ii):

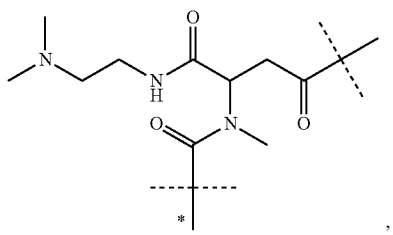

(IIfa-ii)

wherein
the unmarked dashed line indicates the attachment to a nitrogen of -D which is a CNP moiety by forming an amide bond; and
the dashed line marked with the asterisk indicates attachment to —Z having the structure

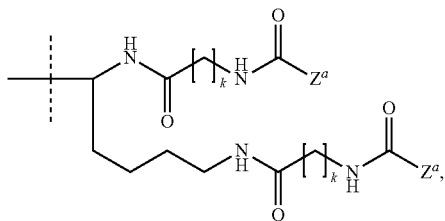

wherein
k is selected from the group consisting of 1, 2, 3, 4, 5, 6, 7, 8, 9, 10, 11 and 12; each —$Z^a$ is

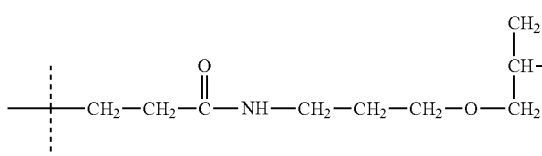

wherein
each c1 is an integer independently ranging from 200 to 250.

In certain embodiments, each c1 of formula (IIfa-ii) is about 225.

In certain embodiments, the CNP moiety of the CNP conjugate of formula (IIfa), (IIfa-i) and (IIfa-ii) has the sequence of SEQ ID NO:25.

In certain embodiments, the CNP moiety of the CNP conjugate of formula (IIfa), (IIfa-i) and (IIfa-ii) has the sequence of SEQ ID NO:20.

In certain embodiments, the CNP moiety of the CNP conjugate of formula (IIfa), (IIfa-i) and (IIfa-ii) has the sequence of SEQ ID NO:21.

In certain embodiments, the CNP moiety of the CNP conjugate of formula (IIfa), (IIfa-i) and (IIfa-ii) has the sequence of SEQ ID NO:22.

In certain embodiments, the CNP moiety of the CNP conjugate of formula (IIfa), (IIfa-i) and (IIfa-ii) has the sequence of SEQ ID NO:23.

In certain embodiments, the CNP moiety of the CNP conjugate of formula (IIfa), (IIfa-i) and (IIfa-ii) has the sequence of SEQ ID NO:30.

In certain embodiments, the CNP moiety of the CNP conjugate of formula (IIfa), (IIfa-i) and (IIfa-ii) has the sequence of SEQ ID NO:24.

In certain embodiments, the CNP moiety is attached to -$L^1$- in the CNP conjugate of formula (IIfa), (IIfa-i) and (IIfa-ii) through the nitrogen of the N-terminal amine functional group of CNP.

In certain embodiments, the CNP conjugate is of formula (IIfa'):

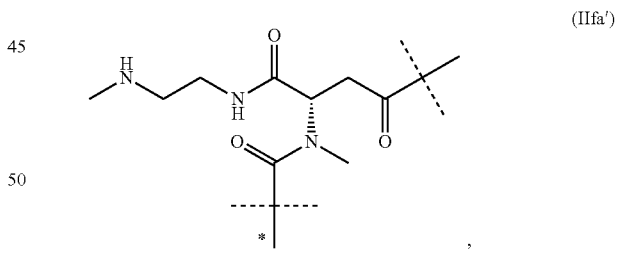

(IIfa')

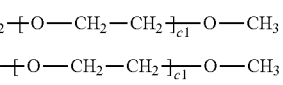

wherein
the unmarked dashed line indicates the attachment to the nitrogen provided by the side chain of the lysine at position 26 of the CNP moiety of SEQ ID NO:24 by forming an amide bond; and the dashed line marked with the asterisk indicates attachment to —Z having the structure

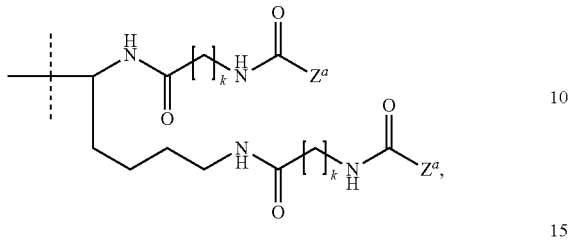

wherein k is selected from the group consisting of 1, 2, 3, 4, 5, 6, 7, 8, 9, 10, 11 and 12; each $Z^a$ is

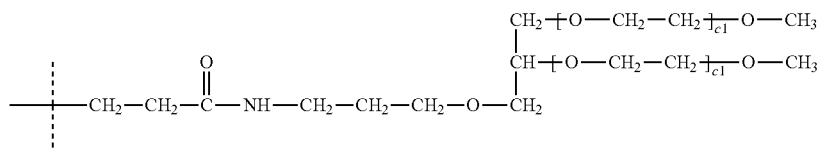

wherein each c1 is an integer independently ranging from 200 to 250.

In certain embodiments, k of formula (IIfa') is selected from the group consisting of 2, 3, 4, 5, 6 and 7.

In certain embodiments, each c1 of formula (IIfa') is about 225.

In certain embodiments, the CNP conjugate is of formula (IIfa-i'):

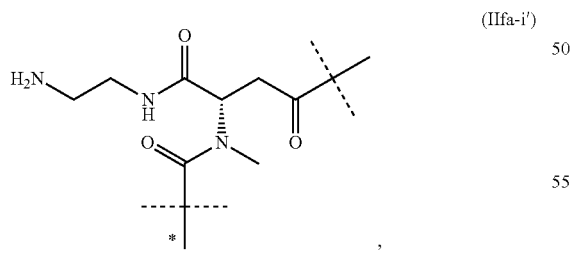

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

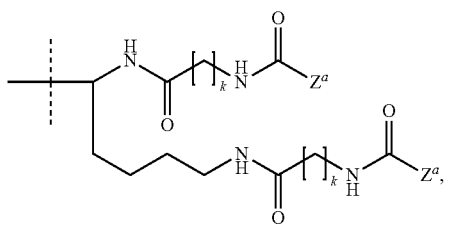

wherein
k is selected from the group consisting of 1, 2, 3, 4, 5, 6, 7, 8, 9, 10, 11 and 12; each $Z^a$ is

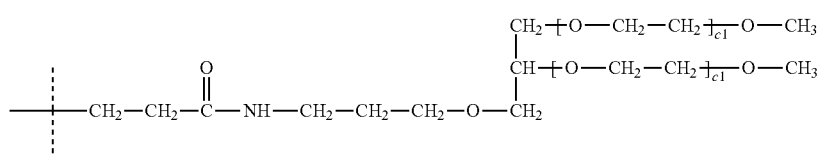

wherein
each c1 is an integer independently ranging from 200 to 250.

In certain embodiments, k of formula (IIfa-i') is selected from the group consisting of 2, 3, 4, 5, 6 and 7.

In certain embodiments, each c1 of formula (IIfa-i') is about 225.

In certain embodiments, the CNP conjugate is of formula (IIfa-ii'):

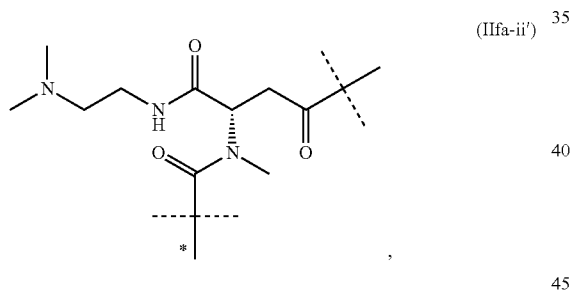

(IIfa-ii')

wherein
the unmarked dashed line indicates the attachment to a nitrogen provided by the side chain of the lysine at position 26 of the CNP moiety of SEQ ID NO:24 by forming an amide bond; and
the dashed line marked with the asterisk indicates attachment to —Z having the structure

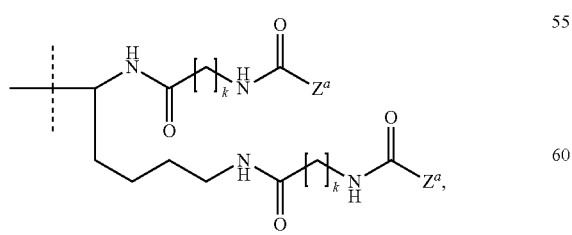

wherein
k is selected from the group consisting of 1, 2, 3, 4, 5, 6, 7, 8, 9, 10, 11 and 12; each $Z^a$ is

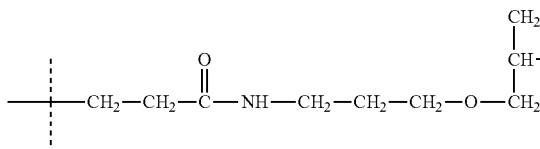
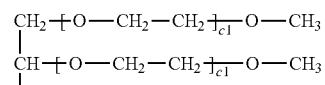

wherein
each c1 is an integer independently ranging from 200 to 250.

In certain embodiments, k of formula (IIfa-ii') is selected from the group consisting of 2, 3, 4, 5, 6 and 7.

In certain embodiments, each c1 of formula (IIfa-ii') is about 225.

In certain embodiments, the dry pharmaceutical formulation of the present invention may comprise one or more further excipients, such as for example, a preservative, stabilizer, anti-adsorption agent, cryoprotectant, oxidation protection agent and other auxiliary agents. It is understood that one excipient may have multiple, such as dual or triple, functions.

In certain embodiments, the dry pharmaceutical formulation of the present invention may comprise a preservative, such as a preservative selected from the group consisting of benzoic acid, phenol, methylparaben, ethylparaben, propylparaben, butylparaben, potassium sorbate, chlorobutanol, benzyl alcohol, phenylmercuric nitrate, thimerosal, sorbic acid, potassium sorbate, chlorocresol, benzalkonium chloride, 2-ethoxyethanol, chlorhexidine, chlorobutanol, phenylethyl alcohol, phenylmercuric acetate, m-cresol and mixtures thereof.

In certain embodiments, the dry pharmaceutical formulation of the present invention may comprise a stabilizer, such as a stabilizer selected from the group consisting of alanine; arginine; aspartic acid; glycine; histidine; lysine; proline; sugars such as glucose, sucrose, trehalose; polyols such as glycerol, mannitol, sorbitol; salts such as potassium phosphate, sodium sulphate; chelating agents such as EDTA, hexaphosphate; ligands such as divalent metal ions; other salts or organic molecules such as phenolic derivatives; oligomers or polymers such as cyclodextrins, dextran, dendrimers, PEG, PVP, protamine and HSA.

In certain embodiments, the dry pharmaceutical formulation of the present invention may comprise an anti-adsorption agent, such as an anti-adsoption agent selected from the group consisting of ionic or non-ionic surfactants or other proteins or soluble polymers that are used to coat or adsorb competitively to the inner surface of the formulation or formulation's container such as poloxamer (Pluronic F-68), PEG dodecyl ether (Brij 35), dextran, polyethylene glycol, PEG-polyhistidine, BSA, HSA and gelatines. Chosen concentration and type of excipient depends on the effect to be avoided but typically a monolayer of surfactant is formed at the interface just above the CMC.

In certain embodiments, the dry pharmaceutical formulation of the present invention may comprise a cryoprotectant, such as a cryoprotectant selected from the group consisting of sugars, polyols, surfactants, amino acids, non-aqueous solvents and peptides. During freeze- or spray drying, cryoprotectants may counteract the destabilising effects caused by hydrogen bond breaking and water removal. Trehalose is particulary efficient at reducing moisture-induced aggregation and also improves thermal stability potentially caused by exposure of the compound's hydrophobic groups to water. Mannitol and sucrose may also be used, either as sole lyo/cryoprotectant or in combination with each other where higher ratios of mannitol:sucrose are known to enhance physical stability of a compound in a dry pharmaceutical formulation. Mannitol may also be combined with trehalose. Trehalose may also be combined with sorbitol or sorbitol may be used as the sole protectant. Starch or starch derivatives may also be used.

In certain embodiments, the dry pharmaceutical formulation of the present invention may comprise an oxidation protection agent such as an oxidation protection agent selected from the group consisting of methionine, butylhydroxytoluene, butylhydroxyanisol, tocopherol, propylgallate, ascorbic acid, sodium bisulfite, ethylenediaminetetraacetic acid (EDTA), cysteine, glutathione, monothioglycerol, poly(ethylenimine), vitamin E, ectoine, morin and mixtures thereof. In certain embodiments, the dry pharmaceutical formulation of the present invention may comprise an oxidation protection agent such as an oxidation protection agent selected from the group consisting of methionine, butylhydroxytoluene, butylhydroxyanisol, tocopherol, propylgallate, ascorbic acid, ethylenediaminetetraacetic acid (EDTA), poly(ethylenimine), vitamin E, ectoine, morin and mixtures thereof.

In certain embodiments, the dry pharmaceutical formulation of the present invention may comprise further excipients selected from the group consisting of wetting agents, viscosity modifiers and antibiotics.

In certain embodiments, the dry pharmaceutical formulation of the present invention comprises a CNP conjugate, succinic acid, trehalose and Tris.

In certain embodiments the dry pharmaceutical formulation according to the present invention comprises based on the total weight of the dry pharmaceutical formulation:

| | |
|---|---|
| CNP conjugate | 1.3-45.4% (w/w) |
| succinic acid | 0.2-3.2% (w/w) |
| trehalose dihydrate | 52.6-98.4% (w/w) |
| Tris | 0.1-5.6% (w/w). |

In certain embodiments the dry pharmaceutical formulation according to the present invention comprises based on the total weight of the dry pharmaceutical formulation:

| | |
|---|---|
| CNP conjugate | 1.3-38.7% (w/w) |
| succinic acid | 0.2-3.2% (w/w) |
| trehalose dihydrate | 52.6-98.4% (w/w) |
| Tris | 0.1-5.6% (w/w). |

Due to high differences in patients' weight range, such as for example 3-60 kg, it is in certain embodiments beneficial to have dry pharmaceutical formulations with different strengths, meaning different concentrations, of CNP conjugate, such as high, medium and low strengths. Thus, in one embodiment the dry pharmaceutical formulation is provided in more than one concentration, such as in two different concentrations, such as in three different concentrations, such as in four different concentrations, such as in five different concentrations, such as in six different concentrations, such as in seven different concentrations, such as in eight different concentrations, such as in nine different concentrations, such as in ten different concentrations, such as in eleven different concentrations, such as in twelve different concentrations.

In certain embodiments, the dry pharmaceutical formulation comprises based on the total weight of the dry pharmaceutical formulation:

| CNP conjugate | 23.8-38.7% (w/w) |
|---|---|
| succinic acid | 0.2-3.1% (w/w) |
| trehalose dihydrate | 52.6-75.9% (w/w) |
| Tris | 0.1-5.6% (w/w). |

In certain embodiments, the dry pharmaceutical formulation comprises based on the total weight of the dry pharmaceutical formulation:

| CNP conjugate | 5.8-12.4% (w/w) |
|---|---|
| succinic acid | 0.3-3.2% (w/w) |
| trehalose dihydrate | 78.8-93.8% (w/w) |
| Tris | 0.1-5.6% (w/w). |

In certain embodiments, the dry pharmaceutical formulation comprises based on the total weight of the dry pharmaceutical formulation:

| CNP conjugate | 1.4-3.7% (w/w) |
|---|---|
| succinic acid | 0.3-3.2% (w/w) |
| trehalose dihydrate | 87.5-98.2% (w/w) |
| Tris | 0.1-5.6% (w/w). |

In certain embodiments, the dry pharmaceutical formulation comprises based on the total weight of the dry pharmaceutical formulation:

| CNP conjugate | 28.8-33.2% (w/w) |
|---|---|
| succinic acid | 0.6-1.6% (w/w) |
| trehalose dihydrate | 62.4-70.4% (w/w) |
| Tris | 0.2-2.8% (w/w). |

In certain embodiments, the dry pharmaceutical formulation comprises based on the total weight of the dry pharmaceutical formulation:

| CNP conjugate | 7.4-8.8% (w/w) |
|---|---|
| succinic acid | 0.8-2.0% (w/w) |
| trehalose dihydrate | 85.7-91.6% (w/w) |
| Tris | 0.2-3.5% (w/w). |

In certain embodiments, the dry pharmaceutical formulation comprises based on the total weight of the dry pharmaceutical formulation:

| CNP conjugate | 2.0-2.5% (w/w) |
|---|---|
| succinic acid | 0.8-2.1% (w/w) |
| trehalose dihydrate | 91.7-97.0% (w/w) |
| Tris | 0.2-3.8% (w/w). |

In certain embodiments, the dry pharmaceutical formulation comprises based on the total weight of the dry pharmaceutical formulation:

| CNP conjugate | 32.2-34.0% (w/w) |
|---|---|
| succinic acid | 0.9-1.0% (w/w) |
| trehalose dihydrate | 64.5-65.5% (w/w) |
| Tris | 0.5-1.4% (w/w). |

In certain embodiments, the dry pharmaceutical formulation comprises based on the total weight of the dry pharmaceutical formulation:

| CNP conjugate | 8.3-8.9% (w/w) |
|---|---|
| succinic acid | 1.2-1.3% (w/w) |
| trehalose dihydrate | 88.6-89.1% (w/w) |
| Tris | 0.7-1.8% (w/w). |

In certain embodiments, the dry pharmaceutical formulation comprises based on the total weight of the dry pharmaceutical formulation:

| CNP conjugate | 2.3-2.4% (w/w) |
|---|---|
| succinic acid | 1.3-1.4% (w/w) |
| trehalose dihydrate | 94.4-95.6% (w/w) |
| Tris | 0.7-1.9% (w/w). |

In certain embodiments, the dry pharmaceutical formulation comprises, based on the total weight of the dry pharmaceutical formulation, about 45.4% (w/w) CNP conjugate, about 0.9% (w/w) succinic acid, about 52.6% (w/w) trehalose dihydrate and about 1.1% (w/w) Tris.

In certain embodiments, the dry pharmaceutical formulation comprises, based on the total weight of the dry pharmaceutical formulation, 45.4% (w/w) CNP conjugate, 0.9% (w/w) succinic acid, 52.6% (w/w) trehalose dihydrate and 1.1% (w/w) Tris.

In certain embodiments, the dry pharmaceutical formulation comprises, based on the total weight of the dry pharmaceutical formulation, about 32.6% (w/w) CNP conjugate, about 1.0% (w/w) succinic acid, about 65.2% (w/w) trehalose dihydrate and about 1.2% (w/w) Tris.

In certain embodiments, the dry pharmaceutical formulation comprises, based on the total weight of the dry pharmaceutical formulation, 33% (w/w) CNP conjugate, 1% (w/w) succinic acid, 65% (w/w) trehalose dihydrate and 1% (w/w) Tris.

In certain embodiments, the dry pharmaceutical formulation comprises, based on the total weight of the dry pharmaceutical formulation, 32.6% (w/w) CNP conjugate, 1.0% (w/w) succinic acid, 65.2% (w/w) trehalose dihydrate and 1.2% (w/w) Tris.

In certain embodiments, the dry pharmaceutical formulation comprises, based on the total weight of the dry pharmaceutical formulation, about 8.2% (w/w) CNP conjugate, about 1.2% (w/w) succinic acid, about 89.1% (w/w) trehalose dihydrate and about 1.5% (w/w) Tris.

In certain embodiments, the dry pharmaceutical formulation comprises, based on the total weight of the dry pharmaceutical formulation, 8% (w/w) CNP conjugate, 1% (w/w) succinic acid, 89% (w/w) trehalose dihydrate and 2% (w/w) Tris.

In certain embodiments, the dry pharmaceutical formulation comprises, based on the total weight of the dry pharmaceutical formulation, 8.2% (w/w) CNP conjugate, 1.2% (w/w) succinic acid, 89.1% (w/w) trehalose dihydrate and 1.5% (w/w) Tris.

In certain embodiments, the dry pharmaceutical formulation comprises, based on the total weight of the dry pharmaceutical formulation, about 2.3% (w/w) CNP conjugate, about 1.3% (w/w) succinic acid, about 94.9% (w/w) trehalose dihydrate and about 1.6% (w/w) Tris.

In certain embodiments, the dry pharmaceutical formulation comprises, based on the total weight of the dry pharmaceutical formulation, 2% (w/w) CNP conjugate, 1% (w/w) succinic acid, 95% (w/w) trehalose dihydrate and 2% (w/w) Tris.

In certain embodiments, the dry pharmaceutical formulation comprises, based on the total weight of the dry pharmaceutical formulation, 2.3% (w/w) CNP conjugate, 1.3% (w/w) succinic acid, 94.9% (w/w) trehalose dihydrate and 1.6% (w/w) Tris.

The dry pharmaceutical formulation of the present invention is a dried pharmaceutical formulation that is stable for at least 6 months, such as for at least 7 months, such as for at least 8 months, such as for at least 9 months, such as for at least 10 months, such as at least 11 months, such as at least 12 months. In certain embodiments, the dry pharmaceutical formulation is stable for at least 14 months, such as for at least 16 months, such as at least 18 months, such as at least 20 months, such as at least 22 months, such as at least 24 months, such as at least 40 months, such as at least 60 months.

In certain embodiments, the dry pharmaceutical formulation of the present invention is stored at temperatures ranging from −80° C. up to 25° C., such as −20° C. up to 25° C., such as −15° C. up to 25° C., such as as −10° C. up to 25° C., such as −5° C. up to 5° C., −5° C. up to 25° C., such as 0° C. up to 5° C., such as 0° C. up to 25° C., such as 2° C. up to 10° C. or such as 4° C. up to 8° C. In certain embodiments, the dry pharmaceutical formulation is stored at 2° C. In certain embodiments, the dry pharmaceutical formulation is stored at 5° C. In certain embodiments, the dry pharmaceutical formulation is stored at 6° C. In certain embodiments, the dry pharmaceutical formulation is stored at 8° C. In certain embodiments, the dry pharmaceutical formulation is stored at 10° C. In certain embodiments, the dry pharmaceutical formulation is stored at 16° C. In certain embodiments, the dry pharmaceutical formulation is stored at 20° C. In certain embodiments, the dry pharmaceutical formulation is stored at 25° C. In certain embodiments, the dry pharmaceutical formulation is stored at 30° C. In certain embodiments, the dry pharmaceutical formulation is stored at 40° C.

In certain embodiments, the dry pharmaceutical formulation is stable for at least 12 months when stored at 0 to 10° C. In certain embodiments, the dry pharmaceutical formulation is stable for at least 12 months when stored at 2 to 10° C. In certain embodiments, the dry pharmaceutical formulation is stable for at least 12 months when stored at 4 to 8° C. In certain embodiments, the dry pharmaceutical formulation is stable for at least 12 months when stored at 5° C.

In certain embodiments, the dry pharmaceutical formulation is stable for at least 24 months when stored at 5° C. In certain embodiments, the dry pharmaceutical formulation is stable for at least 36 months when stored at 5° C. In certain embodiments, the dry pharmaceutical formulation is stable for at least 48 months when stored at 5° C. In certain embodiments, the dry pharmaceutical formulation is stable for at least 60 months when stored at 5° C.

In certain embodiments, the dry pharmaceutical formulation is stable for 6 months when stored at 25° C. In certain embodiments, the dry pharmaceutical formulation is stable for at least 6 months when stored at 25° C. In certain embodiments, the dry pharmaceutical formulation is stable for at least 12 months when stored at 25° C.

In certain embodiments, the dry pharmaceutical formulation is stable for 6 months when stored at 30° C. In certain embodiments, the dry pharmaceutical formulation is stable for at least 6 months when stored at 30° C. In certain embodiments, the dry pharmaceutical formulation is stable for at least 12 months when stored at 30° C.

In certain embodiments, the dry pharmaceutical formulation is stable for 6 months when stored at 40° C. In certain embodiments, the dry pharmaceutical formulation is stable for at least 6 months when stored at 40° C. In certain embodiments, the dry pharmaceutical formulation is stable for at least 12 months when stored at 40° C.

In certain embodiments, the dry pharmaceutical formulation of the present invention is provided as a single dose, meaning that a container comprising the dry pharmaceutical formulation of CNP conjugate comprises one therapeutic dose.

The preferred method of drying is lyophilization, meaning that the pharmaceutical formulation is a lyophilized pharmaceutical formulation.

Another aspect of the present invention is a method of manufacturing the dry pharmaceutical formulation according to the present invention, wherein the method comprises the steps of (i) admixing the CNP conjugate with at least a buffering agent and a bulking agent;
(ii) adjusting the pH of the admixture of step (i);
(iii) optionally, filtering the admixture from step (ii);
(iv) transferring amounts of the admixture from step (ii) or (iii) equivalent to the desired number of dosages into a container;
(v) drying the admixture;
(vi) sealing the container; and
wherein the order of steps (ii) and (iii) may optionally be reversed.

It is understood that during the drying step (v) of the admixture, the bulking agent may become a lyoprotectant.

In certain embodiments, steps (ii) and (iii) are not reversed.

In certain embodiments, the CNP conjugate in step (i) is admixed with a buffering agent and a bulking agent.

The number of dosages transferred into a container in step (iv) may be at least one, such as 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or may be larger than 30.

In certain embodiments, the method of manufacturing the dry pharmaceutical formulation according to the present invention comprises the steps of (i) admixing the CNP conjugate with at least succinic acid and trehalose dihydrate to yield a formulation comprising

| | |
|---|---|
| CNP conjugate | 0.9-82.1 mg/ml |
| succinic acid | 1.3-57.6 mM |
| trehalose dihydrate | 67-111.6 mg/ml, |

(ii) adjusting the pH of the admixture of step (i) to a pH ranging from pH 4.0 to pH 6.0;
(iii) optionally, filtering the admixture from step (ii);
(iv) transferring amounts of the admixture from step (ii) or (iii) equivalent to the desired number of dosages into a container;
(v) drying the admixture;
(vi) sealing the container; and
wherein the order of steps (ii) and (iii) may optionally be reversed.

In certain embodiments, steps (ii) and (iii) are not reversed.

In certain embodiments, in step (ii) the pH of the admixture of step (i) is adjusted with Tris.

In certain embodiments, the CNP conjugate in step (i) is admixed with succinic acid and trehalose dihydrate to yield a formulation comprising

| | |
|---|---|
| CNP conjugate | 0.9-82.1 mg/ml |
| succinic acid | 1.3-57.6 mM |
| trehalose dihydrate | 67-111.6 mg/ml. |

In certain embodiments, the formulation in step (i) comprises

| | |
|---|---|
| CNP conjugate | 19.8-73.6 mg/ml |
| succinic acid | 1.7-50 mM |
| trehalose dihydrate | 63-100 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 19.8-73.6 mg/ml |
| succinic acid | 1.7-50 mM |
| trehalose dihydrate | 56-100 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 4.2-16.5 mg/ml |
| succinic acid | 1.7-36.4 mM |
| trehalose dihydrate | 67-105 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 1.0-4.4 mg/ml |
| succinic acid | 1.7-33 mM |
| trehalose dihydrate | 67-105 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 27.5-50.5 mg/ml |
| succinic acid | 5.1-20.3 mM |
| trehalose dihydrate | 67-95 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 5.8-10.8 mg/ml |
| succinic acid | 5.1-20.3 mM |
| trehalose dihydrate | 72-105 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 1.5-2.9 mg/ml |
| succinic acid | 5.1-20.3 mM |
| trehalose dihydrate | 73-105 mg/ml | and wherein in step (ii) the pH is adjusted to a pH ranging from pH 4.0 to pH 6.0.

In certain embodiments, the formulation in step (i) comprises

| | |
|---|---|
| CNP conjugate | 37.4-42.9 mg/ml |
| succinic acid | 9.3-10.2 mM |
| trehalose dihydrate | 71-87 mg/ml | and wherein in step (ii) the pH is adjusted to a pH ranging from pH 4.5 to pH 5.5.

In certain embodiments, the formulation in step (i) comprises

| | |
|---|---|
| CNP conjugate | 7.5-9.1 mg/ml |
| succinic acid | 9.3-11 mM |
| trehalose dihydrate | 75-97 mg/ml | and wherein in step (ii) the pH is adjusted to a pH ranging from pH 4.5 to pH 5.5.

In certain embodiments, the formulation in step (i) comprises

| | |
|---|---|
| CNP conjugate | 1.9-2.4 mg/ml |
| succinic acid | 9.3-11 mM |
| trehalose dihydrate | 77-97 mg/ml | and wherein in step (ii) the pH is adjusted to pH ranging from pH 4.5 to pH 5.5.

In certain embodiments, the formulation in step (i) comprises about 60.4 mg/ml CNP conjugate, about 10 mM succinic acid, about 70 mg/ml trehalose dihydrate and in step (ii) the pH is adjusted to a pH of 5.

In certain embodiments, the formulation in step (i) comprises 60.4 mg/ml CNP conjugate, 10 mM succinic acid, 70 mg/ml trehalose dihydrate and in step (ii) the pH is adjusted to a pH of 5.

In certain embodiments, the formulation in step (i) comprises about 39.6 mg/ml CNP conjugate, about 10 mM succinic acid, about 79.0 mg/ml trehalose dihydrate and in step (ii) the pH is adjusted to a pH of 5.

In certain embodiments, the formulation in step (i) comprises 40 mg/ml CNP conjugate, 10 mM succinic acid, 79 mg/ml trehalose dihydrate and in step (ii) the pH is adjusted to a pH of 5.

In certain embodiments, the formulation in step (i) comprises 39.6 mg/ml CNP conjugate, 10 mM succinic acid, 79.0 mg/ml trehalose dihydrate and in step (ii) the pH is adjusted to a pH of 5.

In certain embodiments, the formulation in step (i) comprises about 8.2 mg/ml CNP conjugate, about 10 mM succinic acid, about 89.0 mg/ml trehalose dihydrate and in step (ii) the pH is adjusted to a pH of 5.

In certain embodiments, the formulation in step (i) comprises 8 mg/ml CNP conjugate, 10 mM succinic acid, 89 mg/ml trehalose dihydrate and in step (ii) the pH is adjusted to a pH of 5.

In certain embodiments, the formulation in step (i) comprises 8.2 mg/ml CNP conjugate, 10 mM succinic acid, 89.0 mg/ml trehalose dihydrate and in step (ii) the pH is adjusted to a pH of 5.

In certain embodiments, the formulation in step (i) comprises about 2.2 mg/ml CNP conjugate, about 10 mM succinic acid, about 89.5 mg/ml trehalose dihydrate and in step (ii) the pH is adjusted to a pH of 5.

In certain embodiments, the formulation in step (i) comprises 2 mg/ml CNP conjugate, 10 mM succinic acid, 90 mg/ml trehalose dihydrate and in step (ii) the pH is adjusted to a pH of 5.

In certain embodiments, the formulation in step (i) comprises 2.2 mg/ml CNP conjugate, 10 mM succinic acid, 89.5 mg/ml trehalose dihydrate and in step (ii) the pH is adjusted to a pH of 5.

Prior to applying the dry pharmaceutical formulation of the present invention to a patient in need thereof, the dry pharmaceutical formulation is reconstituted. Reconstitution of the dry pharmaceutical formulation into a reconstituted formulation is done by adding a predefined amount of reconstitution solution to the dry pharmaceutical formulation. Therefore, a further aspect of the present invention is a method of reconstituting the dry pharmaceutical formulation of the present invention wherein the method comprises the step of
(a) contacting the dry pharmaceutical formulation of the present invention with a reconstitution solution.

Another aspect of the present invention is a reconstituted pharmaceutical formulation obtainable from the method of reconstituting the dry pharmaceutical formulation of the present invention.

It is understood that the bulking agent of the dry pharmaceutical formulation of the present invention fulfils its bulking function only in the dry pharmaceutical formulation, i.e. not in the reconstituted pharmaceutical formulation and that upon reconstitution of the dry pharmaceutical formulation the bulking agent fulfils the function of an isotonicity agent.

Reconstitution may take place in the container in which the dry pharmaceutical formulation comprising CNP conjugate is provided, such as in a vial; syringe, such as a dual-chamber syringe; ampoule; cartridge, such as a dual-chamber cartridge; or the dry pharmaceutical formulation may be transferred to a different container and is then reconstituted.

In certain embodiments, the container in which the reconstitution of the dry pharmaceutical formulation takes place is a vial.

In certain embodiments, the container in which the reconstitution of the dry pharmaceutical formulation takes place is a syringe. In certain embodiments, the container in which the reconstitution of the dry pharmaceutical formulation takes place is a dual-chamber syringe. In certain embodiments, the container in which the reconstitution of the dry pharmaceutical formulation takes place is a cartridge. In certain embodiments, the container in which the reconstitution of the dry pharmaceutical formulation takes place is a dual-chamber cartridge.

In certain embodiments, the dry pharmaceutical formulation according to the present invention is provided in a first chamber of the dual-chamber syringe and the reconstitution solution is provided in a second chamber of the dual-chamber syringe.

In certain embodiments, the dry pharmaceutical formulation according to the present invention is provided in a first chamber of the dual-chamber cartridge and the reconstitution solution is provided in a second chamber of the dual-chamber cartridge.

Another aspect of the present invention refers to a container comprising the dry pharmaceutical formulation or the reconstituted formulation of the present invention.

It was found that the reconstitution time of the dry pharmaceutical formulations is suitable for a therapeutic setting. In certain embodiments, the addition of a surfactant, such as polysorbate 20 or polysorbate 80 to the formulations comprising the CNP conjugate, increases the reconstitution time of the dry pharmaceutical formulation. Accordingly, in certain embodiments, the dry pharmaceutical formulation according to the present invention does not comprise a surfactant, such as for example polysorbate 20 or polysorbate 80.

The reconstitution solution is a sterile liquid, such as water or buffer, which may comprise further additives, such as preservatives and/or antimicrobials.

In certain embodiments, the reconstituted solution comprises one or more preservative and/or antimicrobial and/or antioxidant.

In certain embodiments, the reconstituted solution comprises one or more preservative.

The preservative may be selected from the group consisting of m-cresol, benzoic acid, phenol, methylparaben, ethylparaben, propylparaben, butylparaben, potassium sorbate, chlorobutanol, benzyl alcohol, phenylmercuric nitrate, thimerosal, sorbic acid, potassium sorbate, chlorocresol, benzalkonium chloride, 2-ethoxyethanol, chlorhexidine, chlorobutanol, phenylethyl alcohol, phenylmercuric acetate and mixtures thereof.

In certain embodiments, the preservative is m-cresol. In certain embodiments, the preservative is benzylalcohol. In certain embodiments, the preservative is benzoic acid. In certain embodiments, the preservative is phenol. In certain embodiments, the preservative is methylparaben. In certain embodiments, the preservative is ethylparaben. In certain embodiments, the preservative is propylparaben. In certain embodiments, the preservative is butylparaben. In certain embodiments, the preservative is potassium sorbate. In certain embodiments, the preservative is benzyl alcohol. In certain embodiments, the preservative is phenylmercuric nitrate. In certain embodiments, the preservative is thimerosal. In certain embodiments, the preservative is sorbic acid. In certain embodiments, the preservative is potassium sorbate. In certain embodiments, the preservative is chlorocresol. In certain embodiments, the preservative is benzalkonium chloride. In certain embodiments, the preservative is 2-ethoxyethanol. In certain embodiments, the preservative is chlorhexidine. In certain embodiments, the preservative is chlorbutanol. In certain embodiments, the preservative is phenylethyl alcohol. In certain embodiments, the preservative is phenylmercuric acetate.

In certain embodiments, the preservative has a concentration ranging from 1 to 10 mg/ml. In certain embodiments, the preservative has a concentration ranging from 1.5 to 3.5 mg/ml. In certain embodiments, the preservative has a concentration ranging from 2 to 3 mg/ml.

The antioxidant may be selected from the group consisting of methionine, butylhydroxytoluene, butylhydroxyanisol, tocopherol, propylgallate, ascorbic acid, ethylenediaminetetraacetic acid (EDTA), poly(ethylenimine), vitamin E and mixtures thereof.

In certain embodiments, the preservative is methionine. In certain embodiments, the preservative is butylhydroxytoluene. In certain embodiments, the preservative is butylhydroxyanisol. In certain embodiments, the preservative is tocopherol. In certain embodiments, the preservative is propylgallate. In certain embodiments, the preservative is ethylenediaminetetraacetic acid. In certain embodiments, the preservative is poly(ethylenimine). In certain embodiments, the preservative is vitamin E.

As defined herein, the term "methionine" is intended to encompass both D-methionine and L-methionine, and mixtures thereof. In certain embodiments, the term "methionine" refers to L-methionine. In certain embodiments, the term "methionine" refers to D-methionine. In certain embodiments, the term "methionine" refers to a mixture of D-methionine or L-methionine. In certain embodiments, the term "methionine" refers to L-methionine hydrochloride salt.

As defined herein, the term "EDTA" is intended to encompass all EDTA forms that are known in the art such as EDTA salts, including EDTA metal salts, such as EDTA disodium salt, EDTA dipotassium salt, EDTA calcium salt, EDTA dimagnesium salt or mixtures thereof. In certain embodiments, EDTA refers to EDTA disodium salt. In certain embodiments, the term "EDTA" refers to EDTA dicalcium salt. In certain embodiments, the term "EDTA" refers to EDTA anhydrous.

In certain embodiments, the molar ratio of antioxidant to CNP moiety is from about 0.1:1 to about 100:1. In certain embodiments, the molar ratio of antioxidant to CNP moiety is from about 0.1:1 to about 70:1. In certain embodiments, the molar ratio of antioxidant to CNP moiety is from about 0.1:1 to about 15:1. In certain embodiments, the molar ratio of antioxidant to CNP moiety is from about 1:1 to about 10:1. In certain embodiments, the molar ratio of antioxidant to CNP moiety is from about 3:1 to about 7:1.

In certain embodiments, the reconstituted solution does not comprise an antimicrobial.

In certain embodiments, the reconstituted solution comprises an antimicrobial.

In certain embodiments, the reconstituted solution comprises one or more excipient.

In certain embodiments, the reconstitution solution is sterile water.

In certain embodiments, the reconstitution solution is sterile water comprising 0.7-1.1% benzylalcohol.

In certain embodiments, the reconstitution solution is sterile water comprising 0.9% benzylalcohol.

In certain embodiments, the reconstituted solution comprises a pH-modifying agent.

As used herein, the term "pH-modifying agent" refers to a chemical compound that is used to modify the pH of the reconstitution solution.

In certain embodiments, the pH-modifying agent may be an acid or acidic salt thereof. The acid may be selected from the group consisting of acetic acid, citric acid, succinic acid, hydrochloric acid, phosphoric acid, carbonic acid, nitric acid and mixtures thereof.

In certain embodiments, the pH-modifying agent may be a base or basic salt thereof. The base may be selected from the group consisting of Tris (tris(hydroxymethyl)aminomethane), sodium hydroxide, potassium hydroxide, lysine and mixtures thereof.

After reconstitution, a single dose formulation comprising the CNP conjugate has a volume of not more than 4 ml, such as from about 0.03 to about 1.1 ml. In certain embodiments, the volume is about 0.03 ml. In certain embodiments, the volume is about 0.05 ml. In certain embodiments, the volume is about 0.1 ml. In certain embodiments, the volume is about 0.3 ml. In certain embodiments, the volume is about 0.8 ml. In certain embodiments, the volume is about 1 ml. In certain embodiments, the volume is about 2 ml. In certain embodiments, the volume is about 3 ml. In certain embodiments, the volume is about 4 ml.

In certain embodiments, the CNP conjugate is sufficiently dosed in the formulation to provide therapeutically effective amount of CNP for at least three days in one application, such as for at least four days, such as for at least five days, such as for at least six days.

In certain embodiments, the CNP conjugate is sufficiently dosed in the formulation to provide a therapeutically effective amount of CNP for one week.

The buffering agent maintains the pH of the reconstituted formulation within a desired range.

In certain embodiments, the pH of the reconstituted formulation is not higher than 6, as under basic conditions the reversible linkage within the CNP-conjugate may not be stable.

In certain embodiments, the pH of the reconstituted formulation is from about pH 4 to about pH 6. In certain embodiments, the pH of the reconstituted formulation is from about pH 4.5 to about pH 5.5. In certain embodiments, the pH of the reconstituted formulation is about 5. In certain embodiments, the pH of the reconstituted formulation is 5.

In certain embodiments, the buffering agent has a concentration ranging from 1.3 to 57.6 mM in the reconstituted formulation. In certain embodiments, the buffering agent has a concentration ranging from 1.7 to 33 mM in the reconstituted formulation. In certain embodiments, the buffering agent has a concentration ranging from 5.1 to 20.3 mM in the reconstituted formulation. In certain embodiments, the buffering agent has a concentration of about 10 mM in the reconstituted formulation.

In certain embodiments, the reconstituted formulation comprises

| | |
|---|---|
| CNP conjugate | 0.9-82.1 mg/ml |
| succinic acid | 1.3-57.6 mM |
| trehalose dihydrate | 67-111.6 mg/ml, | and has a pH ranging from pH 4.0 to pH 6.0.

Reconstituted formulations may also be available in different strengths, i.e. concentrations, of CNP conjugate such as high, medium and low. Thus, it is another aspect of the present invention that the reconstituted formulation of the present invention is provided in different concentrations of CNP conjugate, such as in two different concentrations, such as in three different concentrations, such as in four different concentrations, such as in five different concentrations, such as in six different concentrations, such as in seven different concentrations, such as in eight different concentrations, such as in nine different concentrations, such as in ten different concentrations, such as in eleven different concentrations, such as in twelve different concentrations.

It is recognized by one of ordinary skill in the art that there may be rounding errors in the concentrations of the elements comprised in the reconstituted formulations of the present invention, meaning that when starting from a particular dry formulation the composition of the corresponding reconstituted formulation may vary to a certain degree due to necessary rounding.

In certain embodiments, the reconstituted formulation comprises:

| | |
|---|---|
| CNP conjugate | 19.8-73.6 mg/ml |
| succinic acid | 1.7-50 mM |
| trehalose dihydrate | 63-100 mg/ml | and has a pH ranging from pH 4.0 to pH 6.0.

In certain embodiments, the reconstituted formulation comprises:

| | |
|---|---|
| CNP conjugate | 4.2-16.5 mg/ml |
| succinic acid | 1.7-36.4 mM |
| trehalose dihydrate | 67-105 mg/ml | and has a pH ranging from pH 4.0 to pH 6.0.

In certain embodiments, the reconstituted formulation comprises:

| | |
|---|---|
| CNP conjugate | 1.0-4.4 mg/ml |
| succinic acid | 1.7-33 mM |
| trehalose dihydrate | 67-105 mg/ml | and has a pH ranging from pH 4.0 to pH 6.0.

In certain embodiments, the reconstituted formulation comprises:

| | |
|---|---|
| CNP conjugate | 27.5-50.5 mg/ml |
| succinic acid | 5.1-20.3 mM |
| trehalose dihydrate | 67-95 mg/ml | and has a pH ranging from pH 4.0 to pH 6.0.

In certain embodiments, the reconstituted formulation comprises:

| | |
|---|---|
| CNP conjugate | 5.8-10.8 mg/ml |
| succinic acid | 5.1-20.3 mM |
| trehalose dihydrate | 72-105 mg/ml | and has a pH ranging from pH 4.0 to pH 6.0.

In certain embodiments, the reconstituted formulation comprises:

| | |
|---|---|
| CNP conjugate | 1.5-2.9 mg/ml |
| succinic acid | 5.1-20.3 mM |
| trehalose dihydrate | 73-105 mg/ml | and has a pH ranging from pH 4.0 to pH 6.0.

In certain embodiments, the reconstituted formulation comprises:

| | |
|---|---|
| CNP conjugate | 37.4-42.9 mg/ml |
| succinic acid | 9.3-10.2 mM |
| trehalose dihydrate | 71-87 mg/ml | and has a pH ranging from pH 4.5 to pH 5.5.

In certain embodiments, the reconstituted formulation comprises:

| | |
|---|---|
| CNP conjugate | 7.5-9.1 mg/ml |
| succinic acid | 9.3-11 mM |
| trehalose dihydrate | 75-97 mg/ml | and has a pH ranging from pH 4.5 to pH 5.5.

In certain embodiments, the reconstituted formulation comprises:

| | |
|---|---|
| CNP conjugate | 1.9-2.4 mg/ml |
| succinic acid | 9.3-11 mM |
| trehalose dihydrate | 77-97 mg/ml | and has a pH ranging from pH 4.5 to pH 5.5.

In certain embodiments, the reconstituted formulation comprises about 60.4 mg/ml CNP conjugate, about 10 mM succinic acid, about 70 mg/ml trehalose dihydrate and has a pH of 5.

In certain embodiments, the reconstituted formulation comprises 60.4 mg/ml CNP conjugate, 10 mM succinic acid, 70 mg/ml trehalose dihydrate and has a pH of 5.

In certain embodiments, the reconstituted formulation comprises about 60.4 mg/ml CNP conjugate, about 10 mM succinic acid, about 56 mg/ml trehalose dihydrate and has a pH of 5.

In certain embodiments, the reconstituted formulation comprises 60.4 mg/ml CNP conjugate, 10 mM succinic acid, 56 mg/ml trehalose dihydrate and has a pH of 5.

In certain embodiments, the reconstituted formulation comprises about 39.6 mg/ml CNP conjugate, about 10 mM succinic acid, about 79.0 mg/ml trehalose dihydrate and has a pH of 5.

In certain embodiments, the reconstituted formulation comprises 40 mg/ml CNP conjugate, 10 mM succinic acid, 79 mg/ml trehalose dihydrate and has a pH of 5.

In certain embodiments, the reconstituted formulation comprises 39.6 mg/ml CNP conjugate, 10 mM succinic acid, 79.0 mg/ml trehalose dihydrate and has a pH of 5.

In certain embodiments, the reconstituted formulation comprises about 8.2 mg/ml CNP conjugate, about 10 mM succinic acid, about 89.0 mg/ml trehalose dihydrate and has a pH of 5.

In certain embodiments, the reconstituted formulation comprises 8 mg/ml CNP conjugate, about 10 mM succinic acid, 89 mg/ml trehalose dihydrate and has a pH of 5.

In certain embodiments, the reconstituted formulation comprises 8.2 mg/ml CNP conjugate, 10 mM succinic acid, 89.0 mg/ml trehalose dihydrate and has a pH of 5.

In certain embodiments, the reconstituted formulation comprises about 2.2 mg/ml CNP conjugate, about 10 mM succinic acid, about 89.5 mg/ml trehalose dihydrate and has a pH of 5.

In certain embodiments, the reconstituted formulation comprises 2 mg/ml CNP conjugate, 10 mM succinic acid, 90 mg/ml trehalose dihydrate and has a pH of 5.

In certain embodiments, the reconstituted formulation comprises 2.2 mg/ml CNP conjugate, 10 mM succinic acid, 89.5 mg/ml trehalose dihydrate and has a pH of 5.

The reconstituted formulation may be administered by injection, infusion, intradermal, subcutaneous, intramuscular, intravenous, intraosseous, and intraperitoneal.

In certain embodiments, the reconstituted formulation comprising CNP conjugate is administered by subcutaneous injection.

In certain embodiments, the reconstituted formulation comprising CNP conjugate is administered by subcutaneous injection with a syringe, needle, pen injector or auto-injector.

In certain embodiments, the reconstituted formulation comprising CNP conjugate is administered by subcutaneous injection with a syringe.

In certain embodiments, the reconstituted formulation comprising CNP conjugate is administered by subcutaneous injection with a pen injector.

In certain embodiments, the reconstituted formulation comprising CNP conjugate is administered by subcutaneous injection with an auto-injector.

Another aspect of the present invention is the dry or reconstituted pharmaceutical formulation of the present invention for use as a medicament.

In another aspect, the present invention relates to the dry or reconstituted pharmaceutical formulation of the present invention for use in the treatment, control, delay or prevention of one or more diseases which can be treated, controlled, delayed or prevented with CNP.

In certain embodiments, the present invention relates to the dry or reconstituted pharmaceutical formulation of the present invention for use in the treatment of one or more diseases which can be treated with CNP.

A further aspect of the present invention is a method of treating, controlling, delaying or preventing in a patient one or more diseases which can be treated by CNP, the method comprising administering to the patient a therapeutically effective amount of the reconstituted pharmaceutical formulation of the present invention.

In certain embodiments, the patient is an adult. In certain embodiments, the patient is a pediatric patient.

In certain embodiments, said one or more diseases which can be treated, controlled, delayed or prevented with CNP are selected from the group consisting of bone-related disorders such as skeletal dysplasias; cancer; autoimmune diseases; fibrotic diseases; inflammatory diseases; central nervous system diseases such as neurodegenerative diseases; infectious diseases; lung diseases; heart and vascular diseases; metabolic diseases and ophthalmic diseases.

In certain embodiments, said one or more diseases which can be treated, controlled, delayed or prevented with CNP are selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, cranio synostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis, osteopoikilosis, hemorrhagic shock, hypertension, restenosis, arteriosclerosis, acute decompensated heart failure, congestive heart failure, cardiac edema, nephredema, hepatic edema, acute renal insufficiency, chronic renal insufficiency, glaucoma, elevated intraocular pressure, multiple myeloma, myeloproliferative syndrome, leukemia, plasma cell leukemia, lymphoma, glioblastoma, prostate cancer, bladder cancer, mammary cancer, growth retardation, skull deformities, orthodontic defects, cervical cord compression, spinal stenosis, hydrocephalus, hearing loss due to chronic otitis, cardiovascular disease, neurological disease and obesity.

In certain embodiments, said one or more diseases which can be treated, controlled, delayed or prevented with CNP are selected from the group consisting of achondroplasia such as homozygous achondroplasia, hypochondroplasia, short stature, dwarfism, osteochondrodysplasias, thanatophoric dysplasia, osteogenesis imperfecta, achondrogenesis, chondrodysplasia punctata, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, neurofibromatosis, Legius syndrome, LEOPARD syndrome, Noonan syndrome, hereditary gingival fibromatosis, neurofibromatosis type 1, Legius syndrome, cardiofaciocutaneous syndrome, Costello syndrome, SHOX deficiency, idiopathic short stature, growth hormone deficiency, osteoarthritis, cleidocranial dysostosis, cranio synostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, dyssegmental dysplasia, enchondromatosis, fibrous dysplasia, hereditary multiple exostoses, hypophosphatemic rickets, Jaffe-Lichtenstein syndrome, Marfan syndrome, McCune-Albright syndrome, osteopetrosis, osteopoikilosis, hemorrhagic shock, hypertension, restenosis, arteriosclerosis, acute decompensated heart failure, congestive heart failure, cardiac edema, nephredema, hepatic edema, acute renal insufficiency, chronic renal insufficiency, glaucoma, elevated intraocular pressure, multiple myeloma, myeloproliferative syndrome, leukemia, plasma cell leukemia, lymphoma, glioblastoma, prostate cancer, bladder cancer, mammary cancer, growth retardation, skull deformities, orthodontic defects, cervical cord compression, spinal stenosis, hydrocephalus, hearing loss due to chronic otitis, obesity, disorders involving abnormal RAS-mitogen-activated protein kinase signaling, pulmonary hypertension, vasculopathy, endothelial dysfunction, liver cirrhosis, liver ascites, liver fibrosis, hepatorenal syndrome, asthma, pulmonary fibrosis, chronic kidney diseases, cardiorenal syndrome, dyspnea and lysosomal storage diseases such as mucopolysaccharidosis.

In certain embodiments, said one or more diseases which can be treated, controlled, delayed or prevented with CNP is one or more cardiovascular diseases selected from the group consisting of arrhythmia such as cardiac or sinus arrhythmia; atrial fibrillation; atrial flutter; bradycardia; Brugada syndrome; premature cardiac complexes; commotio cordis; heart block; long QT syndrome; parasystole; pre-excitation syndrome; tachycardia; ventricular fibrillation; ventricular flutter; cardiac conduction system disease; low cardiac output; cardiomegaly; dilated cardiomyopathy; hypertrophy such as left ventricular hypertrophy or right ventricular hyperthrophy; cardiomyopathy such as alcoholic, dilated, hypertrophic, restrictive, diabetic or Chagas cardiomyopathy; arrhythmogenic right ventricular dysplasia; endocardial fibroelastosis; endomyocardial fibrosis; glycogen storage disease type Iib; Kearns-Sayre syndrome; myocardial reperfusion injury; myocarditis; sarcoglycanophaties; endocarditis such as bacterial or non-infective endocarditis; heart arrest; sudden cardiac death; out-of-hospital cardiat arrest; cardio-renal syndrome; paroxysmal dyspnea; cardiac edema, heart failure such as diastolic or systolic heart failure; heart valve disease; aortic valve insufficiency; aortic valve stenosis; heart valve prolapse; mitral valve insufficiency; mitral valve stenosis; pulmonary atresia; pulmonary valve insufficiency; pulmonary valve stenosis; tricuspid atresia; tricuspid valve insufficiency; tricuspid valve stenosis; myocardial ischemia; acute coronary syndrome; angina pectoris; coronary disease; Kounis syndrome; myocardial infarction; pulmonary heart disease; ventricular dysfunction such as left or right ventricular dysfunction; ventricular outflow obstruction; aortic valve stenosis, pulmonary valve stenosis; hypertension; atherosclerosis; restenosis; critical limb ischaemia; peripheral arterial disease; ischemia such as ischemia-reperfusion injury or ischemic injuries; abnormal fluid accumulation in the heart and myocardial edema.

In certain embodiments, said one or more diseases which can be treated, controlled, delayed or prevented with CNP is selected from the group consisting of ischemic heart disease such as myocardial infarction; congestive heart failure; arrhythmia and atherosclerosis.

In certain embodiments, said one or more diseases which can be treated, controlled, delayed or prevented with CNP is one or more central nervous system diseases selected from the group consisting of brain ischemia such as ischemic hypoxia; brain infarction; transient ischemic attack; vertebrobasilar insufficiency; cerebrovascular disorders; stroke; intracranial hemorrhages; corneal neovascularization; corneal transplantation; graft-versus-host disease; graft rejection; glaucoma such as angle-closure, neovascular, openangle or low tension glaucoma; ischemic optic neuropathy; central serous chorioretinopathy; retinopathy such as diabetic or hypertensive retinopathy; retinal degeneration; macular degeneration; geographic atrophy; macular edema; Stargardt disease; vitelliform macular dystrophy; wet macular degeneration; retinoschisis; retinal detachment; retinal perforations; retinal haemorrhage; retinal neovascularization; retinal vein occlusion; retinal artery occlusion; retinopathy of prematurity and proliferative vitreoretinopathy.

In certain embodiments, said one or more diseases are selected from the group consisting of hypophosphatasia, hypochondroplasia, Muenke syndrome, hypertension, osteogenesis imperfecta and achondroplasia.

In certain embodiments, said one or more diseases which can be treated with CNP invention is hypophosphatasia. In certain embodiments, said one or more diseases which can be treated with CNP is hypochondroplasia. In certain embodiments, said one or more diseases which can be treated with CNP is Muenke syndrome. In certain embodiments, said one or more diseases which can be treated with CNP is hypertension. In certain embodiments, said one or more diseases which can be treated with CNP is osteogenesis imperfecta. In certain embodiments, said one or more diseases which can be treated with CNP is achondroplasia.

EXAMPLES

Materials and Methods

All materials were commercially available except where stated otherwise.

RP-HPLC was used to determine the content and purity of compound (1) and to detect free CNP-38: Mobile phase A was composed of 0.05% aqueous TFA and mobile phase B was composed of 0.04% TFA in acetonitrile. A Waters Acquity CSH C18, 130 Å, 1.7 µm, 2.1×100 mm column was used. Flow rate was set to 0.3 mL/min, detection was at a wavelength of 215 nm, the column running temperature was 60° C. (±1° C.). Samples were diluted with formulation buffer containing 0.5% Tween®-20. The content was determined by peak area comparison to a reference solution.

SE-HPLC was used to determine the purity of compound (1): Mobile phase was composed of 15 mM sodium phosphate pH 7.40, 135 mM sodium chloride, 0.2% Pluronic F-68 in water. A GE Superdex 200 Increase 10/300 GL column was used. Flow rate was set to 0.75 mL/min, detection was at a wavelength of 215 nm, the column running temperature was room temperature. Samples were diluted with formulation buffer containing 0.05% Pluronic F-68.

Peptide mapping of compound (1) was used to assess the conversion of aspartate (28) into isoaspartate (28) and the oxidation of methionine (33) into methioninoxide (33) (Met (O). Thermolysin digestion of (1) was performed at pH 7.5 for 7 h at 37° C. at a thermolysin/CNP-38 ratio=1:20 (w/w). The resulting peptide mixture was separated by RP-HPLC on Waters Acquity UPLC HSS T3, 100 Å, 1.8 µm, 2.1×150 mm column with 0.10 vol % aq. TFA as mobile phase A and 0.09% TFA in acetonitrile as mobile phase B and detection at 210 nm. Flow rate was set to 0.28 mL/min, the column running temperature was 45° C. (±1° C.). The thermolysin fragments which contain aspartate (28) and methionine (33) were characterized via LC-MS. In routine analysis, fragments are compared to a reference mixture containing these fragment peptides. The fragments were quantified based on their respective peak area relative to the peak area of the corresponding unmodified fragments. Under the conditions of the thermolysin digest and subsequent RP-HPLC, formation of the isoaspartate product of aspartate (28) and oxidation of the methionine (33) could be quantified for (1).

Biopotency analysis was carried out by in vitro release of CNP-38 from (1) and subsequent biopotency analysis of released CNP-38 in a cell assay.

In vitro release of CNP-38 from (1) and RP-HPLC quantification: (1) was incubated at pH 10.0 and 15° C. for 24 h. pH was adjusted by dilution of reconstituted formulation with a release buffer (0.5 M boric acid, 10 mM methionine, 2.383 g/L Pluronic-F68; pH adjusted to 10.0 using 4M aqueous NaOH solution) in a 1:3.5 (v/v) dilution (e.g. 50 μL of a 3.6 mg CNP-38 eq./mL solution of (1) were diluted with 175 μL release buffer). After incubation, the release was quenched by dilution 1:1 (v/v) with 5% (v/v) acetic acid. The amount of released CNP-38 was determined by peak area comparison to a CNP-38 reference solution with known content.

Determination of biopotency of released CNP-38 by functional cGMP stimulation in HEK293 cells: ANPR-B overexpressing Hek293 cell line was developed as follows: The coding region of the NPR-B reference sequence was cloned into a lentiviral vector under a CMV promoter for constitutive receptor expression. A bicistronic element located on the vector for puromycin resistance was used as eukaryotic selection marker. After transduction, stably growing cell pools were subjected to qRT-PCR for confirmation of receptor mRNA-expression compared to parental Hek293 cells. Stimulation of the NPR-B receptor with CNP-38 leads to intracellular production of the second messenger cGMP which is detected with a commercially available cGMP assay.

Cells were routinely cultured in DMEM/Glutamax/HEPES medium with 10% FBS and 1% puromycin solution (370 μg/mL) at 37° C. and 5% $CO_2$. For each assay, cells were suspended in DMEM+2% BSA and incubated 3 hours at 37° C. and 5% $CO_2$. A dilution series of released CNP mixture in stimulation buffer (DMEM+2% BSA+0.1 mM IBMX+0.1% Tween®-20) was prepared and added to the cells (additional 1:2 dilution of CNP-38 serial dilution). After incubation for 60 min at 37° C. and 5% $CO_2$, the cells were lyzed and cGMP levels were determined with a commercially available cGMP TR-FRET assay (Cisbio, cGMP kit, Cat. No. 62GM2PEB). Potency was determined using four parameter logistic curve fitting in a validated PLA software by parallel line analysis compared to a CNP-38 reference standard.

RP-HPLC was used to determine the amount of degraded CNP-38 (deamidated and aspartimide variants). Mobile phase A was composed of 0.05% aqueous TFA and mobile phase B was composed of 0.04% TFA in acetonitrile. A Waters Acquity HSS T3 C18, 100 Å, 1.8 μm, 2.1×100 mm column was used. Flow rate was set to 0.5 mL/min, detection was at a wavelength of 215 nm, the column running temperature was set to 30° C. The deamidated and aspartimide variants were quantified relative to the peak area of unmodified CNP-38.

Example 1: Synthesis of Compound (1)

Compound (1) was synthesized as described in WO2017/118693 for conjugate 11i.

Example 2: Stability Testing of Lyophilized Formulations Containing Compound (1)

Eight different formulations (F1-F8) containing compound (1) were prepared as shown by Table 1 and 200 μL of each formulation was filled into vials and lyophilized. The water contents of the lyophilizates were below 0.4% in all formulations, as determined by Karl-Fischer titration. Each formulation contained appropriate amounts of compound (1) to yield a concentration of 3.6 mg CNP-38/ml after reconstitution with 200 μL water. Formulations were placed in an incubator set to maintain 25° C. or 40° C. After 3 months (T3M), the formulations were reconstituted with water and subjected to analysis. Results show a favorable purity profile of compound (1) for the trehalose containing formulations compared to the mannitol containing formulations. Also, it was observed that no additives are required in order to prevent methionine oxidation.

TABLE 1

| | Content of (1) (mg CNP-38/mL) | Buffer | pH-adjusting buffer | pH | Trehalose dihydrate (mg/mL) | Mannitol (mg/mL) | Annealing |
|---|---|---|---|---|---|---|---|
| F1 | 3.6 | Succinic acid (10 mM) | Tris | 4.5 | 94 | — | No |
| F2 | 3.6 | Succinic acid (10 mM) | Tris | 5.0 | 94 | — | No |
| F3 | 3.6 | Succinic acid (10 mM) | Tris | 5.5 | 94 | — | No |
| F4 | 3.6 | Succinic acid (10 mM) | Tris | 6.0 | 94 | — | No |
| F5 | 3.6 | Histidine (10 mM) | Tris | 5.0 | 94 | — | No |
| F6 | 3.6 | Histidine (10 mM) | Tris | 6.0 | 94 | — | No |
| F7 | 3.6 | Succinic acid (10 mM) | Tris | 5.0 | — | 46 | Yes |
| F8 | 3.6 | Succinic acid (10 mM) | Tris | 6.0 | — | 46 | Yes |

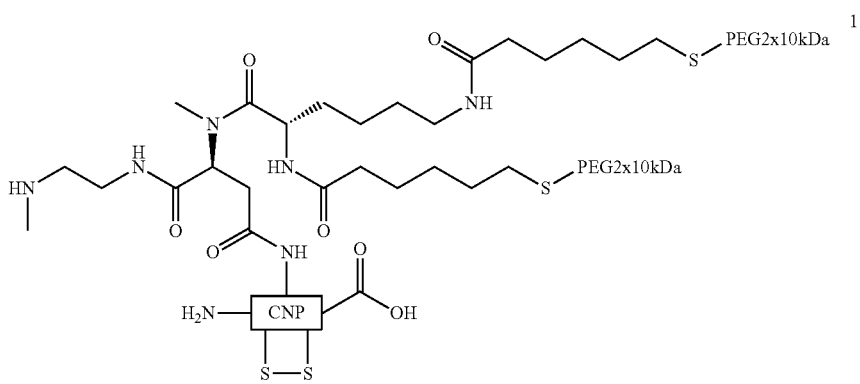

TABLE 2

| | Sample storage conditions | Purity by RP-HPLC (%) | Free CNP (%) | Purity by SE-HPLC (%) | Peptide mapping, Met[O] content (%) | Peptide mapping, Isoasp content (%) |
|---|---|---|---|---|---|---|
| F1 | T0 | 98.9 | <LOQ[a] | 95.1 | 0.9 | 2.0 |
| | T3M, 25° C. | 98.8 | <LOQ[a] | 95.4 | 1.1 | 2.0 |
| | T3M, 40° C. | 97.4 | 0.2 | 94.0 | 1.2 | 2.6 |
| F2 | T0 | 98.8 | <LOQ[a] | 94.9 | 1.0 | 2.2 |
| | T3M, 25° C. | 98.6 | <LOQ[a] | 95.4 | 1.1 | 2.0 |
| | T3M, 40° C. | 97.6 | 0.1 | 93.9 | 1.4 | 2.4 |
| F3 | T0 | 98.8 | <LOQ[a] | 95.2 | 0.8 | 2.3 |
| | T3M, 25° C. | 98.6 | <LOQ[a] | 95.7 | 0.9 | 2.0 |
| | T3M, 40° C. | 97.6 | 0.2 | 94.1 | 1.3 | 1.8 |
| F4 | T0 | 98.8 | <LOQ[a] | 95.1 | 0.9 | 2.2 |
| | T3M, 25° C. | 98.6 | <LOQ[a] | 95.1 | 1.0 | 2.1 |
| | T3M, 40° C. | 98.1 | 0.1 | 94.2 | 1.3 | 1.8 |
| F5 | T0 | 98.7 | <LOQ[a] | 95.2 | 0.8 | 2.2 |
| | T3M, 25° C. | 98.6 | <LOQ[a] | 95.5 | 1.1 | 1.6 |
| | T3M, 40° C. | 98.3 | 0.1 | 94.1 | 1.1 | 1.7 |
| F6 | T0 | 98.6 | <LOQ[a] | 95.1 | 0.9 | 2.2 |
| | T3M, 25° C. | 98.9 | <LOQ[a] | 94.8 | 1.1 | 2.1 |
| | T3M, 40° C. | 98.2 | 0.2 | 93.0 | 1.4 | 2.1 |
| F7 | T0 | 98.7 | <LOQ[a] | 95.1 | 0.8 | 1.9 |
| | T3M, 25° C. | 97.3 | 0.2 | 94.1 | 1.0 | 2.3 |
| | T3M, 40° C. | 89.7 | 3.2 | 91.2 | 1.5 | 6.7 |
| F8 | T0 | 98.4 | <LOQ[a] | 94.9 | 0.8 | 2.2 |
| | T3M, 25° C. | 96.4 | 0.5 | 93.7 | 1.0 | 1.8 |
| | T3M, 40° C. | 80.4 | 6.1 | 85.2 | 1.5 | 2.0 |

[a]LOQ = 0.1%

Example 3: Stability Testing of Liquid and Lyophilized Formulations Containing Compound (1)

A formulation (F9) of (1) was prepared and 200 μL of the formulation was filled into a vial and lyophilized. The lyophilized formulation contained appropriate amounts of to yield a concentration of 3.0 mg CNP-38/ml after reconstitution with 200 μL water. The lyophilizate and the liquid formulation that was used for the preparation of the lyophilizate were placed in an incubator set to maintain 40° C.

After 21 days (T21D), the lyophilizate was reconstituted with water and the formulations were subjected to analysis. Results show that lyophilization protects (1) from degradation like methionine oxidation and isoaspartate formation.

TABLE 3

| | Content of (1) (mg CNP-38/mL) | Buffer | Base | pH | Trehalose dihydrate (mg/mL) |
|---|---|---|---|---|---|
| F9 | 3.0 | Succinic acid (10 mM) | Tris | 5.0 | 94 |

TABLE 4

| Sample storage conditions | Peptide mapping, Met[O] content (%) | Peptide mapping, IsoAsp content (%) |
|---|---|---|
| F9 T0 | <LOQ[a] | <LOQ[a] |
| T21D, 40° C., lyo | <LOQ[a] | <LOQ[a] |
| T21D, 40° C., liquid | 10.5 | 6.9 |

[a]LOQ = 1.2%

Example 4: Stability Testing of Formulations Containing (1) and a Surfactant Three different formulations (F10-F12) of (1) were prepared and 1080 μL was filled into vials and lyophilized. Each formulation contained appropriate amounts of (1) to yield a concentration of 3.5 mg CNP-38/ml after reconstitution with 1000 μL water. Some formulations contained Polysorbate 20 (PS 20) or Polysorbate 80 (PS 80) as a surfactant. Lyophilized formulations were placed in an incubator set to maintain 40° C./75% RH. After 1 month (T1M) and 3 months (T3M), formulations were reconstituted with 1 mL water and subjected to analysis.

The surfactant containing formulations F11 and F12 show a slight increase in methionine oxidation of (1) at stressed conditions and a marked effect on reconstitution time (without shaking) after addition of 1 mL water compared to F10.

TABLE 5

| | Content of (1) (mg CNP-38/mL) | Buffer | pH-adjusting buffer | pH | Trehalose dihydrate (mg/mL) | PS 20 (%) | PS 80 (%) |
|---|---|---|---|---|---|---|---|
| F10 | 3.5 | Succinic acid (10 mM) | Tris | 5.0 | 84 | — | — |
| F11 | 3.5 | Succinic acid (10 mM) | Tris | 5.0 | 84 | 0.2 | — |
| F12 | 3.5 | Succinic acid (10 mM) | Tris | 5.0 | 84 | — | 0.2 |

TABLE 6

| | Sample storage conditions | Purity by RP-HPLC (%) | Free CNP (%) | Purity by SE-HPLC (%) | Peptide mapping, Met[O] content (%) | Peptide mapping, Isoasp content (%) | Relative reconstitution time[c] (%) |
|---|---|---|---|---|---|---|---|
| F10 | T0 | 99.4 | <LOQ[a] | 98.9 | <LOQ[b] | <LOQ[b] | 100 |
| | T1M, 40° C. | 99.2 | <LOQ[a] | 96.4 | <LOQ[b] | <LOQ[b] | 95 |
| | T3M, 40° C. | 99.2 | 0.14 | 95.3 | <LOQ[b] | <LOQ[b] | 80 |
| F11 | T0 | 99.5 | <LOQ[a] | 99.1 | <LOQ[b] | <LOQ[b] | 190 |
| | T1M, 40° C. | 99.2 | <LOQ[a] | 96.4 | <LOQ[b] | <LOQ[b] | 149 |
| | T3M, 40° C. | 98.3 | 0.22 | 95.3 | 0.82 | <LOQ[b] | 186 |
| F12 | T0 | 99.4 | <LOQ[a] | 99.5 | <LOQ[b] | <LOQ[b] | 161 |

TABLE 6-continued

| Sample storage conditions | Purity by RP-HPLC (%) | Free CNP (%) | Purity by SE-HPLC (%) | Peptide mapping, Met[O] content (%) | Peptide mapping, Isoasp content (%) | Relative reconstitution time[c] (%) |
|---|---|---|---|---|---|---|
| T1M, 40° C. | 98.4 | <LOQ[a] | 96.5 | <LOQ[b] | <LOQ[b] | 157 |
| T3M, 40° C. | 96.6 | 0.19 | 95.8 | 1.02 | <LOQ[b] | 191 |

[a]LOQ = 0.1%
[b]LOQ = 0.8-1.1%
[c]without shaking

Example 5: Long Term Stability Testing of a Lyophilized Formulations Containing Compound (1)

A lyophilized formulation (F13) of compound (1) was prepared, by lyophilizing of 1080 μL in a vial. The formulation contained appropriate-amounts of (1) to yield a nominal concentration of 3.9 mg CNP-38/vial and 3.6 mg CNP-38/ml after reconstitution with 1000 μL of water. Formulations were placed in an incubator set to maintain respectively 5° C. 25° C./60% RH, 30° C./65% RH and 40° C./75% RH. After 3 months (T3M), 4 months (T4M), 6 months (T6M), 9 months (T9M), 12 months (T12M), 18 months (T18M) and 24 months (T24M) formulations were reconstituted with 1000 μL of water and subjected to analysis.

Results show a high stability of compound (1) in the lyophilized formulation F13, as shown here for content, purity and biopotency. Moreover, the formulation showed a good stability when tested with relevant pharmacopeia methods. The lyophilized formulation was characterized by a white cake and no change in cake appearance was detected irrespective of storage. The residual moisture content was very low after lyophilization (0.03%) and only slightly increased during the study. There was no significant change of reconstitution time during storage. Visual inspection revealed that the samples were practically free of visible particles throughout the study for all samples and a low amount of subvisible particles, i.e. ≥25 μm and 71≥10 μm were observed irrespective of storage temperature and storage time (determined with flow-through microscopy). A slight change in color from B9 to >B8 was observed during 12 months storage at 5° C., whereas no increase in color was observed during 6 months storage at 25° C. and 30° C. or 3 months at 40° C. (color was assessed with a spectral colorimeter and the absolute values of the color determination were conducted in accordance to the European Pharmacopoeia, 8th Edition, monograph 2.2.2). The turbidity (measured with a turbidimeter) of the lyophilized samples stored for up to twelve months at 2-8° C., 25° C./60% r.h. and 30° C./65% r.h., was unchanged. Only a minimal increase of the turbidity was measured for the sample stored for three months at 40° C./75% r.h. No changes in appearance were observed during storage for up to 12 months at 5° C., with values <1 NTU (Nephelometric turbidity unit). During 6 months at 25° C., 30° C. and 40° C. values <1 NTU were also obtained. pH was unaffected by storage. Finally, the osmolality at T0 was within the physiological range and no change was detected during the study.

TABLE 7

| | Content of (1) (nominal, mg CNP-38 eq./mL) | Buffer | pH-adjusting buffer | pH | Trehalose dihydrate (mg/mL) |
|---|---|---|---|---|---|
| F13 | 3.6 | Succinic acid (10 mM) | Tris | 5.0 | 84 |

TABLE 8

| Sample storage conditions | Content of (1) (CNP-38 eq, mg/mL) | Purity by RP-HPLC (%) | Free CNP (%) | Purity by SE-HPLC (%) | Peptide mapping, Met[O] content (%) | Peptide mapping, IsoAsp content (%) | Biopotency (%) |
|---|---|---|---|---|---|---|---|
| T0 | 3.5 | 97.6 | <LOQ[a] | 98.3 | <LOQ[b] | <LOQ[b] | 93 |
| T3M, 5° C. | | | | 98.4 | <LOQ[b] | <LOQ[b] | 107 |
| T4M, 5° C. | 3.5 | 97.3 | <LOQ[a] | | | | |
| T6M, 5° C. | 3.5 | 97.4 | <LOQ[a] | 98.3 | <LOQ[b] | <LOQ[b] | 95 |
| T9M, 5° C. | 3.5 | 97.3 | <LOQ[a] | 98.2 | <LOQ[b] | <LOQ[b] | |
| T12M, 5° C. | 3.5 | 97.1 | <LOQ[a] | 98.2 | <LOQ[b] | <LOQ[b] | 90, 100[c] |
| T18M, 5° C. | 3.5 | 97.1 | <LOQ[a] | 98.3 | <LOQ[b] | <LOQb | 109, 104[c] |
| T24M, 5° C. | 3.5 | 97.1 | <LOQ[a] | 98.3 | <LOQ[b] | <LOQ[b] | 100, 110[c] |
| T0 | 3.5 | 97.6 | <LOQ[a] | 98.3 | <LOQ[b] | <LOQ[b] | |
| T3M, 25° C. | | | | 97.8 | <LOQ[b] | <LOQ[b] | 91 |
| T4M, 25° C. | 3.5 | 97.2 | <LOQ[a] | | | | |
| T6M 25° C. | 3.5 | 97.1 | <LOQ[a] | 97.4 | <LOQ[b] | <LOQ[b] | 106 |
| T0 | 3.5 | 97.6 | <LOQ[a] | 98.3 | <LOQ[b] | <LOQ[b] | |
| T3M, 30° C. | | | | 97.3 | <LOQ[b] | <LOQ[b] | 96 |
| T4M, 30° C. | 3.4 | 97.1 | <LOQ[a] | | | | |
| T6M, 30° C. | 3.5 | 97.0 | <LOQ[a] | 96.9 | <LOQ[b] | <LOQ[b] | 89 |
| T0 | 3.5 | 97.6 | <LOQ[a] | 98.3 | <LOQ[b] | <LOQ[b] | |

TABLE 8-continued

| Sample storage conditions | Content of (1) (CNP-38 eq, mg/mL) | Purity by RP-HPLC (%) | Free CNP (%) | Purity by SE-HPLC (%) | Peptide mapping, Met[O] content (%) | Peptide mapping, IsoAsp content (%) | Biopotency (%) |
|---|---|---|---|---|---|---|---|
| T3M, 40° C. | | | | 96.4 | <LOQ[b] | <LOQ[b] | 94 |
| T4M, 40° C. | 3.5 | 96.4 | 0.25 | | | | |

[a]LOQ = 0.1%
[b]LOQ = 1%
[c]analysis in duplicate

Example 6: Stability Testing of a Low Dose Formulation Containing Compound (1)

A lyophilized formulation (F14) of (1) was prepared, by lyophilization of 1060 μL in a vial. The formulation contained amounts of (1) to yield a nominal concentration of 0.80 mg CNP-38/vial and 0.75 mg CNP-38/ml after reconstitution. Formulations were placed in an incubator set to maintain 5° C., 25° C./60% RH, 30° C./65% RH and 40° C./75% RH. After 1 month (T1M), 3 months (T3M), 6 months (T6M) and 12 months (T12M), formulations were reconstituted with 1.0 mL of water and subjected to analysis.

Results show a high stability of compound (1) in the lyophilized formulation F14 as shown here for content, purity and biopotency. Moreover, the formulation showed a good stability when tested with relevant pharmacopeia methods. The lyophilized formulation was characterized by a white cake and no change in cake appearance was detected irrespective of storage. The residual moisture content was very low after lyophilization (<0.31%) and increased only slightly during the study. There was no significant change of reconstitution time during storage. Visual inspection revealed that the reconstituted solution was essentially free of visible particles (assessed in accordance with Ph. Eur. 2.9.20 and USP <790>) at the available time points. Moreover, for all samples and a low amount of subvisible particles, i.e. 0≥25 μm and 5≥10 μm were observed irrespective of storage temperature and storage time (determined with flow-through microscopy). A slight increase in colour from =WFI to <B9 was observed after 3 months storage at 30° C. and 40° C. (determined in accordance with Ph. Eur. 2.2.2 using the b-scale). Clarity was not affected during the 3 months storage and the reconstituted solution was found to be =WFI (determined in accordance with Ph. Eur. 2.2.1). pH was unaffected by storage. Finally, the osmolality at T0 was within the physiological range and no change was detected during the 3 months.

TABLE 9

| | Content of (1) (nominal, mg CNP-38 eq./mL) | Buffer | pH-adjusting buffer | pH | Trehalose dihydrate (mg/mL) |
|---|---|---|---|---|---|
| F14 | 0.75 | Succinic acid (10 mM) | Tris | 5.0 | 89 |

TABLE 10

| Sample storage conditions | Content of (1) (CNP-38 eq, mg/mL) | Purity by RP-HPLC (%) | Free CNP (%) | Purity by SE-HPLC (%) | Peptide mapping, Met[O] content (%) | Peptide mapping, IsoAsp content (%) |
|---|---|---|---|---|---|---|
| T0 | 0.70 | 99.2 | ND[a] | 98.0 | <LOQ[c] | <LOQ[c] |
| T3M, 5° C. | 0.74 | 98.9 | ND | 97.7 | <LOQ[c] | <LOQ[c] |
| T6M, 5° C. | 0.75 | 98.8 | ND | 98.0 | <LOQ[c] | <LOQ[c] |
| T12M, 5° C. | 0.74 | 98.9 | ND | 98.0 | <LOQ[c] | <LOQ[c] |
| T0 | 0.70 | 99.2 | ND | 98.0 | <LOQ[c] | <LOQ[c] |
| T1M, 25° C. | 0.74 | 98.9 | ND | 97.3 | <LOQ[c] | <LOQ[c] |
| T3M, 25° C. | 0.74 | 98.8 | ND | 97.1 | <LOQ[c] | <LOQ[c] |
| T6M, 25° C. | 0.73 | 98.7 | ND | 97.1 | <LOQ[c] | <LOQ[c] |
| T0 | 0.70 | 99.2 | ND | 98.0 | <LOQ[c] | <LOQ[c] |
| T1M, 30° C. | 0.74 | 98.8 | ND | 96.9 | <LOQ[c] | <LOQ[c] |
| T3M, 30° C. | 0.74 | 98.7 | <LOQ[b] | 96.7 | <LOQ[c] | <LOQ[c] |
| T6M, 30° C. | 0.75 | 98.4 | <LOQ[b] | 96.6 | <LOQ[c] | <LOQ[c] |
| T0 | 0.70 | 99.2 | ND | 98.0 | <LOQ[c] | <LOQ[c] |
| T1M, 40° C. | 0.76 | 98.3 | 0.10 | 96.2 | <LOQ[c] | <LOQ[c] |
| T3M, 40° C. | 0.73 | 97.9 | 0.30 | 95.6 | <LOQ[c] | <LOQ[c] |
| T6M, 40° C. | 0.73 | 97.2 | 0.47 | 95.6 | <LOQ[c] | <LOQ[c] |

[a]ND, not detected
[b]LOQ = 0.10%
[c]LOQ = 2.0%

Example 7: Stability of CNP-38 at Different pH Values

A preformulation study was carried out to assess the stability of CNP-38 at different pH values. CNP-38 (synthesized as described in WO2017/118693) was incubated at approx. 1 mg/mL in solution in succinate buffer at pH 4.0, 4.5, 5.0, 5.5 and 6.0 at 37° C. The amount of degraded CNP-38 (sum of deamidated and aspartimide variants of CNP-38) was assessed after 7 d by RP-HPLC. The amount of degraded CNP-38 was 2.7% at pH 4.0, 1.6% at pH 4.5, 1.0% at pH 5.0, 2.9% at pH 5.5 and 3.3% at pH 6.0, indicating a preferred pH of 5.0 for CNP-38 formulations.

Example 8: Stability Testing of a Formulation Containing Compound (1) Reconstituted with Water Containing an Antioxidant and/or a Preservative Lyophilized formulation (F13) of compound (1) was prepared, by lyophilizing of 1080 μL in a vial. The formulation contained appropriate-amounts of (1) to yield a nominal concentration of 3.9 mg CNP-38/vial and 3.6 mg CNP-38/ml after reconstitution with 1000 μL of water. The water contained an antioxidant and/or a preservative (R1-R5, Table 11). The vials containing reconstituted formulations were placed in an incubator set to maintain 5° C. After 4 weeks (T4W), samples were subjected to analysis.

Results show that compound (1) is stable after reconstitution under the conditions tested and not affected by the presence of an antioxidant and/or preservative (Table 12). The pH of the reconstituted solutions was not affected by antioxidant and/or preservative after reconstitution.

TABLE 11

|    | Methionine | m-Cresol    | Phenol      |
|----|------------|-------------|-------------|
| R1 | —          | —           | —           |
| R2 | 10 mM      | 0.3% (w/w)  | —           |
| R3 | 10 mM      | —           | 0.3% (w/w)  |
| R4 | —          | 0.3% (w/w)  | —           |
| R5 | —          | —           | 0.3% (w/w)  |

TABLE 12

| Sample storage conditions | Purity by RP-HPLC (%) | Free CNP (%) | Purity by SE-HPLC (%) | Peptide mapping, Met[O] content (%) | Peptide mapping, Isoasp content (%) |
|---|---|---|---|---|---|
| R1 T0 | 98.3 | <LOQ$^a$ | 97.9 | <LOQ$^b$ | <LOQ$^b$ |
| T4W, 5° C. | 98.3 | <LOQ$^a$ | 98.0 | <LOQ$^b$ | <LOQ$^b$ |
| R2 T0 | 98.4 | <LOQ$^a$ | 98.0 | <LOQ$^b$ | <LOQ$^b$ |
| T4W, 5° C. | 98.4 | <LOQ$^a$ | 97.8 | <LOQ$^b$ | <LOQ$^b$ |
| R3 T0 | 98.4 | <LOQ$^a$ | 98.1 | <LOQ$^b$ | <LOQ$^b$ |
| T4W, 5° C. | 98.3 | <LOQ$^a$ | 98.0 | <LOQ$^b$ | <LOQ$^b$ |
| R4 T0 | 98.3 | <LOQ$^a$ | 98.1 | <LOQ$^b$ | <LOQ$^b$ |
| T4W, 5° C. | 98.3 | <LOQ$^a$ | 98.0 | <LOQ$^b$ | <LOQ$^b$ |
| R5 T0 | 98.4 | <LOQ$^a$ | 98.0 | <LOQ$^b$ | <LOQ$^b$ |
| T4W, 5° C. | 98.4 | <LOQ$^a$ | 97.7 | <LOQ$^b$ | <LOQ$^b$ |

$^a$LOQ = 0.10%
$^b$LOQ = 1.0%

Abbreviations

BSA—bovine serum albumin
cGMP—cyclic guanosine monophosphate
CI—Confidence interval
DMEM—Dulbecco's Modified Eagle Medium
FBS—fetal bovine serum
HEPES—4-(2-hydroxyethyl)-1-piperazineethanesulfonic acid
IBMX—3-Isobutyl-1-methylxanthin
Isoasp—Isoaspartate
LC-MS—liquid chromatography-coupled mass spectrometry
Met(O)—methionine sulfoxide
PLA—parallel line analysis
PS 20—Polysorbate 20
PS 80—Polysorbate 80
RH—relative humidity
RP-HPLC—reversed phase high performance liquid chromatography
SE-HPLC—Size exclusion high performance liquid chromatography
TFA—trifluoroacetic acid
TR-FRET—time-resolved fluorescence energy transfer
UPLC—ultra performance liquid chromatography

SEQUENCE LISTING

<160> NUMBER OF SEQ ID NOS: 97

<210> SEQ ID NO 1
<211> LENGTH: 22
<212> TYPE: PRT
<213> ORGANISM: Homo sapiens
<220> FEATURE:
<221> NAME/KEY: DISULFID
<222> LOCATION: (6)..(22)

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 53
<212> TYPE: PRT
<213> ORGANISM: Homo sapiens
<220> FEATURE:
<221> NAME/KEY: DISULFID
<222> LOCATION: (37)..(53)

<400> SEQUENCE: 2

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

```
Ser Gly Leu Gly Cys
    50

<210> SEQ ID NO 3
<211> LENGTH: 54
<212> TYPE: PRT
<213> ORGANISM: Artificial Sequence
<220> FEATURE:
<223> OTHER INFORMATION: G-CNP-53
<220> FEATURE:
<221> NAME/KEY: DISULFID
<222> LOCATION: (38)..(54)

<400> SEQUENCE: 3

Gly Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 4
<211> LENGTH: 54
<212> TYPE: PRT
<213> ORGANISM: Artificial Sequence
<220> FEATURE:
<223> OTHER INFORMATION: M-CNP-53
<220> FEATURE:
<221> NAME/KEY: DISULFID
<222> LOCATION: (38)..(54)

<400> SEQUENCE: 4

Met Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 5
<211> LENGTH: 54
<212> TYPE: PRT
<213> ORGANISM: Artificial Sequence
<220> FEATURE:
<223> OTHER INFORMATION: P-CNP-53
<220> FEATURE:
<221> NAME/KEY: DISULFID
<222> LOCATION: (38)..(54)

<400> SEQUENCE: 5

Pro Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50
```

```
<210> SEQ ID NO 6
<211> LENGTH: 53
<212> TYPE: PRT
<213> ORGANISM: Artificial Sequence
<220> FEATURE:
<223> OTHER INFORMATION: CNP-53 M48N
<220> FEATURE:
<221> NAME/KEY: DISULFID
<222> LOCATION: (37)..(53)

<400> SEQUENCE: 6

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Asn
        35                  40                  45

Ser Gly Leu Gly Cys
    50

<210> SEQ ID NO 7
<211> LENGTH: 36
<212> TYPE: PRT
<213> ORGANISM: Artificial Sequence
<220> FEATURE:
<223> OTHER INFORMATION: CNP-53 with deletion of amino acids 15-31
<220> FEATURE:
<221> NAME/KEY: DISULFID
<222> LOCATION: (20)..(36)

<400> SEQUENCE: 7

Asp Leu Arg Val Asp Thr Lys Ser Arg Ala Ala Trp Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 8
<211> LENGTH: 52
<212> TYPE: PRT
<213> ORGANISM: Artificial Sequence
<220> FEATURE:
<223> OTHER INFORMATION: CNP-52
<220> FEATURE:
<221> NAME/KEY: DISULFID
<222> LOCATION: (36)..(52)

<400> SEQUENCE: 8

Leu Arg Val Asp Thr Lys Ser Arg Ala Ala Trp Ala Arg Leu Leu Gln
1               5                   10                  15

Glu His Pro Asn Ala Arg Lys Tyr Lys Gly Ala Asn Lys Lys Gly Leu
            20                  25                  30

Ser Lys Gly Cys Phe Gly Leu Lys Leu Asp Arg Ile Gly Ser Met Ser
        35                  40                  45

Gly Leu Gly Cys
    50

<210> SEQ ID NO 9
<211> LENGTH: 51
<212> TYPE: PRT
<213> ORGANISM: Artificial Sequence
<220> FEATURE:
<223> OTHER INFORMATION: CNP-51
```

```
<220> FEATURE:
<221> NAME/KEY: DISULFID
<222> LOCATION: (35)..(51)

<400> SEQUENCE: 9

Arg Val Asp Thr Lys Ser Arg Ala Ala Trp Ala Arg Leu Leu Gln Glu
1               5                   10                  15

His Pro Asn Ala Arg Lys Tyr Lys Gly Ala Asn Lys Lys Gly Leu Ser
            20                  25                  30

Lys Gly Cys Phe Gly Leu Lys Leu Asp Arg Ile Gly Ser Met Ser Gly
        35                  40                  45

Leu Gly Cys
    50

<210> SEQ ID NO 10
<211> LENGTH: 50
<212> TYPE: PRT
<213> ORGANISM: Artificial Sequence
<220> FEATURE:
<223> OTHER INFORMATION: CNP-50
<220> FEATURE:
<221> NAME/KEY: DISULFID
<222> LOCATION: (34)..(50)

<400> SEQUENCE: 10

Val Asp Thr Lys Ser Arg Ala Ala Trp Ala Arg Leu Leu Gln Glu His
1               5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys
    50

<210> SEQ ID NO 11
<211> LENGTH: 49
<212> TYPE: PRT
<213> ORGANISM: Artificial Sequence
<220> FEATURE:
<223> OTHER INFORMATION: CNP-49
<220> FEATURE:
<221> NAME/KEY: DISULFID
<222> LOCATION: (33)..(49)

<400> SEQUENCE: 11

Asp Thr Lys Ser Arg Ala Ala Trp Ala Arg Leu Leu Gln Glu His Pro
1               5                   10                  15

Asn Ala Arg Lys Tyr Lys Gly Ala Asn Lys Lys Gly Leu Ser Lys Gly
            20                  25                  30

Cys Phe Gly Leu Lys Leu Asp Arg Ile Gly Ser Met Ser Gly Leu Gly
        35                  40                  45

Cys

<210> SEQ ID NO 12
<211> LENGTH: 48
<212> TYPE: PRT
<213> ORGANISM: Artificial Sequence
<220> FEATURE:
<223> OTHER INFORMATION: CNP-48
<220> FEATURE:
<221> NAME/KEY: DISULFID
<222> LOCATION: (32)..(48)

<400> SEQUENCE: 12
```

```
Thr Lys Ser Arg Ala Ala Trp Ala Arg Leu Leu Gln Glu His Pro Asn
1               5                   10                  15

Ala Arg Lys Tyr Lys Gly Ala Asn Lys Gly Leu Ser Lys Gly Cys
            20                  25                  30

Phe Gly Leu Lys Leu Asp Arg Ile Gly Ser Met Ser Gly Leu Gly Cys
            35                  40                  45
```

<210> SEQ ID NO 13
<211> LENGTH: 47
<212> TYPE: PRT
<213> ORGANISM: Artificial Sequence
<220> FEATURE:
<223> OTHER INFORMATION: CNP-47
<220> FEATURE:
<221> NAME/KEY: DISULFID
<222> LOCATION: (31)..(47)

<400> SEQUENCE: 13

```
Lys Ser Arg Ala Ala Trp Ala Arg Leu Leu Gln Glu His Pro Asn Ala
1               5                   10                  15

Arg Lys Tyr Lys Gly Ala Asn Lys Lys Gly Leu Ser Lys Gly Cys Phe
            20                  25                  30

Gly Leu Lys Leu Asp Arg Ile Gly Ser Met Ser Gly Leu Gly Cys
            35                  40                  45
```

<210> SEQ ID NO 14
<211> LENGTH: 46
<212> TYPE: PRT
<213> ORGANISM: Artificial Sequence
<220> FEATURE:
<223> OTHER INFORMATION: CNP-46
<220> FEATURE:
<221> NAME/KEY: DISULFID
<222> LOCATION: (30)..(46)

<400> SEQUENCE: 14

```
Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys
            35                  40                  45
```

<210> SEQ ID NO 15
<211> LENGTH: 45
<212> TYPE: PRT
<213> ORGANISM: Artificial Sequence
<220> FEATURE:
<223> OTHER INFORMATION: CNP-45
<220> FEATURE:
<221> NAME/KEY: DISULFID
<222> LOCATION: (29)..(45)

<400> SEQUENCE: 15

```
Arg Ala Ala Trp Ala Arg Leu Leu Gln Glu His Pro Asn Ala Arg Lys
1               5                   10                  15

Tyr Lys Gly Ala Asn Lys Lys Gly Leu Ser Lys Gly Cys Phe Gly Leu
            20                  25                  30

Lys Leu Asp Arg Ile Gly Ser Met Ser Gly Leu Gly Cys
            35                  40                  45
```

<210> SEQ ID NO 16
<211> LENGTH: 44

```
<212> TYPE: PRT
<213> ORGANISM: Artificial Sequence
<220> FEATURE:
<223> OTHER INFORMATION: CNP-44
<220> FEATURE:
<221> NAME/KEY: DISULFID
<222> LOCATION: (28)..(44)

<400> SEQUENCE: 16

Ala Ala Trp Ala Arg Leu Leu Gln Glu His Pro Asn Ala Arg Lys Tyr
1               5                   10                  15

Lys Gly Ala Asn Lys Lys Gly Leu Ser Lys Gly Cys Phe Gly Leu Lys
            20                  25                  30

Leu Asp Arg Ile Gly Ser Met Ser Gly Leu Gly Cys
        35                  40

<210> SEQ ID NO 17
<211> LENGTH: 35
<212> TYPE: PRT
<213> ORGANISM: Artificial Sequence
<220> FEATURE:
<223> OTHER INFORMATION: CNP-44 with a deletion of amino acids 14-22
<220> FEATURE:
<221> NAME/KEY: DISULFID
<222> LOCATION: (19)..(35)

<400> SEQUENCE: 17

Ala Ala Trp Ala Arg Leu Leu Gln Glu His Pro Asn Ala Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 18
<211> LENGTH: 36
<212> TYPE: PRT
<213> ORGANISM: Artificial Sequence
<220> FEATURE:
<223> OTHER INFORMATION: CNP-44 with a deletion of amino acids 15-22
<220> FEATURE:
<221> NAME/KEY: DISULFID
<222> LOCATION: (20)..(36)

<400> SEQUENCE: 18

Ala Ala Trp Ala Arg Leu Leu Gln Glu His Pro Asn Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 19
<211> LENGTH: 43
<212> TYPE: PRT
<213> ORGANISM: Artificial Sequence
<220> FEATURE:
<223> OTHER INFORMATION: CNP-43
<220> FEATURE:
<221> NAME/KEY: DISULFID
<222> LOCATION: (27)..(43)

<400> SEQUENCE: 19

Ala Trp Ala Arg Leu Leu Gln Glu His Pro Asn Ala Arg Lys Tyr Lys
1               5                   10                  15
```

Gly Ala Asn Lys Lys Gly Leu Ser Lys Gly Cys Phe Gly Leu Lys Leu
            20                  25                  30

Asp Arg Ile Gly Ser Met Ser Gly Leu Gly Cys
            35                  40

<210> SEQ ID NO 20
<211> LENGTH: 42
<212> TYPE: PRT
<213> ORGANISM: Artificial Sequence
<220> FEATURE:
<223> OTHER INFORMATION: CNP-42
<220> FEATURE:
<221> NAME/KEY: DISULFID
<222> LOCATION: (26)..(42)

<400> SEQUENCE: 20

Trp Ala Arg Leu Leu Gln Glu His Pro Asn Ala Arg Lys Tyr Lys Gly
1               5                   10                  15

Ala Asn Lys Lys Gly Leu Ser Lys Gly Cys Phe Gly Leu Lys Leu Asp
            20                  25                  30

Arg Ile Gly Ser Met Ser Gly Leu Gly Cys
            35                  40

<210> SEQ ID NO 21
<211> LENGTH: 41
<212> TYPE: PRT
<213> ORGANISM: Artificial Sequence
<220> FEATURE:
<223> OTHER INFORMATION: CNP-41
<220> FEATURE:
<221> NAME/KEY: DISULFID
<222> LOCATION: (25)..(41)

<400> SEQUENCE: 21

Ala Arg Leu Leu Gln Glu His Pro Asn Ala Arg Lys Tyr Lys Gly Ala
1               5                   10                  15

Asn Lys Lys Gly Leu Ser Lys Gly Cys Phe Gly Leu Lys Leu Asp Arg
            20                  25                  30

Ile Gly Ser Met Ser Gly Leu Gly Cys
            35                  40

<210> SEQ ID NO 22
<211> LENGTH: 40
<212> TYPE: PRT
<213> ORGANISM: Artificial Sequence
<220> FEATURE:
<223> OTHER INFORMATION: CNP-40
<220> FEATURE:
<221> NAME/KEY: DISULFID
<222> LOCATION: (24)..(40)

<400> SEQUENCE: 22

Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
            20                  25                  30

Gly Ser Met Ser Gly Leu Gly Cys
            35                  40

<210> SEQ ID NO 23
<211> LENGTH: 39
<212> TYPE: PRT
<213> ORGANISM: Artificial Sequence
<220> FEATURE:
<223> OTHER INFORMATION: CNP-39

```
<220> FEATURE:
<221> NAME/KEY: DISULFID
<222> LOCATION: (23)..(39)

<400> SEQUENCE: 23

Leu Leu Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 24
<211> LENGTH: 38
<212> TYPE: PRT
<213> ORGANISM: Artificial Sequence
<220> FEATURE:
<223> OTHER INFORMATION: CNP-38
<220> FEATURE:
<221> NAME/KEY: DISULFID
<222> LOCATION: (22)..(38)

<400> SEQUENCE: 24

Leu Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35

<210> SEQ ID NO 25
<211> LENGTH: 37
<212> TYPE: PRT
<213> ORGANISM: Artificial Sequence
<220> FEATURE:
<223> OTHER INFORMATION: CNP-37
<220> FEATURE:
<221> NAME/KEY: DISULFID
<222> LOCATION: (21)..(37)

<400> SEQUENCE: 25

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 26
<211> LENGTH: 37
<212> TYPE: PRT
<213> ORGANISM: Artificial Sequence
<220> FEATURE:
<223> OTHER INFORMATION: CNP-37 mit Q1pQ (pQ = pyroglutamate)
<220> FEATURE:
<221> NAME/KEY: MISC_FEATURE
<222> LOCATION: (1)..(1)
<223> OTHER INFORMATION: X = pyroglutamate
<220> FEATURE:
<221> NAME/KEY: DISULFID
<222> LOCATION: (21)..(37)

<400> SEQUENCE: 26

Xaa Glu His Pro Asn Ala Arg Lys Tyr Lys Gly Ala Asn Lys Lys Gly
1               5                   10                  15
```

```
Leu Ser Lys Gly Cys Phe Gly Leu Lys Leu Asp Arg Ile Gly Ser Met
            20                  25                  30

Ser Gly Leu Gly Cys
        35

<210> SEQ ID NO 27
<211> LENGTH: 38
<212> TYPE: PRT
<213> ORGANISM: Artificial Sequence
<220> FEATURE:
<223> OTHER INFORMATION: G-CNP-37
<220> FEATURE:
<221> NAME/KEY: DISULFID
<222> LOCATION: (22)..(38)

<400> SEQUENCE: 27

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 28
<211> LENGTH: 38
<212> TYPE: PRT
<213> ORGANISM: Artificial Sequence
<220> FEATURE:
<223> OTHER INFORMATION: P-CNP-37
<220> FEATURE:
<221> NAME/KEY: DISULFID
<222> LOCATION: (22)..(38)

<400> SEQUENCE: 28

Pro Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 29
<211> LENGTH: 38
<212> TYPE: PRT
<213> ORGANISM: Artificial Sequence
<220> FEATURE:
<223> OTHER INFORMATION: M-CNP-37
<220> FEATURE:
<221> NAME/KEY: DISULFID
<222> LOCATION: (22)..(38)

<400> SEQUENCE: 29

Met Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 30
<211> LENGTH: 39
<212> TYPE: PRT
<213> ORGANISM: Artificial Sequence
<220> FEATURE:
<223> OTHER INFORMATION: PG-CNP-37
```

```
<220> FEATURE:
<221> NAME/KEY: DISULFID
<222> LOCATION: (23)..(39)

<400> SEQUENCE: 30

Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 31
<211> LENGTH: 39
<212> TYPE: PRT
<213> ORGANISM: Artificial Sequence
<220> FEATURE:
<223> OTHER INFORMATION: MG-CNP-37
<220> FEATURE:
<221> NAME/KEY: DISULFID
<222> LOCATION: (23)..(39)

<400> SEQUENCE: 31

Met Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 32
<211> LENGTH: 37
<212> TYPE: PRT
<213> ORGANISM: Artificial Sequence
<220> FEATURE:
<223> OTHER INFORMATION: CNP-37 M32N
<220> FEATURE:
<221> NAME/KEY: DISULFID
<222> LOCATION: (21)..(37)

<400> SEQUENCE: 32

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Asn
            20                  25                  30

Ser Gly Leu Gly Cys
            35

<210> SEQ ID NO 33
<211> LENGTH: 38
<212> TYPE: PRT
<213> ORGANISM: Artificial Sequence
<220> FEATURE:
<223> OTHER INFORMATION: G-CNP-37 M32N
<220> FEATURE:
<221> NAME/KEY: DISULFID
<222> LOCATION: (22)..(38)

<400> SEQUENCE: 33

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
```

<210> SEQ ID NO 34
<211> LENGTH: 38
<212> TYPE: PRT
<213> ORGANISM: Artificial Sequence
<220> FEATURE:
<223> OTHER INFORMATION: G-CNP-37 K14Q
<220> FEATURE:
<221> NAME/KEY: DISULFID
<222> LOCATION: (22)..(38)

<400> SEQUENCE: 34

Gly Gln Glu His Pro Asn Ala Arg Lys Tyr Lys Gly Ala Asn Gln Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 35
<211> LENGTH: 38
<212> TYPE: PRT
<213> ORGANISM: Artificial Sequence
<220> FEATURE:
<223> OTHER INFORMATION: G-CNP-37 K14P
<220> FEATURE:
<221> NAME/KEY: DISULFID
<222> LOCATION: (22)..(38)

<400> SEQUENCE: 35

Gly Gln Glu His Pro Asn Ala Arg Lys Tyr Lys Gly Ala Asn Pro Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 36
<211> LENGTH: 37
<212> TYPE: PRT
<213> ORGANISM: Artificial Sequence
<220> FEATURE:
<223> OTHER INFORMATION: G-CNP-37 K14Q, deletion of amino acid 15
<220> FEATURE:
<221> NAME/KEY: DISULFID
<222> LOCATION: (21)..(37)

<400> SEQUENCE: 36

Gly Gln Glu His Pro Asn Ala Arg Lys Tyr Lys Gly Ala Asn Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 37
<211> LENGTH: 38
<212> TYPE: PRT
<213> ORGANISM: Artificial Sequence
<220> FEATURE:
<223> OTHER INFORMATION: G-CNP-37 K14Q, K15Q
<220> FEATURE:
<221> NAME/KEY: DISULFID
<222> LOCATION: (22)..(38)

```
<400> SEQUENCE: 37

Gly Gln Glu His Pro Asn Ala Arg Lys Tyr Lys Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 38
<211> LENGTH: 36
<212> TYPE: PRT
<213> ORGANISM: Artificial Sequence
<220> FEATURE:
<223> OTHER INFORMATION: CNP-36
<220> FEATURE:
<221> NAME/KEY: DISULFID
<222> LOCATION: (20)..(36)

<400> SEQUENCE: 38

Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 39
<211> LENGTH: 35
<212> TYPE: PRT
<213> ORGANISM: Artificial Sequence
<220> FEATURE:
<223> OTHER INFORMATION: CNP-35
<220> FEATURE:
<221> NAME/KEY: DISULFID
<222> LOCATION: (19)..(35)

<400> SEQUENCE: 39

His Pro Asn Ala Arg Lys Tyr Lys Gly Ala Asn Lys Lys Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 40
<211> LENGTH: 34
<212> TYPE: PRT
<213> ORGANISM: Artificial Sequence
<220> FEATURE:
<223> OTHER INFORMATION: CNP-34
<220> FEATURE:
<221> NAME/KEY: DISULFID
<222> LOCATION: (18)..(34)

<400> SEQUENCE: 40

Pro Asn Ala Arg Lys Tyr Lys Gly Ala Asn Lys Lys Gly Leu Ser Lys
1               5                   10                  15

Gly Cys Phe Gly Leu Lys Leu Asp Arg Ile Gly Ser Met Ser Gly Leu
            20                  25                  30

Gly Cys

<210> SEQ ID NO 41
<211> LENGTH: 33
```

```
<212> TYPE: PRT
<213> ORGANISM: Artificial Sequence
<220> FEATURE:
<223> OTHER INFORMATION: CNP-33
<220> FEATURE:
<221> NAME/KEY: DISULFID
<222> LOCATION: (17)..(33)

<400> SEQUENCE: 41

Asn Ala Arg Lys Tyr Lys Gly Ala Asn Lys Lys Gly Leu Ser Lys Gly
1               5                   10                  15

Cys Phe Gly Leu Lys Leu Asp Arg Ile Gly Ser Met Ser Gly Leu Gly
                20                  25                  30

Cys

<210> SEQ ID NO 42
<211> LENGTH: 32
<212> TYPE: PRT
<213> ORGANISM: Artificial Sequence
<220> FEATURE:
<223> OTHER INFORMATION: CNP-32
<220> FEATURE:
<221> NAME/KEY: DISULFID
<222> LOCATION: (16)..(32)

<400> SEQUENCE: 42

Ala Arg Lys Tyr Lys Gly Ala Asn Lys Lys Gly Leu Ser Lys Gly Cys
1               5                   10                  15

Phe Gly Leu Lys Leu Asp Arg Ile Gly Ser Met Ser Gly Leu Gly Cys
                20                  25                  30

<210> SEQ ID NO 43
<211> LENGTH: 31
<212> TYPE: PRT
<213> ORGANISM: Artificial Sequence
<220> FEATURE:
<223> OTHER INFORMATION: CNP-31
<220> FEATURE:
<221> NAME/KEY: DISULFID
<222> LOCATION: (15)..(31)

<400> SEQUENCE: 43

Arg Lys Tyr Lys Gly Ala Asn Lys Lys Gly Leu Ser Lys Gly Cys Phe
1               5                   10                  15

Gly Leu Lys Leu Asp Arg Ile Gly Ser Met Ser Gly Leu Gly Cys
                20                  25                  30

<210> SEQ ID NO 44
<211> LENGTH: 30
<212> TYPE: PRT
<213> ORGANISM: Artificial Sequence
<220> FEATURE:
<223> OTHER INFORMATION: CNP-30
<220> FEATURE:
<221> NAME/KEY: DISULFID
<222> LOCATION: (14)..(30)

<400> SEQUENCE: 44

Lys Tyr Lys Gly Ala Asn Lys Lys Gly Leu Ser Lys Gly Cys Phe Gly
1               5                   10                  15

Leu Lys Leu Asp Arg Ile Gly Ser Met Ser Gly Leu Gly Cys
                20                  25                  30

<210> SEQ ID NO 45
<211> LENGTH: 29
<212> TYPE: PRT
```

<213> ORGANISM: Artificial Sequence
<220> FEATURE:
<223> OTHER INFORMATION: CNP-29
<220> FEATURE:
<221> NAME/KEY: DISULFID
<222> LOCATION: (13)..(29)

<400> SEQUENCE: 45

Tyr Lys Gly Ala Asn Lys Lys Gly Leu Ser Lys Gly Cys Phe Gly Leu
1               5                   10                  15
Lys Leu Asp Arg Ile Gly Ser Met Ser Gly Leu Gly Cys
            20                  25

<210> SEQ ID NO 46
<211> LENGTH: 28
<212> TYPE: PRT
<213> ORGANISM: Artificial Sequence
<220> FEATURE:
<223> OTHER INFORMATION: CNP-28
<220> FEATURE:
<221> NAME/KEY: DISULFID
<222> LOCATION: (12)..(28)

<400> SEQUENCE: 46

Lys Gly Ala Asn Lys Lys Gly Leu Ser Lys Gly Cys Phe Gly Leu Lys
1               5                   10                  15
Leu Asp Arg Ile Gly Ser Met Ser Gly Leu Gly Cys
            20                  25

<210> SEQ ID NO 47
<211> LENGTH: 38
<212> TYPE: PRT
<213> ORGANISM: Artificial Sequence
<220> FEATURE:
<223> OTHER INFORMATION: GHKSEVAHRF-CNP-28
<220> FEATURE:
<221> NAME/KEY: DISULFID
<222> LOCATION: (22)..(38)

<400> SEQUENCE: 47

Gly His Lys Ser Glu Val Ala His Arg Phe Lys Gly Ala Asn Lys Lys
1               5                   10                  15
Gly Leu Ser Lys Gly Cys Phe Gly Leu Lys Leu Asp Arg Ile Gly Ser
            20                  25                  30
Met Ser Gly Leu Gly Cys
        35

<210> SEQ ID NO 48
<211> LENGTH: 27
<212> TYPE: PRT
<213> ORGANISM: Artificial Sequence
<220> FEATURE:
<223> OTHER INFORMATION: CNP-27
<220> FEATURE:
<221> NAME/KEY: DISULFID
<222> LOCATION: (11)..(27)

<400> SEQUENCE: 48

Gly Ala Asn Lys Lys Gly Leu Ser Lys Gly Cys Phe Gly Leu Lys Leu
1               5                   10                  15
Asp Arg Ile Gly Ser Met Ser Gly Leu Gly Cys
            20                  25

<210> SEQ ID NO 49
<211> LENGTH: 27
<212> TYPE: PRT

```
<213> ORGANISM: Artificial Sequence
<220> FEATURE:
<223> OTHER INFORMATION: CNP-27 K4Q, K5Q
<220> FEATURE:
<221> NAME/KEY: DISULFID
<222> LOCATION: (11)..(27)

<400> SEQUENCE: 49

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 50
<211> LENGTH: 27
<212> TYPE: PRT
<213> ORGANISM: Artificial Sequence
<220> FEATURE:
<223> OTHER INFORMATION: CNP-27 K4R, K5R
<220> FEATURE:
<221> NAME/KEY: DISULFID
<222> LOCATION: (11)..(27)

<400> SEQUENCE: 50

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 51
<211> LENGTH: 27
<212> TYPE: PRT
<213> ORGANISM: Artificial Sequence
<220> FEATURE:
<223> OTHER INFORMATION: CNP-27 K4P, K5R
<220> FEATURE:
<221> NAME/KEY: DISULFID
<222> LOCATION: (11)..(27)

<400> SEQUENCE: 51

Gly Ala Asn Pro Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 52
<211> LENGTH: 27
<212> TYPE: PRT
<213> ORGANISM: Artificial Sequence
<220> FEATURE:
<223> OTHER INFORMATION: CNP-27 K4S, K5S
<220> FEATURE:
<221> NAME/KEY: DISULFID
<222> LOCATION: (11)..(27)

<400> SEQUENCE: 52

Gly Ala Asn Ser Ser Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 53
<211> LENGTH: 30
<212> TYPE: PRT
<213> ORGANISM: Artificial Sequence
<220> FEATURE:
<223> OTHER INFORMATION: GAN-CNP-27 K4P, K5R
```

```
<220> FEATURE:
<221> NAME/KEY: DISULFID
<222> LOCATION: (14)..(30)

<400> SEQUENCE: 53

Gly Ala Asn Gly Ala Asn Pro Arg Gly Leu Ser Arg Gly Cys Phe Gly
1               5                   10                  15

Leu Lys Leu Asp Arg Ile Gly Ser Met Ser Gly Leu Gly Cys
            20                  25                  30

<210> SEQ ID NO 54
<211> LENGTH: 27
<212> TYPE: PRT
<213> ORGANISM: Artificial Sequence
<220> FEATURE:
<223> OTHER INFORMATION: CNP-27 K4R, K5R, K9R
<220> FEATURE:
<221> NAME/KEY: DISULFID
<222> LOCATION: (11)..(27)

<400> SEQUENCE: 54

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 55
<211> LENGTH: 27
<212> TYPE: PRT
<213> ORGANISM: Artificial Sequence
<220> FEATURE:
<223> OTHER INFORMATION: CNP-27 K4R, K5R, K9R, M22N
<220> FEATURE:
<221> NAME/KEY: DISULFID
<222> LOCATION: (11)..(27)

<400> SEQUENCE: 55

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 56
<211> LENGTH: 28
<212> TYPE: PRT
<213> ORGANISM: Artificial Sequence
<220> FEATURE:
<223> OTHER INFORMATION: P-CNP-27 K4R, K5R, K9R
<220> FEATURE:
<221> NAME/KEY: DISULFID
<222> LOCATION: (12)..(28)

<400> SEQUENCE: 56

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 57
<211> LENGTH: 28
<212> TYPE: PRT
<213> ORGANISM: Artificial Sequence
<220> FEATURE:
<223> OTHER INFORMATION: M-CNP-27 K4R, K5R, K9R
<220> FEATURE:
<221> NAME/KEY: DISULFID
<222> LOCATION: (12)..(28)
```

<400> SEQUENCE: 57

Met Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 58
<211> LENGTH: 38
<212> TYPE: PRT
<213> ORGANISM: Artificial Sequence
<220> FEATURE:
<223> OTHER INFORMATION: Human Serum Albumine Fragment - CNP-27
<220> FEATURE:
<221> NAME/KEY: DISULFID
<222> LOCATION: (22)..(38)

<400> SEQUENCE: 58

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35

<210> SEQ ID NO 59
<211> LENGTH: 38
<212> TYPE: PRT
<213> ORGANISM: Artificial Sequence
<220> FEATURE:
<223> OTHER INFORMATION: Human Serum Albumine Fragment - CNP-27 M22N
<220> FEATURE:
<221> NAME/KEY: DISULFID
<222> LOCATION: (22)..(38)

<400> SEQUENCE: 59

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
            35

<210> SEQ ID NO 60
<211> LENGTH: 39
<212> TYPE: PRT
<213> ORGANISM: Artificial Sequence
<220> FEATURE:
<223> OTHER INFORMATION: methionine - Human Serum Albumine Fragment -
      CNP-27
<220> FEATURE:
<221> NAME/KEY: DISULFID
<222> LOCATION: (23)..(39)

<400> SEQUENCE: 60

Met Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 61
<211> LENGTH: 39

```
<212> TYPE: PRT
<213> ORGANISM: Artificial Sequence
<220> FEATURE:
<223> OTHER INFORMATION: proline - Human Serum Albumine Fragment -
      CNP-27
<220> FEATURE:
<221> NAME/KEY: DISULFID
<222> LOCATION: (23)..(39)

<400> SEQUENCE: 61

Pro Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 62
<211> LENGTH: 26
<212> TYPE: PRT
<213> ORGANISM: Artificial Sequence
<220> FEATURE:
<223> OTHER INFORMATION: CNP-26
<220> FEATURE:
<221> NAME/KEY: DISULFID
<222> LOCATION: (10)..(26)

<400> SEQUENCE: 62

Ala Asn Lys Lys Gly Leu Ser Lys Gly Cys Phe Gly Leu Lys Leu Asp
1               5                   10                  15

Arg Ile Gly Ser Met Ser Gly Leu Gly Cys
            20                  25

<210> SEQ ID NO 63
<211> LENGTH: 25
<212> TYPE: PRT
<213> ORGANISM: Artificial Sequence
<220> FEATURE:
<223> OTHER INFORMATION: CNP-25
<220> FEATURE:
<221> NAME/KEY: DISULFID
<222> LOCATION: (9)..(25)

<400> SEQUENCE: 63

Asn Lys Lys Gly Leu Ser Lys Gly Cys Phe Gly Leu Lys Leu Asp Arg
1               5                   10                  15

Ile Gly Ser Met Ser Gly Leu Gly Cys
            20                  25

<210> SEQ ID NO 64
<211> LENGTH: 24
<212> TYPE: PRT
<213> ORGANISM: Artificial Sequence
<220> FEATURE:
<223> OTHER INFORMATION: CNP-24
<220> FEATURE:
<221> NAME/KEY: DISULFID
<222> LOCATION: (8)..(24)

<400> SEQUENCE: 64

Lys Lys Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 65
```

```
<211> LENGTH: 23
<212> TYPE: PRT
<213> ORGANISM: Artificial Sequence
<220> FEATURE:
<223> OTHER INFORMATION: CNP-23
<220> FEATURE:
<221> NAME/KEY: DISULFID
<222> LOCATION: (7)..(23)

<400> SEQUENCE: 65

Lys Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 66
<211> LENGTH: 23
<212> TYPE: PRT
<213> ORGANISM: Artificial Sequence
<220> FEATURE:
<223> OTHER INFORMATION: R-CNP-22
<220> FEATURE:
<221> NAME/KEY: DISULFID
<222> LOCATION: (7)..(23)

<400> SEQUENCE: 66

Arg Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 67
<211> LENGTH: 24
<212> TYPE: PRT
<213> ORGANISM: Artificial Sequence
<220> FEATURE:
<223> OTHER INFORMATION: ER-CNP-22
<220> FEATURE:
<221> NAME/KEY: DISULFID
<222> LOCATION: (8)..(24)

<400> SEQUENCE: 67

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 68
<211> LENGTH: 23
<212> TYPE: PRT
<213> ORGANISM: Artificial Sequence
<220> FEATURE:
<223> OTHER INFORMATION: R-CNP-22 K4R
<220> FEATURE:
<221> NAME/KEY: DISULFID
<222> LOCATION: (7)..(23)

<400> SEQUENCE: 68

Arg Gly Leu Ser Arg Gly Cys Phe Gly Leu Lys Leu Asp Arg Ile Gly
1               5                   10                  15

Ser Met Ser Gly Leu Gly Cys
            20

<210> SEQ ID NO 69
<211> LENGTH: 24
<212> TYPE: PRT
<213> ORGANISM: Artificial Sequence
```

```
<220> FEATURE:
<223> OTHER INFORMATION: ER-CNP-22 4KR
<220> FEATURE:
<221> NAME/KEY: DISULFID
<222> LOCATION: (8)..(24)

<400> SEQUENCE: 69

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 70
<211> LENGTH: 24
<212> TYPE: PRT
<213> ORGANISM: Artificial Sequence
<220> FEATURE:
<223> OTHER INFORMATION: RR-CNP-22
<220> FEATURE:
<221> NAME/KEY: DISULFID
<222> LOCATION: (8)..(24)

<400> SEQUENCE: 70

Arg Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 71
<211> LENGTH: 37
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (21)..(37)

<400> SEQUENCE: 71

Gly His His Ser His Glu Gln His Pro His Gly Ala Asn Gln Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 72
<211> LENGTH: 38
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (22)..(38)

<400> SEQUENCE: 72

Gly Ala His His Pro His Glu His Asp Thr His Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 73
```

```
<211> LENGTH: 37
<212> TYPE: PRT
<213> ORGANISM: Artificial Sequence
<220> FEATURE:
<223> OTHER INFORMATION: HRGP fragment - CNP-22
<220> FEATURE:
<221> NAME/KEY: DISULFID
<222> LOCATION: (21)..(37)

<400> SEQUENCE: 73

Gly His His Ser His Glu Gln His Pro His Gly Ala Asn Pro Arg Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 74
<211> LENGTH: 36
<212> TYPE: PRT
<213> ORGANISM: Artificial Sequence
<220> FEATURE:
<223> OTHER INFORMATION: IgG1(FC) fragment - CNP-22
<220> FEATURE:
<221> NAME/KEY: DISULFID
<222> LOCATION: (20)..(36)

<400> SEQUENCE: 74

Gly Gln Pro Arg Glu Pro Gln Val Tyr Thr Leu Pro Pro Ser Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 75
<211> LENGTH: 39
<212> TYPE: PRT
<213> ORGANISM: Artificial Sequence
<220> FEATURE:
<223> OTHER INFORMATION: Human Serum Albumine - CNP-22
<220> FEATURE:
<221> NAME/KEY: DISULFID
<222> LOCATION: (23)..(39)

<400> SEQUENCE: 75

Gly Gln His Lys Asp Asp Asn Pro Asn Leu Pro Arg Gly Ala Asn Pro
1               5                   10                  15

Arg Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 76
<211> LENGTH: 37
<212> TYPE: PRT
<213> ORGANISM: Artificial Sequence
<220> FEATURE:
<223> OTHER INFORMATION: Human Serum Albumine - CNP-22
<220> FEATURE:
<221> NAME/KEY: DISULFID
<222> LOCATION: (21)..(37)

<400> SEQUENCE: 76

Gly Glu Arg Ala Phe Lys Ala Trp Ala Val Ala Arg Leu Ser Gln Gly
1               5                   10                  15
```

-continued

```
Leu Ser Lys Gly Cys Phe Gly Leu Lys Leu Asp Arg Ile Gly Ser Met
            20                  25                  30

Ser Gly Leu Gly Cys
        35

<210> SEQ ID NO 77
<211> LENGTH: 35
<212> TYPE: PRT
<213> ORGANISM: Artificial Sequence
<220> FEATURE:
<223> OTHER INFORMATION: osteocrin NPR C inhibitor fragment - CNP-22
<220> FEATURE:
<221> NAME/KEY: DISULFID
<222> LOCATION: (19)..(35)

<400> SEQUENCE: 77

Phe Gly Ile Pro Met Asp Arg Ile Gly Arg Asn Pro Arg Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 78
<211> LENGTH: 40
<212> TYPE: PRT
<213> ORGANISM: Artificial Sequence
<220> FEATURE:
<223> OTHER INFORMATION: FGF2 heparin-binding domain fragment - CNP-22
<220> FEATURE:
<221> NAME/KEY: DISULFID
<222> LOCATION: (24)..(40)

<400> SEQUENCE: 78

Gly Lys Arg Thr Gly Gln Tyr Lys Leu Gly Ser Lys Thr Gly Pro Gly
1               5                   10                  15

Pro Lys Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 79
<211> LENGTH: 37
<212> TYPE: PRT
<213> ORGANISM: Artificial Sequence
<220> FEATURE:
<223> OTHER INFORMATION: IgG1(FC) fragment - CNP-22 K4R
<220> FEATURE:
<221> NAME/KEY: DISULFID
<222> LOCATION: (21)..(37)

<400> SEQUENCE: 79

Gly Gln Pro Arg Glu Pro Gln Val Tyr Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 80
<211> LENGTH: 36
<212> TYPE: PRT
<213> ORGANISM: Artificial Sequence
<220> FEATURE:
```

<223> OTHER INFORMATION: Human Serum Albumine fragment - CNP-22 K4R
<220> FEATURE:
<221> NAME/KEY: DISULFID
<222> LOCATION: (20)..(36)

<400> SEQUENCE: 80

Gly Val Pro Gln Val Ser Thr Ser Thr Gly Ala Asn Gln Gln Gly Leu
1               5                   10                  15

Ser Arg Gly Cys Phe Gly Leu Lys Leu Asp Arg Ile Gly Ser Met Ser
            20                  25                  30

Gly Leu Gly Cys
            35

<210> SEQ ID NO 81
<211> LENGTH: 37
<212> TYPE: PRT
<213> ORGANISM: Artificial Sequence
<220> FEATURE:
<223> OTHER INFORMATION: fibronectin fragment - CNP-22
<220> FEATURE:
<221> NAME/KEY: DISULFID
<222> LOCATION: (21)..(37)

<400> SEQUENCE: 81

Gly Gln Pro Ser Ser Ser Ser Gln Ser Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
            35

<210> SEQ ID NO 82
<211> LENGTH: 37
<212> TYPE: PRT
<213> ORGANISM: Artificial Sequence
<220> FEATURE:
<223> OTHER INFORMATION: fibronectin fragment - CNP-22 K4R
<220> FEATURE:
<221> NAME/KEY: DISULFID
<222> LOCATION: (21)..(37)

<400> SEQUENCE: 82

Gly Gln Thr His Ser Ser Gly Thr Gln Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
            35

<210> SEQ ID NO 83
<211> LENGTH: 37
<212> TYPE: PRT
<213> ORGANISM: Artificial Sequence
<220> FEATURE:
<223> OTHER INFORMATION: fibronectin fragment - CNP-22 K4R
<220> FEATURE:
<221> NAME/KEY: DISULFID
<222> LOCATION: (21)..(37)

<400> SEQUENCE: 83

Gly Ser Thr Gly Gln Trp His Ser Glu Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 84
<211> LENGTH: 37
<212> TYPE: PRT
<213> ORGANISM: Artificial Sequence
<220> FEATURE:
<223> OTHER INFORMATION: zinc finger fragment - CNP-22 K4R
<220> FEATURE:
<221> NAME/KEY: DISULFID
<222> LOCATION: (21)..(37)

<400> SEQUENCE: 84

Gly Ser Ser Ser Ser Ser Ser Ser Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 85
<211> LENGTH: 21
<212> TYPE: PRT
<213> ORGANISM: Artificial Sequence
<220> FEATURE:
<223> OTHER INFORMATION: CNP-21
<220> FEATURE:
<221> NAME/KEY: DISULFID
<222> LOCATION: (5)..(21)

<400> SEQUENCE: 85

Leu Ser Lys Gly Cys Phe Gly Leu Lys Leu Asp Arg Ile Gly Ser Met
1               5                   10                  15

Ser Gly Leu Gly Cys
            20

<210> SEQ ID NO 86
<211> LENGTH: 20
<212> TYPE: PRT
<213> ORGANISM: Artificial Sequence
<220> FEATURE:
<223> OTHER INFORMATION: CNP-20
<220> FEATURE:
<221> NAME/KEY: DISULFID
<222> LOCATION: (4)..(20)

<400> SEQUENCE: 86

Ser Lys Gly Cys Phe Gly Leu Lys Leu Asp Arg Ile Gly Ser Met Ser
1               5                   10                  15

Gly Leu Gly Cys
        20

<210> SEQ ID NO 87
<211> LENGTH: 19
<212> TYPE: PRT
<213> ORGANISM: Artificial Sequence
<220> FEATURE:
<223> OTHER INFORMATION: CNP-19
<220> FEATURE:
<221> NAME/KEY: DISULFID
<222> LOCATION: (3)..(19)

<400> SEQUENCE: 87

Lys Gly Cys Phe Gly Leu Lys Leu Asp Arg Ile Gly Ser Met Ser Gly
1               5                   10                  15

Leu Gly Cys

<210> SEQ ID NO 88
<211> LENGTH: 18
<212> TYPE: PRT
<213> ORGANISM: Artificial Sequence
<220> FEATURE:
<223> OTHER INFORMATION: CNP-18
<220> FEATURE:
<221> NAME/KEY: DISULFID
<222> LOCATION: (2)..(18)

<400> SEQUENCE: 88

Gly Cys Phe Gly Leu Lys Leu Asp Arg Ile Gly Ser Met Ser Gly Leu
1               5                   10                  15

Gly Cys

<210> SEQ ID NO 89
<211> LENGTH: 17
<212> TYPE: PRT
<213> ORGANISM: Artificial Sequence
<220> FEATURE:
<223> OTHER INFORMATION: CNP-17
<220> FEATURE:
<221> NAME/KEY: DISULFID
<222> LOCATION: (1)..(17)

<400> SEQUENCE: 89

Cys Phe Gly Leu Lys Leu Asp Arg Ile Gly Ser Met Ser Gly Leu Gly
1               5                   10                  15

Cys

<210> SEQ ID NO 90
<211> LENGTH: 32
<212> TYPE: PRT
<213> ORGANISM: Artificial Sequence
<220> FEATURE:
<223> OTHER INFORMATION: BNP fragment - CNP-17 - BNP- fragment
<220> FEATURE:
<221> NAME/KEY: DISULFID
<222> LOCATION: (10)..(26)

<400> SEQUENCE: 90

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 91
<211> LENGTH: 38
<212> TYPE: PRT
<213> ORGANISM: Artificial Sequence
<220> FEATURE:
<223> OTHER INFORMATION: CNP-38 L1G
<220> FEATURE:
<221> NAME/KEY: DISULFID
<222> LOCATION: (22)..(38)

<400> SEQUENCE: 91

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

```
<210> SEQ ID NO 92
<211> LENGTH: 37
<212> TYPE: PRT
<213> ORGANISM: Artificial Sequence
<220> FEATURE:
<223> OTHER INFORMATION: Ac-CNP-37
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (21)..(37)

<400> SEQUENCE: 92

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 93
<211> LENGTH: 37
<212> TYPE: PRT
<213> ORGANISM: Artificial Sequence
<220> FEATURE:
<223> OTHER INFORMATION: CNP-37, Xaa = K or R, with the provision that
      at least one Xaa is R
<220> FEATURE:
<221> NAME/KEY: MISC_FEATURE
<222> LOCATION: (8)..(8)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (10)..(10)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (14)..(14)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (15)..(15)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: MISC_FEATURE
<222> LOCATION: (19)..(19)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln
<220> FEATURE:
<221> NAME/KEY: DISULFID
<222> LOCATION: (21)..(37)
<220> FEATURE:
<221> NAME/KEY: MISC_FEATURE
<222> LOCATION: (25)..(25)
<223> OTHER INFORMATION: Xaa = Lys, Arg, Pro, Ser or Gln, with the
      provision that at least one of amino acids 8, 10, 14, 15, 19 or 25
      is selected from the group consisting of Arg, Pro, Ser and Gln

<400> SEQUENCE: 93

Gln Glu His Pro Asn Ala Arg Xaa Tyr Xaa Gly Ala Asn Xaa Xaa Gly
1               5                   10                  15
```

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 94
<211> LENGTH: 37
<212> TYPE: PRT
<213> ORGANISM: Artificial Sequence
<220> FEATURE:
<223> OTHER INFORMATION: mutated CNP-37
<220> FEATURE:
<221> NAME/KEY: MISC_FEATURE
<222> LOCATION: (14)..(14)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of Arg, Pro, Ser and Gln
<220> FEATURE:
<221> NAME/KEY: MISC_FEATURE
<222> LOCATION: (15)..(15)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of Arg, Pro, Ser and Gln
<220> FEATURE:
<221> NAME/KEY: MISC_FEATURE
<222> LOCATION: (19)..(19)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of Arg, Pro, Ser and Gln
<220> FEATURE:
<221> NAME/KEY: DISULFID
<222> LOCATION: (21)..(37)
<220> FEATURE:
<221> NAME/KEY: MISC_FEATURE
<222> LOCATION: (25)..(25)
<223> OTHER INFORMATION: X is selected from the group consising of Lys,
      Arg, Pro, Ser and Gln, with the provision that at least one of the
      amino acids at position 14, 15, 19 and 25 is selected from the
      group consisting of Arg, Pro, Ser and Gln

<400> SEQUENCE: 94

Gln Glu His Pro Asn Ala Arg Lys Tyr Lys Gly Ala Asn Xaa Xaa Gly
1               5                   10                  15

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 95
<211> LENGTH: 37
<212> TYPE: PRT
<213> ORGANISM: Artificial Sequence
<220> FEATURE:
<223> OTHER INFORMATION: mutated CNP-37
<220> FEATURE:
<221> NAME/KEY: MISC_FEATURE
<222> LOCATION: (14)..(15)
<223> OTHER INFORMATION: Xaa Xaa is selected from the group consisting
      of Lys Arg, Arg Lys, Lys Pro, Pro Lys, Ser Ser, Arg Ser, Ser Arg,
      Gln Lys, Gln Arg, Lys Gln, Arg Gln, Arg Arg and Gln Gln
<220> FEATURE:
<221> NAME/KEY: DISULFID
<222> LOCATION: (21)..(37)

<400> SEQUENCE: 95

Gln Glu His Pro Asn Ala Arg Lys Tyr Lys Gly Ala Asn Xaa Xaa Gly
1               5                   10                  15

Leu Ser Lys Gly Cys Phe Gly Leu Lys Leu Asp Arg Ile Gly Ser Met

```
                20              25              30
Ser Gly Leu Gly Cys
        35

<210> SEQ ID NO 96
<211> LENGTH: 15
<212> TYPE: PRT
<213> ORGANISM: Homo sapiens

<400> SEQUENCE: 96

Phe Gly Leu Lys Leu Asp Arg Ile Gly Ser Met Ser Gly Leu Gly
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Artificial random coil

<400> SEQUENCE: 97

Gly Gly Pro Gly Gly Pro Gly Pro Gly Gly Pro Gly Gly Pro Gly Pro
1               5                   10                  15

Gly Gly Pro Gly
            20
```

The invention claimed is:

1. A dry pharmaceutical formulation, wherein the pharmaceutical formulation comprises based on the total weight of the dry pharmaceutical formulation: a CNP conjugate at 1.3-45.4% (w/w), succinic acid at 0.2-3.2% (w/w), trehalose dihydrate at 52.6-98.4% (w/w), and Tris at 0.1-5.6% (w/w); wherein
the formulation is reconstitutable with water to pH 4-6; wherein the CNP conjugate comprises CNP-38 (SEQ ID NO:24) reversibly conjugated to a branched PEG polymer of 12-60 kDa.

2. The dry pharmaceutical formulation of claim 1, wherein the formulation comprises based on the total weight of the dry pharmaceutical formulation:
the CNP conjugate at 1.3-38.7% (w/w).

3. The dry pharmaceutical formulation of claim 1, wherein the CNP conjugate is of formula (Ia) or (Ib):

   (Ia)

   (Ib), wherein
D is the CNP-38;
-L$^1$- is a reversible linker moiety;
-L$^2$- is a single chemical bond or a spacer moiety;
Z is the branched PEG polymer;
x is an integer selected from the group consisting of 1, 2, 3, 4, 5, 6, 7, 8, 9, 10, 11, 12, 13, 14, 15 and 16; and
y is an integer selected from the group consisting of 1, 2, 3, 4 and 5.

4. The dry pharmaceutical formulation of claim 3, wherein x of formula (Ia) is an integer selected from the group consisting of 1, 2, 3, 4, 6 and 8.

5. The dry pharmaceutical formulation of claim 3, wherein y of formula (Ib) is an integer selected from the group consisting of 2, 3, 4 and 5.

6. The dry pharmaceutical formulation of claim 3, wherein the CNP conjugate is of formula (Ia) and x is 1.

7. The dry pharmaceutical formulation of claim 3, wherein
-L$^1$- is connected to -D through an amide linkage.

8. The dry pharmaceutical formulation of claim 3, wherein -L$^2$- is a spacer moiety.

9. The dry pharmaceutical formulation of claim 3, wherein -L$^2$- has a molecular weight ranging from 14 g/mol to 750 g/mol.

10. The dry pharmaceutical formulation of claim 3, wherein -L$^2$- has a chain length of 1 to 20 atoms.

11. The dry pharmaceutical formulation of claim 3, wherein -L$^2$- is of formula (i):

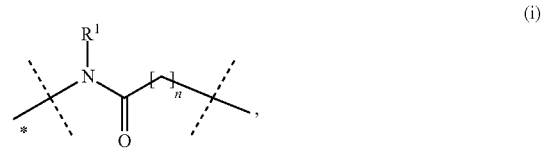   (i)

wherein
the dashed line marked with the asterisk indicates attachment to -L$^1$-;
the unmarked dashed line indicates attachment to -Z;
-R$^1$ is selected from the group consisting of —H, C$_{1-6}$ alkyl, C$_{2-6}$ alkenyl and C$_{2-6}$ alkynyl;
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

12. The dry pharmaceutical formulation of claim 11, wherein n of formula (i) is selected from the group consisting of 3, 4, 5, 6, 7, 8 and 9.

13. A method of manufacturing the dry pharmaceutical formulation of claim 1, wherein the method comprises the steps of (i) admixing the CNP conjugate with at least a buffering agent and a bulking agent;
ii adjusting the pH of the admixture of step (i);
iii) optionally, filtering the admixture from step (ii);
(iv) transferring amounts of the admixture from step (ii) or (iii) equivalent to the desired number of dosages into a container;
(v) drying the admixture;
(vi) sealing the container; and
wherein the order of steps (ii) and (iii) may optionally be reversed.

14. A method of reconstituting the dry pharmaceutical formulation of claim 1, wherein the method comprises the step of
   (a) contacting the dry pharmaceutical formulation of claim 1, with a reconstitution solution.

15. A reconstituted pharmaceutical formulation obtainable from the method of reconstituting of claim 14.

16. A method of treating, controlling, delaying or preventing in a patient one or more diseases which can be treated by CNP, the method comprising administering to the patient a therapeutically effective amount of the reconstitution pharmaceutical formulation of claim 15 wherein the disease is achondroplasia.

17. The dry pharmaceutical formulation of claim 1, wherein the dry pharmaceutical formulation comprises a mixture of one or more acid and base pH-adjusting agents.

18. The dry pharmaceutical formulation of claim 1 that is free of antioxidants.

19. The dry pharmaceutical formulation of claim 18 that is free of surfactants.

20. The dry pharmaceutical formulation of claim 1, wherein the CNP conjugate is of formula (IIf):

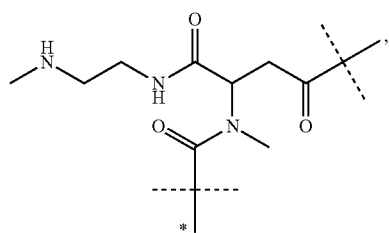

(IIf)

or a pharmaceutically acceptable salt thereof;
   wherein
   the unmarked dashed line indicates the attachment to a nitrogen provided by the side chain of the lysine at position 26 of a CNP moiety of SEQ ID NO:24 by forming an amide bond; and
   the dashed line marked with the asterisk indicates attachment to -Z having the structure

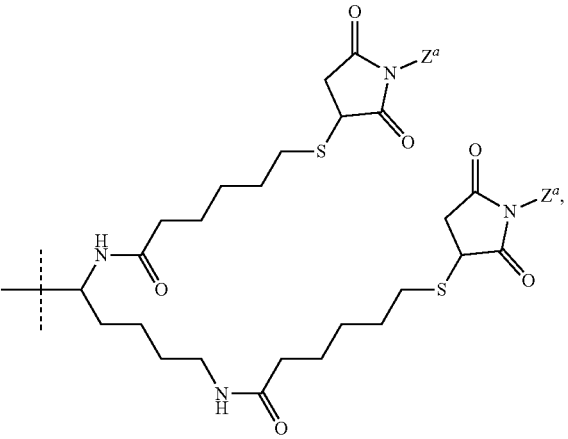

wherein
   each $Z^a$ is $$\begin{array}{c}\phantom{xxx}\text{CH}_2\text{--}[\text{O--CH}_2\text{--CH}_2]_{c1}\text{--O--CH}_3\\ \phantom{xxx} | \\ \phantom{xxx}\text{CH}\text{--}[\text{O--CH}_2\text{--CH}_2]_{c1}\text{--O--CH}_3 \\ \phantom{xxx} | \\ \text{---CH}_2\text{--CH}_2\text{--C(=O)--NH--CH}_2\text{--CH}_2\text{--CH}_2\text{--O--CH}_2\end{array}$$

wherein
   each c1 is an integer independently ranging from 200 to 250.

21. The dry pharmaceutical formulation of claim 20, wherein each c1 is about 225.

22. The dry pharmaceutical formulation of claim of claim 2 of formula (IIf')

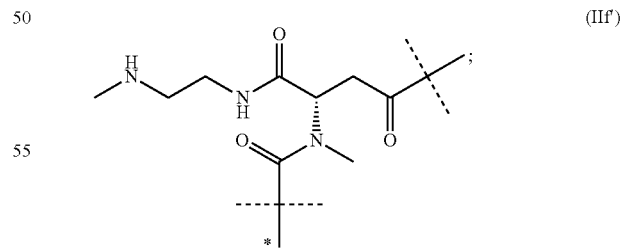

(IIf')

wherein
   the unmarked dashed line indicates the attachment to a nitrogen provided by the side chain of the lysine at position 26 of a CNP moiety of SEQ ID NO:24 by forming an amide bond; and
   the dashed line marked with the asterisk indicates attachment to -Z having the structure

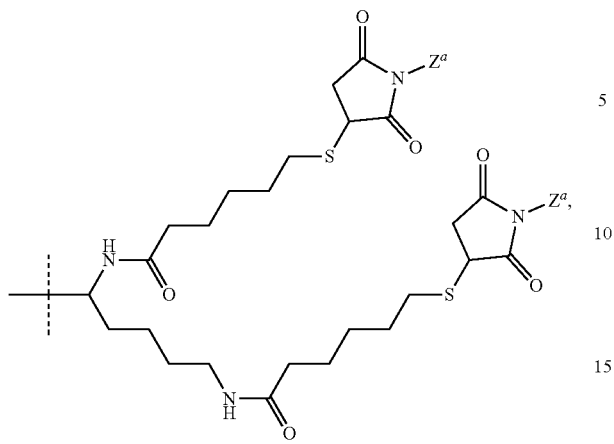
wherein each -$Z^a$ is
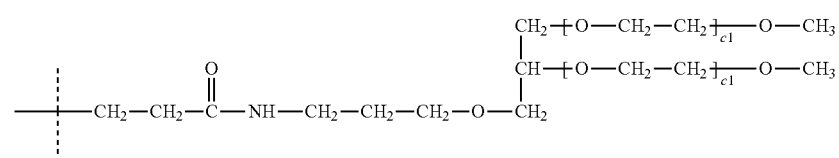
wherein
each c1 is an integer independently ranging from 200 to 250.
23. The dry pharmaceutical formulation of claim 22, wherein each c1 is about 225.
24. The dry pharmaceutical formulation of claim 22, wherein -Z has the structure of formula (h-i):
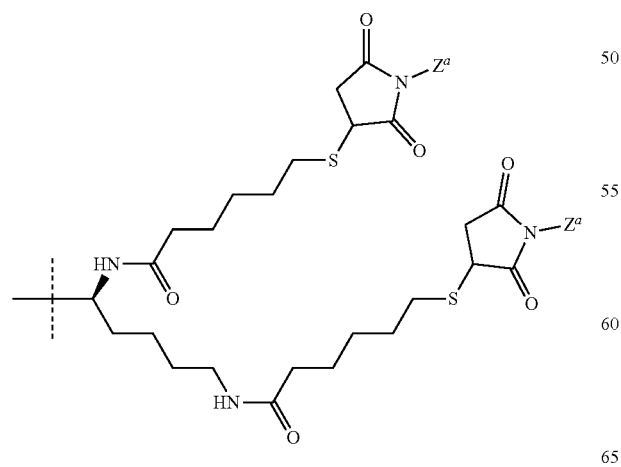

wherein each $Z^a$ is:
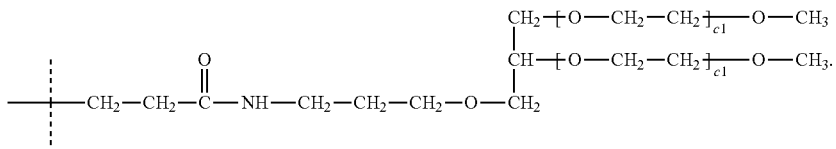
25. The dry pharmaceutical formulation of claim 24, wherein each c1 is about 225.
26. The dry pharmaceutical formulation of claim 25, wherein the CNP conjugate is at 5.8-12.4% (w/w), the succinic acid is at 0.3-3.2% (w/w), the trehalose dihydrate is at 78.8-93.8% (w/w) and the Tris is at 0.1-5.6% (w/w).
* * * * *